US012367958B2

(12) United States Patent
Bort et al.

(10) Patent No.: US 12,367,958 B2
(45) Date of Patent: *Jul. 22, 2025

(54) PERSONALIZED HEART RHYTHM THERAPY

(71) Applicant: PhysCade, Inc., Palo Alto, CA (US)

(72) Inventors: Miguel Rodrigo Bort, Valencia (ES); Mahmood I. Alhusseini, Menlo Park, CA (US); Sanjiv M. Narayan, Palo Alto, CA (US)

(73) Assignee: PhysCade, Inc., Palo Alto, CA (US)

( * ) Notice: Subject to any disclaimer, the term of this patent is extended or adjusted under 35 U.S.C. 154(b) by 251 days.

This patent is subject to a terminal disclaimer.

(21) Appl. No.: 18/080,115

(22) Filed: Dec. 13, 2022

(65) Prior Publication Data

US 2023/0290478 A1    Sep. 14, 2023

Related U.S. Application Data

(63) Continuation of application No. 17/722,030, filed on Apr. 15, 2022, now Pat. No. 11,540,879.
(Continued)

(51) Int. Cl.
*A61B 5/361* (2021.01)
*A61B 5/00* (2006.01)
(Continued)

(52) U.S. Cl.
CPC ............. *G16H 20/30* (2018.01); *A61B 5/256* (2021.01); *A61B 5/282* (2021.01); *A61B 5/283* (2021.01);
(Continued)

(58) Field of Classification Search
CPC ..... A61B 18/1492; A61B 5/283; A61B 5/361; A61B 5/363; A61B 5/4029;
(Continued)

(56) References Cited

U.S. PATENT DOCUMENTS 5,657,755 A    8/1997   Desai
7,151,964 B2   12/2006  Desai et al.
(Continued)

FOREIGN PATENT DOCUMENTS

CA    2897991 A1    7/2014
CN    102171697 A   8/2011
(Continued)

OTHER PUBLICATIONS

Alhusseini, M.I. et al. "Machine learning to classify intracardiac electrical patterns during atrial fibrillation: machine learning of atrial fibrillation," *Circulation: Arrhythmia and Electrophysiology*, Aug. 2020, vol. 13, Issue 8, pp. 719-729.
(Continued)

*Primary Examiner* — Rex R Holmes
(74) *Attorney, Agent, or Firm* — Fenwick & West LLP

(57) ABSTRACT

Disclosed includes a body surface device for diagnosing locations associated with electrical rhythm disorders to guide therapy. The device can sense electrical signals and determine multiple sites that may be operative in that patient. The patch may encompass the heart regions from where the heart rhythm disorder originates. The patch comprises an array of electrodes configured to detect electrical signals generated by a heart. A controller may determine the locations of interest based on detected electrical signals. The controller is configured to locate these regions relative to the surface patch. The system may be coupled to a sensor or therapy device inside the heart, to guide this device to a region of interest. The controller is further configured to instruct the operator to use the trigger or source information to treat the heart rhythm disorder in an individual using additional clinical data and methods for personalization such as machine learning.

10 Claims, 22 Drawing Sheets

Related U.S. Application Data

(60) Provisional application No. 63/175,986, filed on Apr. 16, 2021.

(51) Int. Cl.
| | |
|---|---|
| *A61B 5/256* | (2021.01) |
| *A61B 5/282* | (2021.01) |
| *A61B 5/283* | (2021.01) |
| *A61B 5/318* | (2021.01) |
| *A61B 5/341* | (2021.01) |
| *A61B 5/347* | (2021.01) |
| *A61B 5/363* | (2021.01) |
| *A61B 18/14* | (2006.01) |
| *A61B 34/20* | (2016.01) |
| *A61N 1/05* | (2006.01) |
| *G16H 20/30* | (2018.01) |
| *G16H 50/20* | (2018.01) |
| *A61B 5/287* | (2021.01) |
| *A61B 18/00* | (2006.01) |

(52) U.S. Cl.
CPC .............. *A61B 5/318* (2021.01); *A61B 5/341* (2021.01); *A61B 5/347* (2021.01); *A61B 5/361* (2021.01); *A61B 5/363* (2021.01); *A61B 5/4029* (2013.01); *A61B 5/4836* (2013.01); *A61B 5/6801* (2013.01); *A61B 5/6823* (2013.01); *A61B 5/7267* (2013.01); *A61B 18/1492* (2013.01); *A61B 34/20* (2016.02); *A61N 1/0565* (2013.01); *G16H 50/20* (2018.01); *A61B 5/287* (2021.01); *A61B 2018/00351* (2013.01); *A61B 2018/00577* (2013.01); *A61B 2018/00839* (2013.01); *A61B 2034/2046* (2016.02); *A61B 2562/0209* (2013.01)

(58) Field of Classification Search
CPC ........... A61B 2018/00351; A61B 2018/00577; A61B 2018/00839; A61N 1/0565
See application file for complete search history.

(56) References Cited

U.S. PATENT DOCUMENTS

| | | |
|---|---|---|
| 7,171,269 B1 | 1/2007 | Addison et al. |
| 7,300,438 B2 | 11/2007 | Falwell et al. |
| 7,850,685 B2 | 12/2010 | Kunis et al. |
| 8,538,774 B2 | 9/2013 | Michelson et al. |
| 8,715,199 B1 | 5/2014 | Macneil et al. |
| 8,880,158 B2 | 11/2014 | Spector |
| 8,954,339 B2 | 2/2015 | Schaffer |
| 9,033,892 B2 | 5/2015 | Su et al. |
| 9,050,006 B2 | 6/2015 | Narayan et al. |
| 9,078,583 B2 | 7/2015 | Nguyen et al. |
| 9,101,333 B2 | 8/2015 | Schwartz |
| 9,186,081 B2 | 11/2015 | Afonso et al. |
| 9,202,066 B2 | 12/2015 | Sinderbrand et al. |
| 9,271,680 B2 | 3/2016 | Dubois et al. |
| 9,282,908 B2 | 3/2016 | Spector |
| 9,282,910 B2 | 3/2016 | Narayan et al. |
| 9,332,915 B2 | 5/2016 | Narayan et al. |
| 9,370,329 B2 | 6/2016 | Tun et al. |
| 9,427,169 B2 | 8/2016 | Zeng et al. |
| 9,474,491 B2 | 10/2016 | Li et al. |
| 9,554,847 B2 | 1/2017 | Govari et al. |
| 9,687,166 B2 | 6/2017 | Subramaniam et al. |
| 10,016,233 B2 | 7/2018 | Pike |
| 10,070,795 B2 | 9/2018 | Macneil et al. |
| 10,105,179 B2 | 10/2018 | Harlev et al. |
| 10,136,829 B2 | 11/2018 | Deno et al. |
| 10,143,374 B2 | 12/2018 | Ruppersberg |
| 10,194,994 B2 | 2/2019 | Deno et al. |
| 10,271,739 B2 | 4/2019 | Freeman et al. |
| 10,349,855 B2 | 7/2019 | Zeidan et al. |
| 10,524,684 B2 | 1/2020 | Fay et al. |
| 10,568,686 B2 | 2/2020 | Lee |
| 10,617,318 B2* | 4/2020 | Ghosh .................... A61B 5/316 |
| 10,617,467 B2 | 4/2020 | Viswanathan et al. |
| 10,864,031 B2 | 12/2020 | Mazor et al. |
| 10,912,472 B2 | 2/2021 | Finlay et al. |
| 10,980,602 B2 | 4/2021 | Deno et al. |
| 11,051,867 B2 | 7/2021 | Babkin et al. |
| 11,206,984 B1 | 12/2021 | Boveja et al. |
| 11,540,879 B2* | 1/2023 | Bort .................... A61B 18/1492 |
| 2003/0208454 A1 | 11/2003 | Rienhoff et al. |
| 2004/0122709 A1 | 6/2004 | Avinash et al. |
| 2006/0167529 A1 | 7/2006 | Schecter |
| 2009/0318749 A1 | 12/2009 | Stolen et al. |
| 2010/0042438 A1 | 2/2010 | Moore et al. |
| 2011/0224565 A1 | 9/2011 | Ong et al. |
| 2012/0100134 A1 | 4/2012 | Lenz |
| 2012/0123232 A1 | 5/2012 | Najarian et al. |
| 2013/0267875 A1 | 10/2013 | Thapliyal et al. |
| 2014/0164784 A1 | 6/2014 | Sinderbrand et al. |
| 2015/0042646 A1 | 2/2015 | Comaniciu et al. |
| 2015/0223759 A1 | 8/2015 | Ong et al. |
| 2017/0164893 A1 | 6/2017 | Narayan et al. |
| 2017/0202515 A1 | 7/2017 | Zrihem et al. |
| 2017/0202521 A1 | 7/2017 | Urman et al. |
| 2017/0332971 A1 | 11/2017 | Macneil et al. |
| 2017/0354339 A1 | 12/2017 | Zeidan et al. |
| 2018/0110439 A1 | 4/2018 | Grunwald et al. |
| 2019/0076179 A1 | 3/2019 | Babkin et al. |
| 2020/0229866 A1 | 7/2020 | Harlev et al. |
| 2020/0245885 A1 | 8/2020 | Haeusser et al. |
| 2021/0315627 A1 | 10/2021 | Babkin et al. |

FOREIGN PATENT DOCUMENTS

| | | |
|---|---|---|
| CN | 106066933 A | 11/2016 |
| JP | 2016-179187 A | 10/2016 |
| JP | 6159250 B2 | 7/2017 |
| WO | WO 2013/013098 A1 | 1/2013 |
| WO | WO 2013/036677 A1 | 3/2013 |
| WO | WO 2016/066879 A1 | 5/2016 |
| WO | WO 2017/165830 A1 | 9/2017 |
| WO | WO 2017/165846 A1 | 9/2017 |
| WO | WO 2019/212833 A1 | 11/2019 |
| WO | WO 2021/168380 A1 | 8/2021 |

OTHER PUBLICATIONS

Cámara-Vázquez, M.A. et al, "Electrocardiogramaging including intracardiac information to achieve accurate global mapping during atrial fibrillation," *Biomedical Signal Processing and Control*, vol. 64, Feb. 2021, 102354, pp. 1-12.

Esteva, et al., "Dermatologist-level classification of skin cancer with deep neural networks," *Nature*, Feb. 2, 2017, vol. 542, pp. 115-118.

Haissaguerre, M. et al., "Driver Domains in Persistent Atrial Fibrillation," *Circulation*, 2014; 130:530-538.

Hansen, B. J. et al., "First in vivo use of high-resolution near-infrared optical mapping to assess atrial activation during sinus rhythm and atrial fibrillation in a large animal model," *Circulation: Arrhythmia and Electrophysiology*, Dec. 2018, vol. 11, Issue 12, pp. 1-3.

International Search Report and Written Opinion, Patent Cooperation Treaty Application No. PCT/IB2022/053574, Jul. 21, 2022, 19 pages.

Invitation to Pay Additional Fees, Patent Cooperation Treaty Application No. PCT/US2022/022609, Jun. 3, 2022, 3 pages.

LeCun, et al., "Gradient-Based Learning Applied to Document Recognition," Proc. of the IEEE, 1998, pp. 1-46.

Liberos, A. et al., "Phase singularity point tracking for the identification of typical and atypical flutter patients: A clinical-computational study," *Computers in Biology and Medicine*, vol. 104, Jan. 2019, pp. 319-328.

(56) References Cited

OTHER PUBLICATIONS

Marques, V.G. et al., "Characterization of atrial arrhythmias in body surface potential mapping: A computational study," *Computers in Biology and Medicine*, vol. 127, Dec. 2020, 103904, pp. 1-13.

Marques, V.G., et al., Manuscript version, "A robust wavelet-based approach for dominant frequency analysis of atrial fibrillation in body surface signals," Physiological Measurement, 2020, vol. 41, No. 7, 28 pages.

Rajpurkar, et al., Cardiologist-Level Arrhythmia Detection with Convolutional Neural Networks, Computer Vision and Pattern Recognition, Jul. 6, 2017, pp. 1-9.

Rodrigo, M. et al., "Minimal configuration of body surface potential mapping for discrimination of left versus right dominant frequencies during atrial fibrillation," Pacing and Clinical Electrophysiology, Aug. 2017, 40(8):940-946.

Rodrigo, M. et al., "Non-Invasive Assessment of Complexity of Atrial Fibrillation: Correlation with Contact Mapping and Impact of Ablation," *Circulation: Arrhythmia and Electrophysiology*, Mar. 2020, vol. 13, Issue 3, pp. 236-246.

Rodrigo, M. et al., "Non-invasive Spatial Mapping of Frequencies in Atrial Fibrillation: Correlation with Contact Mapping," *Frontiers in Physiology*, Jan. 2021, vol. 11, pp. 1-11.

Rodrigo, M. et al., Author's Manuscript, "Body Surface Localization of Left and Right Atrial High Frequency Rotors in Atrial Fibrillation Patients: A Clinical-Computational Study," *Heart Rhythm*, 2014, 27 pages.

Rodrigo, M. et al., Author's Manuscript, "Minimal configuration of body surface potential mapping for discrimination of left versus right dominant frequencies during atrial fibrillation," *Pacing and Clinical Electrophysiology*, 2017, 15 pages.

Zolotarev, A.M. et al., "Optical mapping-validated machine learning improves atrial fibrillation driver detection by multi-electrode mapping," *Circulation: Arrhythmia and Electrophysiology*, Oct. 2020, vol. 13, Issue 10, pp. 1199-1212.

\* cited by examiner

PERSONALIZED HEART RHYTHM THERAPY

CROSS REFERENCE TO RELATED APPLICATIONS

The present application is a continuation of U.S. patent application Ser. No. 17/722,030, filed on Apr. 15, 2022, which claims the benefit of U.S. Provisional Application No. 63/175,986 filed on Apr. 16, 2021, both of which are incorporated by reference in their entirety.

FIELD OF THE DISCLOSURE

The present disclosure relates generally to a non-invasive medical device and, more specifically, to a body surface device that may be used in place or in conjunction to a catheter for treating electrical rhythm disorders.

BACKGROUND

Conventional devices for treating patients with heart rhythm disorders are invasive and often associated with known risks and drawbacks. In some cases, patients may be resistant to invasive therapies. For other patients, the chance of failure in an invasive surgery is often not insignificant. To reduce potential injury caused by an invasive procedure, the sizes of the invasive surgical devices have become increasingly smaller. However, those conventional devices still face challenges in effectiveness, navigation inside a body, and identification of key regions of interest to guide therapy. Cardiac ablation for heart rhythm disorders (e.g., arrhythmias) is an invasive procedure in which probes are advanced from leg veins percutaneously to the heart to cauterize or freeze regions of the heart causing the arrhythmia. Ablation performed with a catheter guided is costly and associated with some risk of complications. Conventional devices are often guided by mapping sensors that are only able to provide data related to the patients when devices are inside the patients' bodies. Those data, despite useful for the physicians, are often insufficient for the physicians to determine the best course of therapy and sometimes even the correct region of interest to perform the surgery. The data also may not provide a sufficiently comprehensive picture of the patient's conditions and diseases. For example, invasive devices are necessarily often small and only provide a limited spatial field of view of a very localized region of a subject's organ. They can only be inserted for short periods of time, which may miss periods when the patient actually experiences a problem. Finally, invasive devices are part of in-hospital diagnostic studies which may not be practical for patients in remote or rural areas, and are also expensive. Those invasive devices thus limit access to care.

SUMMARY

In accordance with some embodiments, a system for determining a personalized therapy for heart rhythm disorders for a subject is described. The system may include a non-invasive body surface device carrying a plurality of electrodes configured to be in contact with a body surface of the subject. The electrodes may be configured to cover a spatial projection of at least a majority of a heart chamber projected on the body surface. The electrodes are capable of detecting a plurality of electrical signals generated by the heart of the subject. The system may also include a computing device configured to receive signal data generated from the body surface device. The computing device includes a processor and memory. The memory, when executed by the processor, causes the processor to perform operations that include determining locations of beats that initiate onset of a heart rhythm disorder based on the signal data and determining locations of sources for the heart rhythm disorder based on the locations of beats. The non-invasive body surface device may be used in place of or in conjunction with a sensing apparatus inside the heart (such as a catheter) to identify key regions of interest and guide the physician towards critical regions for treatment, that is the system provides directionality analysis. The body surface device can be worn continuously to monitor the subject long before an invasive device is placed in the body, thereby providing a more comprehensive set of data for determining a personalized therapy.

BRIEF DESCRIPTION OF THE DRAWINGS

Some embodiments are illustrated by way of example and not limitation in the figures of the accompanying drawings in which.

Figure 1A:
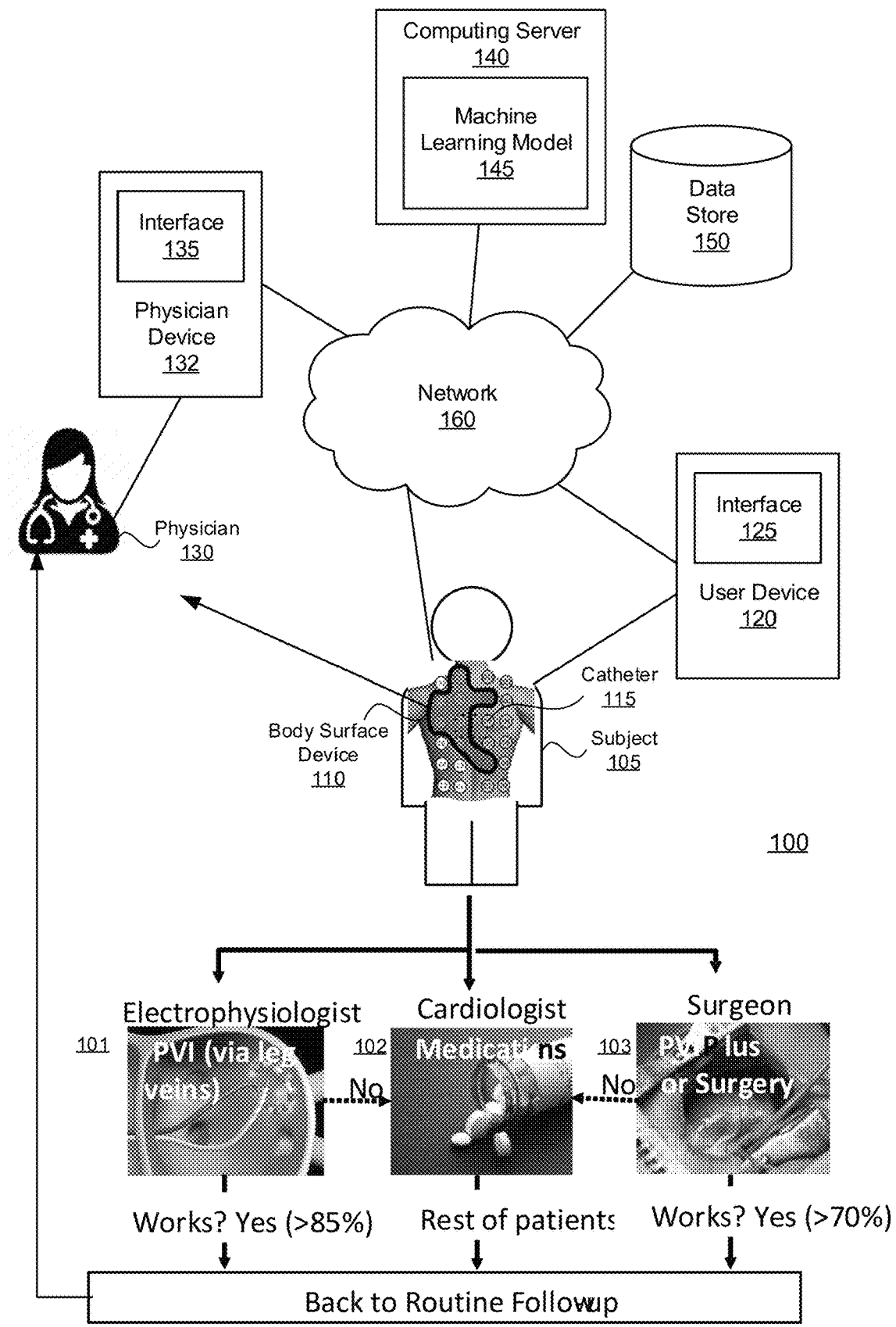
FIG. 1A is a block diagram illustrating a system environment of a heart rhythm monitoring system and a workflow of a fully remote heart rhythm evaluation pathway that is enabled by a non-invasive body surface device, in accordance with one or more embodiments.

In each figure, there can be more or fewer components/steps than shown, or certain components/steps can be replaced with others or can be organized or ordered in a different manner than is shown.

DETAILED DESCRIPTION OF EXEMPLARY EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Overview

In some embodiments, a device or a method that can identify in advance if a desired ablation approach will be successful in a given patient is disclosed. In some embodiments, the device is non-invasive, such as a device that can be worn or used externally. In some embodiments, the non-invasive device can indicate if a patient with atrial fibrillation (AF) will respond to pulmonary vein isolation (PVI). In some embodiments, the non-invasive device can indicate if a patient requires ablation in the left side of the heart, which may require more elaborate equipment and more time than ablation on the right side of the heart. The device can identify the appropriate region(s) for ablation personalized for an individual, even for complex rhythm disorders. In this way, the device can simplify the workflow for managing patients with heart rhythm disorders.

In some embodiments, a device can identify and locate critical regions (source or dominant regions) for biological rhythm disorders. The device records electrical signals and relates this to known and machine-learned patterns of critical regions. For example, in some embodiments, the device is a portable or wearable device that can identify regions where a heart rhythm disorder initiates or is maintained in a specific individual, distinct from other patients. Having identified these regions based on detected signals, the device indicates if therapy at a desired location will be effective, allowing the patient to avoid an unnecessary surgical procedure if it will not be effective, which conventionally the patient would have had to undergo to determine if the therapy would be effective. This has benefits when deciding when or how to perform an invasive procedure.

Additionally, or alternatively, the device provides navigational guidance towards these important regions to enable treatment of these regions. These steps can also be estimated based on knowledge of how patients with similar data patterns respond to therapy, rather than on actual electrical patterns recorded in that patient. Several sensor/therapy device designs are specified.

The system and method described herein thus provide a process for personalized therapy for heart rhythm disorders, which may also include a combination of lifestyle changes, medications, electrical or mechanical therapy, surgical or minimally invasive ablation, genetic or stem cell therapy.

Some embodiments employ non-invasive or invasive tools to identify patients in whom ablation therapy for complex rhythm disorders is likely to succeed. In patients amenable to ablation therapy, some embodiments include a device to map electrical patterns and provide directional guidance to move a device in three dimensions towards optimal locations for therapy. Some embodiments may provide the ability to deliver therapy directly to tissue at this location.

In some embodiments, the process has the ability to deliver personalized therapy using data from the current individual but also to estimate therapy using machine learning of data from other individuals with similar profiles based on a digital classification that can be updated using strategies such as crowd-sourcing.

The process may apply to disorders of heart rhythm, mechanical contraction, or heart failure. Other exemplary applications include seizure disorders of the brain, diseases of gastro-intestinal rhythm such as irritable bowel syndrome, and bladder disease including detrusor instability. The process may apply to chaotic disorders in these organs, such as atrial fibrillation in the heart or generalized seizures in the brain, as well as simple rhythm disorders. These examples are in no way designed to limit the scope of the disclosure for other conditions. The personalization aspect is suited for disorders that are heterogeneous syndromes rather than a single disease entity.

The process may identify patients in whom critical regions for a heart rhythm disorder arise near standard therapy targets or not. An example of this embodiment is to identify patients with AF who are likely to benefit from PVI. In patients who are unlikely to benefit from PVI, the device identifies those with localized sources in other regions of the heart that may be amenable to ablation. In those in whom such localized sources are not identified, the device identifies patients in whom defined therapy lesion sets corresponding to Maze surgery may work. The device can identify patients with other heart rhythm disorders such as ventricular tachycardia or with atypical atrial flutter in whom ablation will or will not be successful.

The process and the system that includes a body surface device may determine one or more locations of the heart that are associated with a heart rhythm disorder. The locations may include sites of origin and source regions of interests.

Sites of origin of a heart rhythm disorder may include the sites where the first beat or beats (within the first 30 seconds, typically the first 5-10 beats) which initiate the heart rhythm disorder in question, distinct from normal sinus rhythm. Site of origin may also be referred to as locations of beats that initiate onset of a heart rhythm disorder. For instance, AF often initiates from normal rhythm by a few (between one and about a dozen) premature atrial beats, which often occur at one of the pulmonary vein regions of the heart. The device is capable of identifying these originating or triggering beats. If these beats arise from the pulmonary veins, ablation to isolate the pulmonary veins and eliminate these triggers may be effective. In another patient in whom many or most trigger beats do not arise from the pulmonary veins, PVI may not be effective.

Source regions of interest are different from sites of origin. The source regions of interest, or referred to as locations of sources, indicate which regions of the heart may drive the heart rhythm disorder. Source regions can be identified during a heart rhythm disorder as patches of organized activity (a) within chaotic disorders such as atrial fibrillation in the heart, or (b) from which activation emanates to drive organized rhythms such as atrial tachycardia or ventricular tachycardia, from focal activity or small recirculating circuits known as reentrant circuits. In some embodiments, the process uses analytical tools including signal processing, artificial intelligence and machine learning to detect organized patches.

Organized patches may represent rotational activity, focal activity, repetitive activity of neither pattern, or other forms of organization. In most rhythms, a source would be a focal or reentrant (rotational) site. For atrial fibrillation (AF), sources may be any of these patterns. Sources that arise near regions that would be targeted by standard therapy, such as pulmonary veins in AF, a scar isthmus for VT or a focal brain lesion for seizure disorders and may not require additional therapy. Sources that arise from sites outside of these standard targets are often difficult to find, yet may be identified by this invention so that they may be targeted for additional therapy. This information is conveyed to the operator.

In some embodiments, the process may identify a hierarchy of heart rhythm sources, pointing out the most important for therapy. For atrial fibrillation, this differs from the prior art that often recommends treating all detected sources. The conventional prior art process requires mapping, detection and therapy of less-critical regions, which may be time consuming, adds difficulty to the procedure, and may have adverse effects. Less-critical regions identified by the prior art may be false-positives that do not require therapy.

In some embodiments, a device can identify the most important source regions for the heart rhythm disorder by quantifying their size or area within the heart chamber, or using another feature. This can be applied to organized drivers for a heart rhythm disorder such as atrial fibrillation or ventricular fibrillation. This also applies to the source driving tonic/clonic seizures in the brain. This also applies to a focus that drives irritable bowel syndrome. This hierarchy of sources, from most to least dominant, is conveyed to the operator and can be used for treatment planning.

In some embodiments, the process may map critical regions for biological rhythm disorders within the entire heart without the need for wide-area catheters such as a basket, which are cumbersome, may not cover the entire organ, and typically cannot deliver therapy. In some embodiments, the process uses non-invasive body surface potential mapping as a complement to or even a replacement of mapping from a smaller catheter inside the heart. The body surface map provides a global view of the heart rhythm disorder, which complements an intracardiac catheter. The relative sizes of these fields of view can be complementary, such as a global map from the body surface, and a catheter inside the heart which can provide a limited spatial field of view at high resolution.

A catheter may use a mapping spade placed within the heart that is physically large enough to cover the source region of simple or complex rhythm disorders, yet small enough for high-density recordings from a plurality of electrodes. The size of this intracardiac system can be personalized to the type of rhythm. The range of electrodes for this intracardiac system is from 4 to 128. An exemplary dimensional range for the mapping spade for heart arrhythmia applications is on the order of 1 cm×1 cm to 3 cm×3 cm (W×L). A typical arrangement for mapping AF sources would be 16-64 electrodes in an area of 4 $cm^2$ to 9 $cm^2$. A typical arrangement for mapping gaps in a pulmonary vein encircling line would be 4-16 electrodes in an area of 1-2 $cm^2$. A typical arrangement for mapping critical regions for ventricular tachycardia would be 9-25 electrodes in an area of 2-4 $cm^2$. The size of this spade can also be personalized to the profile of the patient, using tools such as machine learning calibrated to patients of similar clinical type and data. The size of the spade will vary with the organ being treated. The size may be smaller for a device in the brain, where small size is at a premium to avoid destruction of tissue, than for a device in the heart, where larger mapping and ablation areas are sometimes needed. The therapy tool contacts the organ by conforming to its surface at a plurality of locations.

In some embodiments, a non-invasive body surface mapping device uses a plurality of carefully placed electrodes on the body surface to map the heart rhythm disorder. In the prior art this typically needs anatomical information of the patient from detailed computed tomography (CT) or magnetic resonance imaging (MRI) data.

Conversely, in this device the resolution needed to identify important patient groups or rhythm types is fulfilled without the need for computed tomography (CT) scan or magnetic resonance imaging (MRI) data. This increases the usability of the approach over existing methods based on medical image analysis (CT or MRI scans), since the body surface device is now fully wearable and suitable for fully outpatient use without hospital visits for imaging. This is an advance over prior art methods such as Electrocardiographic Imaging (ECGI).

In some embodiments, separating rhythms arising from the left side of the heart versus the right side of the heart can be achieved without CT or MRI data. Similarly, separating originating beats from pulmonary vein regions of the left atrium (that project to the back of the chest) from other regions of the heart, can be achieved by body potential surface maps without CT or MRI data.

Heart and torso anatomy for the implementation without CT or MRI data can be obtained from multiple sources. An embodiment may use anatomy from stored databases representing standardized human anatomies and therefore not extracted from the specific patient anatomy. The stored databases may represent relationships between the heart, surrounding tissue and body surface accurately enough to be used for many purposes. As a next step, the data can be matched to a patient under consideration based on gender, chest diameter, height and weight. In some embodiments, this is sufficient to identify if a heart rhythm disorder originates in the left atrium, right atrium, left ventricle or right ventricle. In another embodiment, this generalized anatomical data is sufficient to identify if originating beats of atrial fibrillation arise from the pulmonary vein regions, that nearly always enter into the back of the left atrium, from other sites in the left or right atria. In another embodiment, this generalized anatomical data is sufficient to identify if beats of ventricular tachycardia arise from the right or left ventricle of the heart. Other applications of the generalized anatomical data integration will be apparent to one skilled in the art.

Various embodiments may use three different approaches to provide navigational guidance for a sensor or ablation probe without first collecting data using cumbersome global catheters inside the heart. One approach uses data from the body surface device. Another uses sophisticated directionality analysis from the electrode device inside the heart. A third combines data from both the body surface and electrode device within the heart.

In some embodiments, the devices may perform directionality analysis from the body surface. For example, a body surface device may identify the location of critical regions for the heart rhythm disorder. The device then calculates the direction or vector of each critical region from or to using a probe such as external ablation sources for radiofrequency ablation or intracardiac ablation catheters. This is used to provide directionality guidance for the operator to move said probe towards said critical region. Directionality greatly advances the embodiments over the prior art where the entire organ had to be mapped to identify a location of interest. One analogy is a satellite navigational system which computes directional guidance to enable a user to get from position A to B. The prior art required A and B to be identified from a map followed by interpretation by the user to who would have to infer directionality information themselves.

The directional guidance is enabled by a knowledge of what source signals should be like when actually at the source, and when at a distance. This knowledge enables the system to indicate when the recording system is directly over the source. If the recording system is at a distance, then the recording system indicates directionality towards the source.

In some embodiments, the directional guidance is tailored by additional data beyond recorded signals. Such data are created as personal digital records for an individual. The personal digital records may capture clinical, pathophysiological, laboratory, genetic or cellular data relevant to the disease being treated. This is pertinent to diseases with considerable variability in treatment outcome, such as heart rhythm disorders, that reflect varying patient profiles. For instance, a source may be near the pulmonary veins in patients with a certain profile, yet away from the pulmonary veins in patients with different profiles. Similarly, a source for ventricular tachycardia may be in the left ventricle in patients with certain profiles and right ventricle in patients with different profiles. Personal digital records may be used for data in precision medicine. This may take the form of a digital portrait of an individual by capturing data from real-time sensor streams, clinical profiles, demographics, data in electronic health records, complex data from imaging or genomic analysis. In general, clinical or laboratory data will be available most often, while genomic data may be unavailable for many patients.

Personal digital records can be used to decipher patterns of heart rhythm disorders difficult to understand by experts. Examples include identifying AF patients who will respond to PVI ablation, or VT patients who will respond to ablation. Another example is whether a patient with AF and particular signals within the heart, and a specific profile of age, gender and other diseases, is likely to respond to PVI therapy. Yet another example is whether AF in a patient with AF may be caused by rotational circuits, focal circuits, repetitive patterns, partial rotational or focal circuits, "random" activity, electrical propagation around areas of scar, or specific anatomical sites.

In some embodiments, techniques such as machine learning are used to classify an individual's personal digital records using a database of profiles associated with response or no response. Machine learning may be trained by objective and clinically relevant labels such as successful response to therapy (e.g., elimination of AF by PVI ablation, elimination of VT by ablation, improvement in left ventricular ejection fraction by ablation of heart rhythm disorder), or adverse response to therapy (e.g., prolongation of the QT interval by pharmacological agents, failure from to ablation). The machine learning model can now make a prediction for an individual, essentially finding their closest match. This trained machine learning model structures the database into a digital classification for that disease stratified by an outcome such as success or failure from therapy. Personal digital records then encode data relevant to therapy of that disease, which can be numerically matched to personal digital records of a large population to predict patient outcome.

Personal digital record analysis may be used to improve navigation within the heart to regions of interest, to identify sources, predicting the type and size of sources, and predicting the response of sources to therapy. The classification matches specific patterns of electrical signals and clinical profiles to success or failure of drugs, ablation, maze surgery or other therapy. This personalization of therapy is based on integrating data across several biological scales.

In this way, the device does not focus only on signals at the device, but takes into account modifying factors from the patient's profile. This profile is a novel combination of patient-related data at the clinical level, at the tissue level (e.g. signals, imaging data of the heart) and at the cellular level (e.g. biomarkers in the blood, unusual signals such as monophasic action potentials). By using machine learning, the device individualizes treatment and does not cater just to the statistical majority of individuals who respond to a therapy. This is another form of using FAIR software methods (Findable, Accessible, Interoperable, and Reusable) to reduce bias—for instance, to cater therapy to an individual even if they differ demographically or physiologically from the 'average' (majority) of patients in a population. Machine learning provides one approach to achieve the goal.

Personalization can be encoded by computer and analytical methods based on associative algorithms, data clusters including unsupervised machine learning, semi-supervised machine learning, and supervised machine learning and networks trained by labeled events in similar and dissimilar individuals. The tailoring of personal digital records to therapy is enabled by partitioning data with labels of 'healthful vs disease', 'responsive to therapy vs non-responsive', or multiclass response to therapies labeled such as 'therapy 1', 'therapy 2', . . . , 'therapy n'. Analysis can be one or more of supervised machine learning, neural networks, unsupervised machine learning, cluster analysis, correlation analyses, logistic regression analyses, decision trees, time domain analyses, frequency domain analyses, trigonometric transformations, and logarithmic transformations.

Personalization for heart rhythm may use signals that capture the rhythm. This may include electrical potentials (electrograms) from a non-invasive device or invasive device within or adjacent to the heart. Other signals that can be analyzed include heat (infrared), mechanical motion (piezoelectric or other sensors), chemical composition, blood flow and pressure (hemodynamics), wall tension (cardiac contractility and relaxation), Cardiac Images (magnetic resonance imaging, computed tomography), or other indices that may have diagnostic value. More detailed data includes three-dimensional anatomical and structural abnormalities. Clinical data can be extracted from history and physical examination, indices of pathophysiological comorbidities, blood and tissue biomarkers, and genetic and cellular makeup of an individual. Non-invasively, sensors may record the standard electrocardiogram, surface recordings from higher resolution body surface potential mapping (e.g., multiple ECG electrodes) or ECG imaging, cutaneous measures of nerve activity. Reflectance on the skin to visible light or other electromagnetic waveforms can be used to measure signals that indicate heart beats, either regular or irregular. This can be detected using photoplethysmography (PPG) or other forms of detecting reflectance. Visible light in the near-infrared portion of the spectrum may be useful for this. Other types of sensed signals that may be used will be apparent to one of skill in the art.

In some embodiments, a system may include a processor and a memory storing instructions that, when executed by the processor, perform operations including detecting bodily signals associated with one or more bodily functions at one or more sensors associated with the human body, processing the bodily signals to create one or more sensed signatures, processing the signatures using the digital object to determine an effector response, delivering one or more effector responses to control a bodily task and monitoring said response.

In some embodiments, a process can identify individuals amenable to therapy for treating complex rhythm disorders, provides directional guidance in 3 dimensions to move a sensor device towards optimal locations for therapy, and enable therapy to tissue at this location. In some embodiments, a non-invasive wearable device may be used by the patient at home, without hospital visits, to determine if ablation is likely to be successful or if drug therapy should be continued. This greatly improves outpatient workflow, and reduces unsuccessful procedures by better patient selection. Another embodiment is a system providing a personalized diagnosis of rhythm disorders and a 'single shot' sensor/therapy tool. Some embodiments, which are not intended to be limiting, include cardiac applications in heart rhythm disorders, coronary artery disease and in heart failure.

In some embodiments, the device is artificial intelligence (AI) enabled non-invasive ECG device, simple enough to be applied to the chest or back by the patient at home. The single-use device will be worn for up to several days, will automatically detect the onset and then ongoing episodes of the heart rhythm disorder, and alert the user when sufficient data is recorded. Data is transmitted to the cloud for analysis, from which results will be available via electronic health records for review. Analysis can indicate if that patient will respond to ablation, if ablation is needed on the left or right side of the heart, and if they may respond to medications. The physician can then make a fully remote care plan, without the need for in-hospital evaluation or invasive testing. This is useful to streamline costs, provide access to patients in rural areas, or who may not have resources to take time off to visit the hospital, and to minimize hospital contact during public health emergencies such as the COVID pandemic. One target indication is whether to refer an AF patient directly to pulmonary vein isolation (PVI), advanced ablation, or drug therapy choice. Another target indication is whether to refer a patient with supraventricular tachycardias directly to ablation, which has very high success and is curative for the rhythm of typical atrial flutter, or to identify that ablation may be more complex and should be tried only if medications do not first work.

In one or more embodiments, the device is a non-invasive electrode configuration worn on the chest, back or other parts of the body surface. It may take the form of a patch, or it may be embedded in clothing. The electrode configuration is designed to measure electrical activity and classify types of specific heart rhythm disorders. The location and configuration are separate for men and women, to optimize recordings given differences such as breast tissue. A patch has sufficient adhesive to be worn comfortably for several days. In some embodiments, the patch uses straps, such as on the wrist, ankle, chest or other body part without adhesive. Signals are transmitted by physical wire or wirelessly for analysis. Analysis may include identification of the location of beats that initiate the heart rhythm disorder, or regions that sustain heart rhythm disorders, using directional rules and using machine learning from previously-stored classification of the response of patients to various forms of therapy. If the patch is worn during invasive electrophysiological study, it can provide global guidance to allow a separate probe or ablation tool to be directed towards the region of interest to deliver therapy for the rhythm disorder.

An application in an electronic device such as a smartphone, smart tablet, or smart device can help guide the user and record the necessary positions of the patches using its optical camera, Lidar sensor (infrared, ultraviolet, or other), or both (only location of electrodes will be recorded relative to anatomy, photos will not be saved or transmitted to the Cloud). Appropriate attached and location recording will ensure proper processing of data. Alternatively, the device might have a built-in indicator to ensure proper positioning and attachment of the device.

In some embodiments, "associative learning" may refer to a process of linking input data with measurable physiology or clinical outcome. Associative learning may be iterative, enabling associations to be modified ("learned") based upon patterns of change between input and measured output (physiological or clinical endpoints).

In some embodiments, "biological signal" may refer to a signal produced by the body of a subject, and may reflect the state of one or more bodily systems. For instance, the heart rate reflects cardiac function, autonomic tone and other factors.

In some embodiments, "biometric signals" may refer to signals that provide metrics of human characteristics. Biometric identifiers can be physiological or behavioral. Physiological biometrics include, but are not limited to, DNA, fingerprints or palm prints, mouth swabs, tissue or urine samples, retinal images, facial recognition, the geometry of hands or feet, recognition of the iris or odor/scent of an individual. Physiological biometrics may also include signals such as vital signs, the ECG, the EEG, EMG, and so on. Behavioral biometrics include patterns such as gait during walking or typing rhythm. Embodiments described in this disclosure may use dynamic patterns of combined physiological and behavioral biometrics over time, which adapt to changes in the individual and are thus robust to forgery from prior "versions" of a person's signature.

In some embodiments, "body" may refer to the physical structure of a human or an animal for veterinary work.

In some embodiments, "Body Surface Potential Map" (BSPM) or "Body surface map" may be generated by using multiple electrodes on a body surface to provide a high-resolution picture of heart rhythms than available from the standard ECG. The range of leads needed for BSPM ranges from 8 to >250. In some embodiments the number of leads is ~50, often <16. Leads are typically placed on the chest, back, sides of the torso and shoulders. In some embodiments, a smaller electrode distribution that covers the projection on the body surface of the majority of at least one heart chamber is used. Some technologies require computed tomography (CT) or magnetic resonance imaging (MRI) of the heart to map heart rhythms, like electrocardiographic imaging (ECGI). In some embodiments of the current invention, CT or MRI are not needed to map heart rhythms.

In some embodiments, a "consumer device" may refer to a device that is available directly to a consumer without a medical prescription. Historically, such devices typically were not regulated by a medical regulatory agency or body, such as the U.S. Food and Drug Administration (FDA) or similar regulatory bodies in other countries. However, some devices are FDA cleared. A Consumer device may include hardware, software, or a combination thereof. It is typically not a medical device, the latter being defined as an instrument, apparatus, implement, machine, contrivance, implant, in vitro reagent, or another similar or related article, including a component part, or accessory, which is intended for use in the diagnosis of diseases or other conditions, or in the cure, mitigation, treatment, or prevention of disease, in man or other animals.

In some embodiments, "data streams" or "stream(s) of data" or "data" may refer to biological data sensed by one or more sensors that can provide real-time or near-real-time information on the biological process being sensed. Sensors in the heart may provide data comprising the electrocardiogram (ECG), Electrogram (EGM), pulse rate, pulse waveform and cardiac hemodynamics Other data may include cardiac acoustics, including analysis of heart sounds, murmurs and sophisticated analyses of hemodynamics related to the heart. Lung function may be sensed as chest movement, auscultatory sounds and nerve firing associated with breathing. Gastrointestinal disease may be sensed as sounds (borborygmi), movement on the abdominal wall, and electrical signals related to smooth muscle activity of the gut. Central and peripheral nervous system activity may be sensed as nerve activity on the scalp (electroencephalogram, EEG), remote from the scalp but still reflecting the EEG, and from peripheral nerve firing.

In some embodiments, "demographics" may refer to personal information which may include, but is not limited to, age, gender, family history of disease, ethnicity, and presence of comorbidities and which may be clinically relevant.

In some embodiments, "digital classification" may refer to a partition of different states of disease or health based on mathematical indexes. Traditional disease classifications are qualitative, such as "atrial fibrillation is more common in the older individuals, those with heart comorbidities such as valvular lesions or heart failure, those with metabolic syndrome". A digital classification translates this broad dataset into quantifiable primary and secondary data elements (data vectors). The likelihood that a disease entity $D_n$ is present in a specific individual is approximated by the probability $p(D_n)$:

$$p(D_n) = \sum_{i=1}^{m} \frac{(k_n p(V_{n,i}))}{k_n}$$

Where m is the number of available data input types, n is the disease being considered, and $p(V_{n,i})$ is the probability that data vector $V_{n,i}$ contributes to disease n for input i, and $k_n$ is a weighting constant for disease n. These elements are integrated into the classification, which computes probabilities that a specific data input contributes to disease. Probabilities can be obtained from population data, in which the profile of a specific person is matched to the most-similar individuals or profiles in that population. The probability can also be obtained from data in this individual alone, compared to times of health (self-reported or adjudicated) and times of disease (self-reported or adjudicated). These calculations can be performed by traditional estimating equations but may also by statistical techniques and machine learning. A digital classification (i.e. a classification) represents a disease entity stochastically by the aggregate of abnormalities in multiple related data inputs. This process is dynamic since the equation reflecting disease will change when data is added, when data changes, and when the state of health or disease is updated. This is an approach to integrate massive amounts of data from traditional data sources as well as wearable devices in an individual, or massive amounts of data from several individuals as a crowd-sourced paradigm.

In some embodiments, "electrocardiographic imaging (ECGI)" may refer to a data source that refers to a process that records body surface potentials on the chest then uses mathematics to calculate electrical activity at precise regions of the heart. The inverse solution develops mathematical transforms that may need detailed knowledge of anatomy inside the chest, typically provided by computed tomography (CT) or magnetic resonance imaging (MRI), or from standardized anatomical databases, and make assumptions about their conductivity, resistance and other electrical properties. In this way, body surface potentials can be mapped to the heart.

In some embodiments, an "electrocardiographic (ECG) patch" may refer to a device that includes electrodes to sense cardiac rhythm. The ECG patch may be a data source. The ECG patch may be placed in regions of the body, such as on the back. Depending on the body placement and approaches used to analyze data generated by the ECG patch, the ECG patch can discriminate heart rhythm activation patterns of interest. In some embodiments, an ECG patch on the back can record atrial activation to guide AF therapy, which can be tailored to best record activity in women versus men, and for different rhythm applications. The ECG patch does not necessarily require CT or MRI imaging for analysis, and is a form of body surface potential mapping without mapping the entire body torso.

In some embodiments, "historical data" may refer to stored data, which may include reports from medical imaging, e.g., magnetic resonance imaging (MRI), computed tomography (CT), radiological, or other scans of an organ, data from genetic testing analyses (e.g., presence of one or more genomic variants), previously-obtained ECG reports, pathology, cytology, information on genomic variants (genetic abnormalities and non-disease causing variations), and other laboratory reports. This also includes clinical demographics such as age, gender, other conditions present in the individual, and a family history of diseases. Historical data may further include additional personal historical details that could be relevant to generating the personal digital record, for example, socioeconomic status including income strata, mental illness, employment in a high-stress profession, number of pregnancies (in women), engaging in high-risk behaviors such as smoking, drug or alcohol abuse, etc.

In some embodiments, "machine learning" may refer to a series of analytic methods and algorithms that can learn from and make predictions on data by building a model. Machine learning is classified as a branch of artificial intelligence that focuses on the development of computer programs that can automatically learn to produce predictions when exposed to data. In some embodiments, machine learning is one tool used to create the digital network and personal digital records linking sensed or recorded data with a specific output such as response to therapy, or ability to maintain normal rhythm. For applications in the brain, outputs could include absence of seizure activity. Machine learning techniques include supervised learning, transfer learning, semi-supervised learning, unsupervised learning, or reinforcement learning. Several other classifications may exist.

In some embodiments, "unsupervised machine learning" may include methods of training of models with training data without the need for training labels. Techniques in unsupervised machine learning may include cluster analysis that may be used to identify internal links between data (regardless of whether data is labeled or unlabeled). In some embodiments, patterns (clusters) could be identified between clinical data (such as diagnosis of atrial fibrillation, or presence of heart failure, or other disease), family history, data from physical examinations (such as regularity of the pulse, low blood pressure), data from sensors (such as altered temperature, altered skin impedance), electrical data (atrial waveforms on the ECG), imaging data (enlarged left atrium or reduced), biomarkers, genetic and tissue data as available. Another technique is to use autoencoders, to featurize and compress input data. Autoencoders are sometimes described as 'self-supervised' since the model input and output are the same.

In some embodiments, "supervised machine learning" may include methods of training of models with training data that are associated with labels. Techniques in supervised machine learning may include methods that can classify a series of related or seemingly unrelated inputs into one or more output classes. Output labels are typically used to train the learning models to the desired output, such as favorable patient outcomes, accurate therapy delivery sites and so on. Supervised learning may also include a technique known as 'transfer learning', where a pretrained machine learned model trained on one set of input or task, is retrained or fine-tuned to predict outcomes on another input or task.

In some embodiments, "semi-supervised machine learning" may refer to a process that combines techniques from supervised and unsupervised machine learning to address cases where a large amount of data is available but only a portion of the data is labeled. One approach is to impute or infer labels from similar data, based on a comparison of the data under consideration to other data within the database. Another approach is to generate labels for an unlabeled dataset based on the portion of data that is labeled. Yet another approach is to use training from a different problem or a different dataset to generate labels for these data. Such techniques are used to improve the learning accuracy of models by creating "pseudo labels" for the unknown labels (an approach known as transductive learning) and to improve model learning by adding in more input to output examples (inductive learning).

In some embodiments, "reinforcement learning" may refer to a form of machine learning which focuses on how software agents take actions in a specific environment to maximize cumulative reward. Reinforcement learning is often used in game theory, operations research, swarm intelligence and genetic algorithms and has other names such as approximate dynamic programming One implementation in machine learning is via formulation as a Markov Decision Process (MDP). Reinforcement learning may differ from supervised machine learning in that it may not use matched inputs and labeled outputs, and actions that result in sub-optimal rewards are not explicitly corrected (unlike supervised learning which may correct suboptimal rewards via e.g., back propagation algorithms in a perceptron).

In some embodiments, a "medical device" may refer to an instrument, apparatus, implement, machine, contrivance, implant, in vitro reagent, or another similar or related article, including a component part, or accessory, which is intended for use in the diagnosis of disease or other conditions, or in the cure, mitigation, treatment, or prevention of disease, in man or other animals.

In some embodiments, "neural networks" may refer to a class of machine learning models that include interconnected nodes that can be used to recognize patterns. Neural networks can be deep or shallow neural networks, convolutional neural networks, recurrent neural networks (gated recurrent units, GRUs, or long short term memory, LSTM, networks), generative adversarial networks, and auto-encoders neural networks. Artificial neural networks can be combined with heuristics, deterministic rules and detailed databases.

In some embodiments, personal digital records may include data related to health or disease of an individual. The personal digital records may integrate several clinical data streams which may or may not include cellular, genomic, proteomic, metabolomic or other data. The personal digital record may be stratified, partitioned or separated by desired groups, such as response to specific therapy, presence of a heart rhythm disorder, presence or seizure activity of the brain, good health or other attribute in that person. The personal digital record for an individual can be compared to a digital classification of data from a large group to identify individuals with 'similar' profiles. This comparison to similar profiles may be done mathematically and, once done, may enable predictions or selection of optimal therapy based on the successful response of those similar individuals. In some embodiments, the comparison may take the form of a mathematical 'best estimation' since all required data may not be available in the personal digital record of a given patient or in the digital classification.

Personal digital records enable personalized medicine in an individual. This is an alternative to the 'one size fits all' approach that commonly applies one therapy or approach to all patients of a subjective 'type'. Data elements used to create the personal digital record may represent the individual's health state, weighted by their likely contribution to the specific disease or index of health being considered. Personal digital records may be matched to a digital classification by algorithms that take into account the calculated or documented probability of the impact of each data type on health or disease. This may use deterministic algorithms or iterative processes including machine learning. For example, a personal digital record for heart rhythm may primarily consider heart rate and electrographic signals (surface ECG and intracardiac), and then consider heart function, prior history of heart rhythm issues, prior therapies, and so on. Greater mathematical weighting may be given to these data elements. Data from other organ systems can also then be included, and can enable a more comprehensive assessment and a closer match to other individuals in a digital classification. Such other data streams may include changes in breathing rate (e.g., lung sensors), changes in nerve firing rate (e.g., nerve function). Other data elements may include abnormal cardiac ejection fraction, location and presence of structural abnormalities of the heart. Historical data including age, gender, medication use, family history, laboratory values and genetic data can also be included in the personal digital record.

In some embodiments, "population data" may refer to a determinant of the accuracy of a process. This is to create a digital classification of patients in the population. The classification may include some or all data elements in the personal digital record of the individual under consideration. Mathematical analyses are used to compare the personal digital record of the individual to the digital classification and calculate the best match. If the index individual is very different from the reference population then the digital classification may not adequately represent this individual. In this case, data may be derived primarily from that individual, using prior data at times of adjudicated health or adjudicated illness. If the reference population is broad but has other limitations, such as not having sufficient data points for an accurate digital classification, or not having well-labeled data, the classification may be less useful. In some embodiments, the ideal data set may include data that are well labeled and from a large number of individuals that represent the entire population, which can be grouped by desired outcome to create a digital classification.

In some embodiments, "sensors" may include devices that can detect biological signals from the body of an individual. A sensor may be in direct contact with the body or may be remote. When applied to a group of individuals, sensors may represent all or part of a defined population. Electromagnetic sensors can sense electromagnetic signals relating to the electromyogram (EMG), electroencephalogram (EEG), electrocardiogram (ECG), nerve firing, electromagnetic light (visible or invisible such as near infrared or infrared) or other emitters. In some cases, the term "sensor", especially when describing certain cardiac applications in which electrical information is detected, may be used interchangeably with "electrode", "electrode catheter", "probe" or "catheter." Electrical sensors can also detect bioimpedance, such as conductance across the skin that decreases in the presence of electrolyte solutions such as sweat when a person perspires, and that may occur during times of sympathetic nervous system predominance Sensors can also detect other chemical changes via current flows. Sensors also include devices that detect temperatures, such as a thermistor or other thermal detector. Sensors can detect light such as changes in the color of reflected or emitted light from heart activity (photoplethysmography), changes in peripheral oxygenation (e.g., cyanosis, anemia, vasodilation on the skin). Sensors can detect sound via a microphone. This can be used to sense sounds from the heart, lungs or other organs. Sensors can detect contact force, pressure, or other vibrations or movement via piezoelectric elements. Sensors can detect chemicals directly, using specialized sensors for hormones, drugs, bacteria and other elements that are typically transduced on the device to an electrical signal. Examples include motion sensing of chest wall movement from a breath or heartbeat, chest wall vibrations from certain types of breath (e.g., a loud obstructive breathing sound) or heart sound (e.g., a so-called "thrill" in the medical literature). Breath sensors can detect movement of the chest wall, abdomen or other body parts associated with ventilation, or acoustic data (sound) associated with breaths, or oxygenation associated with breathing. Chemical sensors can detect chemical signals on the skin or other membranes that reflect body chemistry such as oxygenation and deoxygenation, acidosis (pH), stress (catecholamines), glucose levels, certain drugs or other states that will be familiar to those skilled in the biochemistry arts. Sensors can also detect images using a camera or lens requiring contact from the fingerprint or other body part, or sense movement from specific muscles, or sense iris dilation or oscillations from photosensors in a contact lens. Positional sensors can identify positions of body parts and changes over time (including gait) or contact sensing of the position of certain body parts at one point in time or over time (e.g., a facial droop, a facial tick or another idiosyncratic movement) In exemplary embodiments of the inventive system, multiple sensors may be used in communication with a central computing device or which may form a network linked via BLUETOOTH, WI-FI, or other protocol to form an intranet or internet of things (IoT) of biological sensors.

In some embodiments, "Signal" may include electronic, electromagnetic, digital or other information that can be sensed or acquired. Sensed signals are detected unaltered from their natural form (e.g., recorded) with no transformation. Sensed signals are typically biological signals. Sensed signals can be detected by humans (e.g., sound, visual, temperature) but also machines such as microphones, auditory recorders, cameras, thermometers. Acquired signals are detected in a transformed state, such as an ECG recording. Such signals may be biological, since cardiac bioelectricity generates the ECG, or non-biological signals, e.g., vibration sensed after application of sonic or ultrasonic energy, or a haptic signal transduced from a sensed electrical, sonic or another signal. Signals may be sensed via physical contact with a sensor.

In some embodiments, "smart data" may refer to application-specific information acquired from information sources that can be used to identify and/or act upon normal or abnormal function in an application. Smart data is thus different from the term "big data". "Smart data" is tailored to the individual, and tailored to address the specific task or application—such as to maintain health and alertness or detect and treat disease such as sleep-disordered breathing, using appropriately tailored knowledge. Such knowledge may be based on physiology, engineering, or other principles. Conversely, "big data" is often focused on extremely large datasets for the goal of identifying statistical patterns or trends without an individually tailored link. In machine learning parlance, smart data may result from supervised learning of datasets to a known output, while big data simply speaks to the volume of data without necessarily implying any knowledge of the significance of specific datasets.

In some embodiments, a "subject" may refer to a human or an animal for veterinary work.

Other biological terms take their standard definitions, such as heart failure, tidal volume, sleep apnea, obesity and so on.

The following description and accompanying figures provide examples of applications of the inventive system and method for personalizing treatment by analyzing personal digital records of health and disease, to detect regions of interest for biological rhythm disorders and treat such regions of interest. The examples described herein are intended to be illustrative only. As will be evident to those of skill in the art, additional variations and combinations may be formed employing the inventive principles disclosed herein.

Example System Environment

FIG. 1A is a block diagram illustrating a system environment 100 of a heart rhythm monitoring system and a workflow of a fully remote heart rhythm evaluation pathway that is enabled by a non-invasive body surface device 110, in accordance with one or more embodiments. In some embodiments, the non-invasive procedure may be replaced or supplemented by an invasive procedure such as a surgery or putting a catheter 115 inside the body of the subject 105. In some embodiments, the catheter 115 is not needed. The system environment 100 shown in FIG. 1A includes a subject 105, a body surface device 110 attached to the subject's body, a user device 120, a physician 130, a physician device 132, a computing server 140, a data store 150, and a network 160. In various embodiments, the system environment 100 may include fewer or additional components. The system environment 100 may also include different components.

The subject 105 may be someone who is diagnosed with a health condition such as a heart rhythm disorder or another type of health condition such as seizure disorders of the brain, diseases of gastro-intestinal rhythm such as irritable bowel syndrome, and bladder disease including detrusor instability. A heart rhythm disorder may refer to a clinically diagnosed condition such as arrhythmias or any heart rhythm irregularities that may or may not have been formally diagnosed. The subject 105 may also be referred to as a patient, a user, an individual, or a target individual.

A body surface device 110 is worn by or otherwise attached to the subject 105. The body surface device 110 includes one or more sensors that detect biological signals of the subject 105 such as the heart rates and rhythm. Depending on the type of health condition, the biological signals measured by the body surface device 110 may also be different. In various embodiments, the body surface device 110 may take a different form, shape, and structure and include different types of sensors. Non-limiting examples of the body surface devices 110 are discussed in FIG. 2A through FIG. 3B. While the body surface device 110 is described as a surface device, the body surface device 110 may generally be referred to as any non-invasive device that may or may not be directly attached to the skin or another surface of the subject 105. The body surface device 110 may be network connected or may include a wire port for connection with an electronic device (e.g., user device 120 or another transceiver) for downloading and uploading of signal data collected by the body surface device 110.

A catheter 115 may take the form of a conventional catheter well known in the art or a specific ablation catheter equipped with one or more of ablation, sensing, and/or mapping capabilities. For example, in some cases, an ablation catheter may combine the functionality of sensing from multiple channels at high resolution, with therapy delivery (ablation) functionality into one tool. In such cases, the ablation catheter may include a spade, a shaft, and a controller. The spade may include an array of sensing electrodes for guiding the ablation catheter to one or more source regions. The spade may also include one or more ablation components for modifying the tissue region at a source region of an arrhythmia. The spade may also include other components such as one or more irrigation pores for venting irrigant to tissue, one or more chambers for storing fluids such as coolant used for cryoablation, etc. The proximal end of the spade may be coupled to a shaft, which is steerable by a controller for controlling the movement of the spade. In some cases, a shaft may further one or more contact sensors for sensing whether the spade is in contact with tissue. Various types of sensors may be implemented as the contact sensor. In some cases, the contact sensor may take the form of a force sensor measuring a force applied to the force sensor. The force sensor determines that the spade is sufficiently in contact with the tissue surface when a force applied to the force sensor is above a threshold, e.g., 0.25 Pascals. Another type of sensor that may be implemented is a proximity sensor which senses a distance of another surface to the proximity sensor. The proximity sensor may measure the distance via capacitive sensing. A distance of the tissue surface to the proximity sensor affects capacitance of a capacitor implemented in the proximity sensor. The change in capacitance is used to calculate the distance of the tissue surface to the capacitor in the proximity sensor. The proximity sensor may determine that the spade is sufficiently in contact with the tissue surface depending on the distance of the tissue surface being within a threshold distance, e.g., 0.1 millimeters.

In some cases, the spade of a specific ablation catheter may also include an array of sensing electrodes that are placed on the contact surface of the spade configured to come into the contact surface. The sensing electrodes may be arranged in any suitable patterns, linear or non-linear, regular or irregular, equally spaced or not, symmetrical or not. For example, the sensing electrodes may be arranged evenly in a rectangular grid. The size and spacing of the sensing electrodes may determine a resolution of sensing of the electrical signals. The sensing electrodes detect electrical signals of a tissue. Other sensors can be placed instead, to measure heat (infrared), mechanical motion (piezoelectric or other sensors), chemical composition or other indices referenced throughout the specification.

The ablation components of the catheter 115 may modify tissue with ablation energy. The ablation components deliver ablation energy to the tissue or aid in delivery of the ablation energy to the tissue. The ablation components may include ablation electrodes that provide electromagnetic energy as the ablation energy. The electromagnetic energy may include radio frequency electromagnetic waves, but may also include other frequencies of electromagnetic waves. In some cases, the ablation components are cryoablation loci that provide freezing energy as the ablation energy.

In some cases, both detector and treatment elements may be included in the same physical device, thereby eliminating the need to use separate tools for each. This reduces time and improves workflow, and may improve accuracy since locations of desired target regions do not have to be stored or registered and then re-found using a separate tool.

The user device 120 is a computing device that is capable of receiving user input as well as transmitting and/or receiving data via a network 160. Example computing devices include desktop computers, laptop computers, personal digital assistants (PDAs), smartphones, tablets, or other suitable electronic devices. The user device 120 may be controlled by the subject 105 and may be the subject's smartphone. A user device 120 communicates to other components via the network 160. In some embodiments, a user device 120 executes an application that launches a graphical user interface (GUI) 125 for a user of the user device 120 to interact with the computing server 140. For example, the subject 105 may view data illustration, alerts and other information generated from the analysis of signals from the body surface device 110 and/or the catheter 115.

The user interface 125 may be part of a software application provided by the computing server 140 for the subject 105 to control the body surface device 110 or to review data and information related to the body surface device 110 and/or the catheter 115. For example, the user interface 125 may be a patient-physician portal or an interface for a mobile application that pairs with the body surface device 110. The user interface 125 may take various forms. The GUI may be an example of a user interface 125. A user device 120 may also execute a web browser application such as a web form to enable interactions between the user device 120 and the computing server 140 via the network 160. In another embodiment, the user interface 125 may take the form of a software application published by the computing server 140 and installed on the user device 120. In yet another embodiment, a user device 120 interacts with the computing server 140 through an application programming interface (API). The computing server 140 may provide the predictive binding analysis as a software as a service (SaaS) platform through the interface 125.

The physician 130 may provide both in person and remote consultation to the subject 105 and may remotely and continuously monitor the conditions of the subject 105 based on data and recommendations provided by the computing server 140, which may collect the signals generated by the body surface device 110 and/or the catheter 115. The physician 130 controls the physician device 132 that allows the physician 130 to review data of the body surface device 110 and/or the catheter 115 and communicate with the subject 105 remotely through the interface 135. The physician device 132 and the interface 135 are respectively similar to the user device 120 and interface 125. The examples and forms of the physician device 132 and the interface 135 are not repeatedly discussed.

The computing server 140 may include one or more computing devices that operate one or more machine learning models 145 that may include one or more predictive models that analyze the information provided by the subject 105 and the physician 130 and data generated from the body surface device to generate recommendations such as therapy recommendations and predictions related to the subject's conditions. In various embodiments, the computing server 140 may take different forms. The computing server 140 may be a server computer that includes software and one or more processors to execute code instructions to perform various processes described herein. The computing server 140 may also be a pool of computing devices that may be located at the same geographical location (e.g., a server room) or be distributed geographically (e.g., cloud computing, distributed computing, or in a virtual server network). The machine learning models 145 may be iteratively trained. The algorithms run by the computing server 140 may be used to identify a rhythm disorder and direct treatments to the rhythm disorder. In some embodiments, the algorithms may take the form of software as a medical device.

While in this example system environment 100 the computing server 140 is illustrated as a remote server, in various embodiments different processes and software algorithm described in this disclosure (e.g., processes described in FIG. 4 through FIG. 9C) may also be performed by a controller such as a computer that is attached to or in communication with the body surface device 110, the catheter 115, the user device 120, and/or the physician device 132. For example, in some embodiments, the machine learning model that is used to determine rhythm locations may be included in a local device at a point of care. Signal data generated by the body surface device 110 or the catheter 115 does not always need to be uploaded to the cloud.

The data store 150 may be one or more computing devices that include memories or other storage media for data related to the subject 105 such as data generated from the body surface device 110. Some of the data may take the form of personal digital records. The data may be routed by the computing server 140 and directly uploaded from the user device 120 or the body surface device 110. The data store 150 may be a network-based storage server (e.g., a cloud server). The data store 150 may be part of the computing server 140 or may be a third-party storage system such as AMAZON AWS, AMAZON S3, DROPBOX, RACK-SPACE CLOUD FILES, AZURE BLOB STORAGE, GOOGLE CLOUD STORAGE or ENGINE, etc. In some cases, the data store 150 also may be referred to as a cloud storage server 150.

The more detailed and broad the data included in personal digital records, e.g., the "richer," the data elements, the more comprehensive is the digital classification (i.e. a classification) and the more accurate will be personalization of therapy. Personal digital records can input data from the electronic health record, such as heart rate, weight, other stored elements, and/or complex or sophisticated data which may change dynamically over time (e.g., proteomics and biomarkers) or may not change over time (e.g., genetic data). Other phenotypes may be clinical labels not tracked by a biomarker, or those with loose statistical definitions such as race or ethnic susceptibility.

Personal digital records can combine data from sensors, medical or consumer machines alone or in combination. Data can be raw or first modified by signal processing. Data may come from specialized equipment such as imaging systems or novel wearable sensors. Data may come from multiple people for crowd-sourced population data. Data from pre-existing systems may include data from multiple hospitals in a large digital registry of de-identified data, contributing diverse patients, practice patterns and outcome data from different therapies. Such approaches may involve blockchain technology to ensure data security, traceable logs of data transactions, and data access across multiple physical storage systems.

Data received by the data store 150 may include data transmitted from the body surface device 110 and/or the catheter 115 and may also include other data. Various data may take the form of sensed data streams. Sensed data streams may record from relevant tissue including the heart, nerves that supply regions of the heart, regions of the brain that control the nerves, blood vessels that supply regions of the heart, and tissues adjacent to the heart. For complex heart rhythm disorders, inflammation is a likely contributor that is often not included in phenotyping. Inflammation may cause some arrhythmias after surgery or other conditions such as myocarditis. The link of obesity with atrial fibrillation may operate through inflammation in pericardial fat, in turn, due to reactive oxygen species. Inflammatory findings may have a significance that is undefined in any given person at one point or overtime, or between people. The "inflammasome" may measure the impact of inflammation from various pathological insults at the cellular or tissue level, yet is not commonly done, may not assess circadian fluctuations, have unclear relationships to inflammation for the entire body, and may differ between individuals. It is thus unclear how to establish "nomograms" of normal or abnormal states.

Biomarkers of inflammation can be a useful data stream. A personalized state of inflammation may be detected by inflammatory cells in the inflamed organ system, or in body fluids such as the blood, urine or cerebrospinal fluid. Byproducts of inflammation can be detected by elevated concentrations of biomarkers and cytokines such as interleukin-6, nerve growth factor, matrix metalloproteinases. Conversely, several physiological markers are abnormal in inflammation (e.g., "acute phase reactants"). Inflammation causes, in addition to elevated white cell counts, abnormalities in red cell count, in hemoglobin concentration, and in a myriad of acute phase reactants such as C-reactive protein, erythrocyte sedimentation rate or white cell counts. In the heart, it is well known that serum troponin, a marker of cardiac cell destruction, is an acute phase reactant whose levels fall with inflammation ('inverse acute phase reactant').

In the subgroup of patients with inflammatory causes, arrhythmias may be treated by anti-inflammatory therapy including immunosuppression with agents such as tacrolimus, a hitherto unrecognized therapy for complex arrhythmias such as atrial fibrillation. Other immunosuppression therapy such as steroids or non-steroidal agents, or cell therapy may be effective. One rationale is that patients who receive heart transplants rarely develop AF. While benefit is attributed to surgical isolation of the pulmonary veins during transplantation, PVI works in only 40-65% of patients in other populations. Another possible mechanism of AF suppression in heart transplant patients is immunosuppressive agents. The use of immunosuppression for complex rhythm disorders including AF has rarely been used. Digital taxonomies and personal digital records in some embodiments can identify individuals with inflammatory mediated arrhythmias in whom anti-inflammatory therapy including immunosuppression may be useful.

For non-heart related applications, measurable body systems and sensed signals include central and peripheral nervous systems, the electroencephalogram (EEG) measured on the scalp, invasive electrode recordings or signals from peripheral nerves. Measurements may also include the respiratory system, skeletal muscles and skin, any indexes of electrical signals, hemodynamics, clinical factors, nerve signals, genetic profile, biomarkers of metabolic status, and patient movement. Other input data elements may come from imaging, nuclear, genetic, laboratory, or other sources, and may also be sensed as a stream (e.g., transmitted to the system), or input as values at specific points in time.

In general, sensors may be in physical contact with the patient's body with the sensed data stream acquired by one of wired or wireless transmission. The sensor may be one or more of an electrode, an optical sensor, a piezoelectric sensor, an acoustic sensor, an electrical resistance sensor, a thermal sensor, an accelerometer, a pressure sensor, a flow sensor, and an electrochemical sensor. Sensors may be non-contact, tracking physiological signals via emitted electromagnetic radiation such as heat signatures (infrared), periodic alterations in skin reflectance that indicate heart rate (visible light), sonic signals that indicate breaths, and others evident to those skilled in the art.

Personalized therapy in an individual may include modifying at least a portion of tissue by one or more of ablation by energy delivery via contact devices, energy delivery by noncontact devices, electrical therapy, thermal therapy, mechanical therapy, delivery of drug therapy, delivery of immunosuppression, delivery of stem cell therapy, and delivery of gene therapy.

Personalized therapy in an individual may further include guiding therapy by another device. This may include guiding placement of a pacing lead to the optimal site to stimulate the heart. This may include guiding the selection of sites for cardiac resynchronization therapy pacing. This may also include pacing sites that avoid pre-existing scars where signals are very small or attenuated.

In many cases, the personal digital record is then updated with personal historical data, the qualitative disease classifications, the actual intervention, its spatial location and other details, and its outcome.

The communications between the user devices 120, the physician device 132, the computing server 140 and the data store 150 may be transmitted via a network 160, for example, via the Internet. The network 160 provides connections to the components of the system 100 through one or more sub-networks, which may include any combination of local area and/or wide area networks, using both wired and/or wireless communication systems. In some embodiments, a network 160 uses standard communications technologies and/or protocols. For example, a network 160 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 160 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 160 may be represented using any suitable format, such as hypertext markup language (HTML), extensible markup language (XML), or JSON. In some embodiments, all or some of the communication links of a network 160 may be encrypted using any suitable technique or techniques such as secure sockets layer (SSL), transport layer security (TLS), virtual private networks (VPNs), Internet Protocol security (IPsec), etc. The network 160 also includes links and packet switching networks such as the Internet.

The system environment 100 provides a novel process of a remote rhythm evaluation pathway that is enabled by the non-invasive body surface device 110. By way of using heart rhythm disorder as an example, the body surface device 110 identifies or predicts patients who will benefit from simple ablation, medications, or who may require complex surgery. For atrial fibrillation (AF), ablation therapy may include pulmonary vein isolation (PVI) 101, medications 102 may include Dofetilide or Sotalol (both of which require initiation in the hospital) or Maze surgery 103. The computing server 140 analyzes the data from the body surface device 110. The recommendations from the computing server 140 simplify and accelerate care without disrupting existing practice patterns. In this embodiment, patients 105 with AF are seen by their physicians 130. The body surface device 110 may be delivered to a patient 105 such as by mail with online or in-person instructions for use. The body surface device 110 is worn by the patient 105 to collect sufficient data, which may be hours, days or weeks. Data is analyzed locally in a device or in the Cloud computing server 140 (or using a commercial computing engines such as AWS or Google Cloud) then interpreted electronically by the physician 130. Alerts can be provided in a patient-friendly fashion by a dedicated device or on a smartphone app via interface 125. Data can be transmitted via electronic medical records to the physician 130. The patient 105 may be sent directly to an appropriate specialist. This may be an electrophysiologist for PVI ablation, an electrophysiologist or surgeon for advanced ablation beyond PVI, or a cardiologist for medications.

Figure 1B:
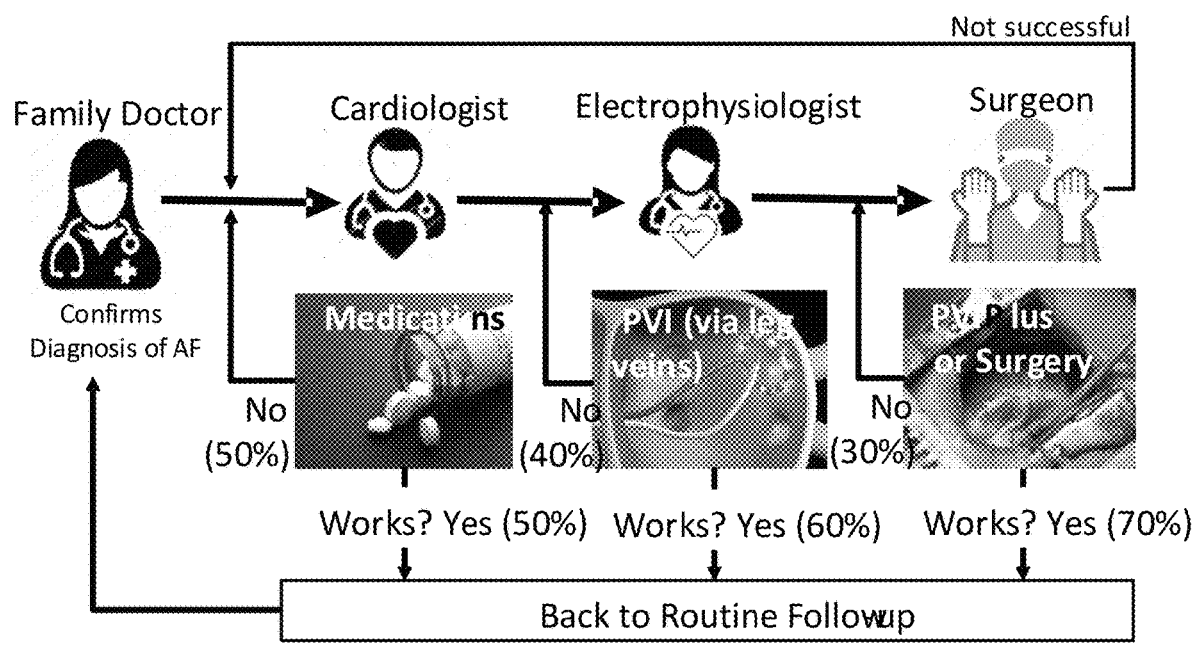
FIG. 1B is a conceptual block diagram illustrating the conventional clinical workflow.

The novel remote rhythm evaluation process improves upon conventional clinical workflow for managing patients with complex arrhythmias FIG. 1B is a conceptual block diagram illustrating the conventional clinical workflow. Few tools currently exist to objectively guide the selection of a drug or various types of ablation therapy in such patients. Diagnosis is often made by a general physician, who may refer the patient to a cardiologist. The cardiologist may choose to start medications or refer the patient for an invasive therapy such as an ablation. Objective tools to guide this selection do not exist. As such, therapy often starts empirically with medication, the less invasive and initially less costly approach. However, drug therapy often requires in-hospital initiation, may fail over months or years, requires prolonged follow-up and can be costly long term. Alternatively, personal preference may guide referral for cardiac ablation, in which probes are advanced from leg veins percutaneously to the heart to cauterize or freeze regions of the heart related to the arrhythmia. Acutely, ablation is costly with some risk of complications, yet may be cost-effective in the long term by eliminating arrhythmia in many patients. Nevertheless, it may fail in about half of patients, of whom some are referred for more invasive surgery. Ultimately, 20-25% of AF patients are resistant to all invasive therapies. A similar line of reasoning exists for patients with ventricular arrhythmias, in whom about 50-60% may respond to ablation. This treatment workflow is lengthy, costly and exposes patients to the risks of procedures that may fail for them and have health and cost risks. This subjective approach may also perpetuate inequalities, for example, women and minorities are referred less often and later for ablation for unclear reasons. Tools are thus needed to objectively identify optimal treatment pathways without subjective bias.

Example Body Surface Devices

Figure 2A:
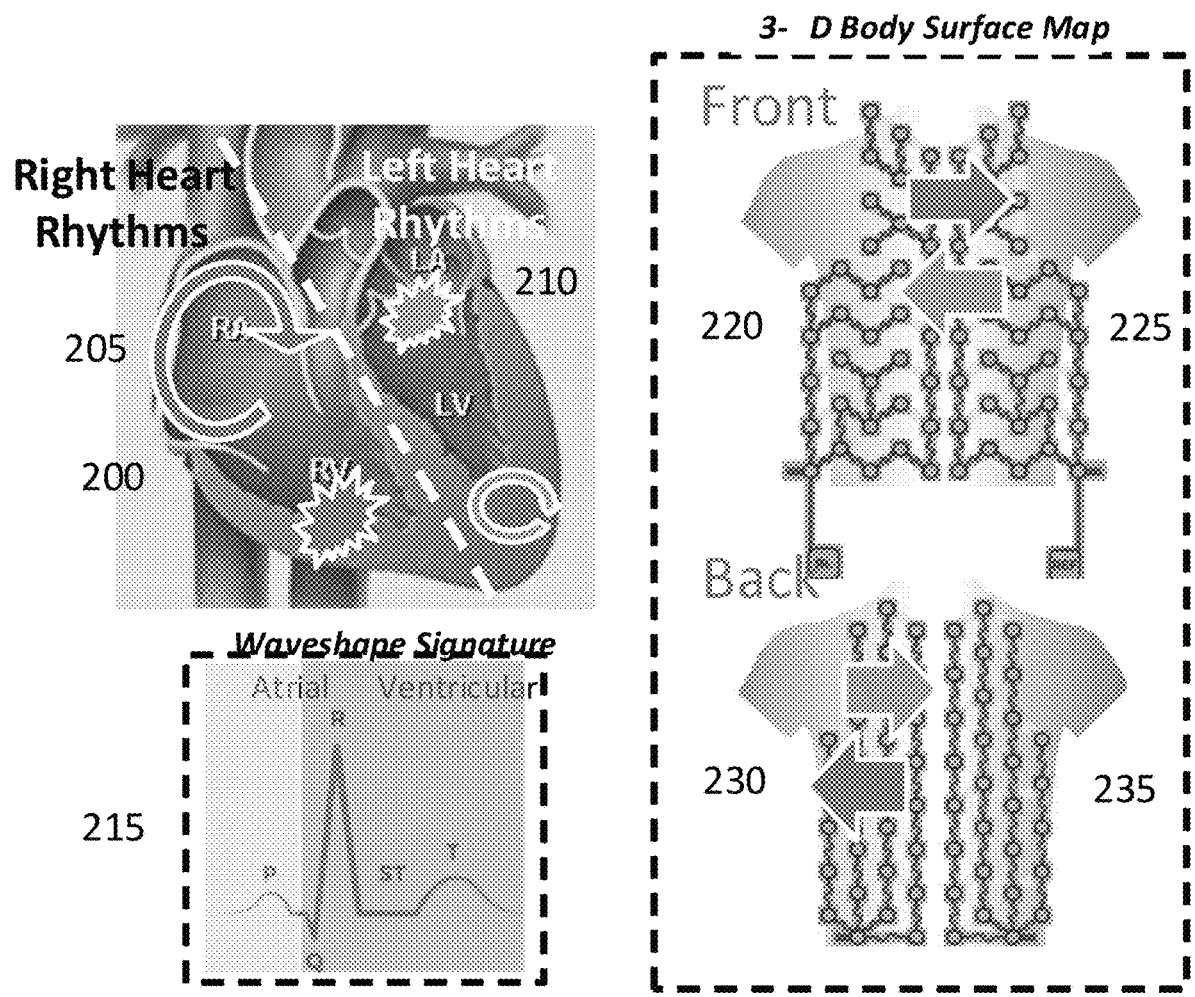
FIGS. 2A and 2B are conceptual diagrams illustrating a non-invasive body surface device for detecting a rhythm location (e.g., a heart rhythm location) of a subject, in accordance with one or more embodiments. Atrial fibrillation is shown.
Figure 2B:
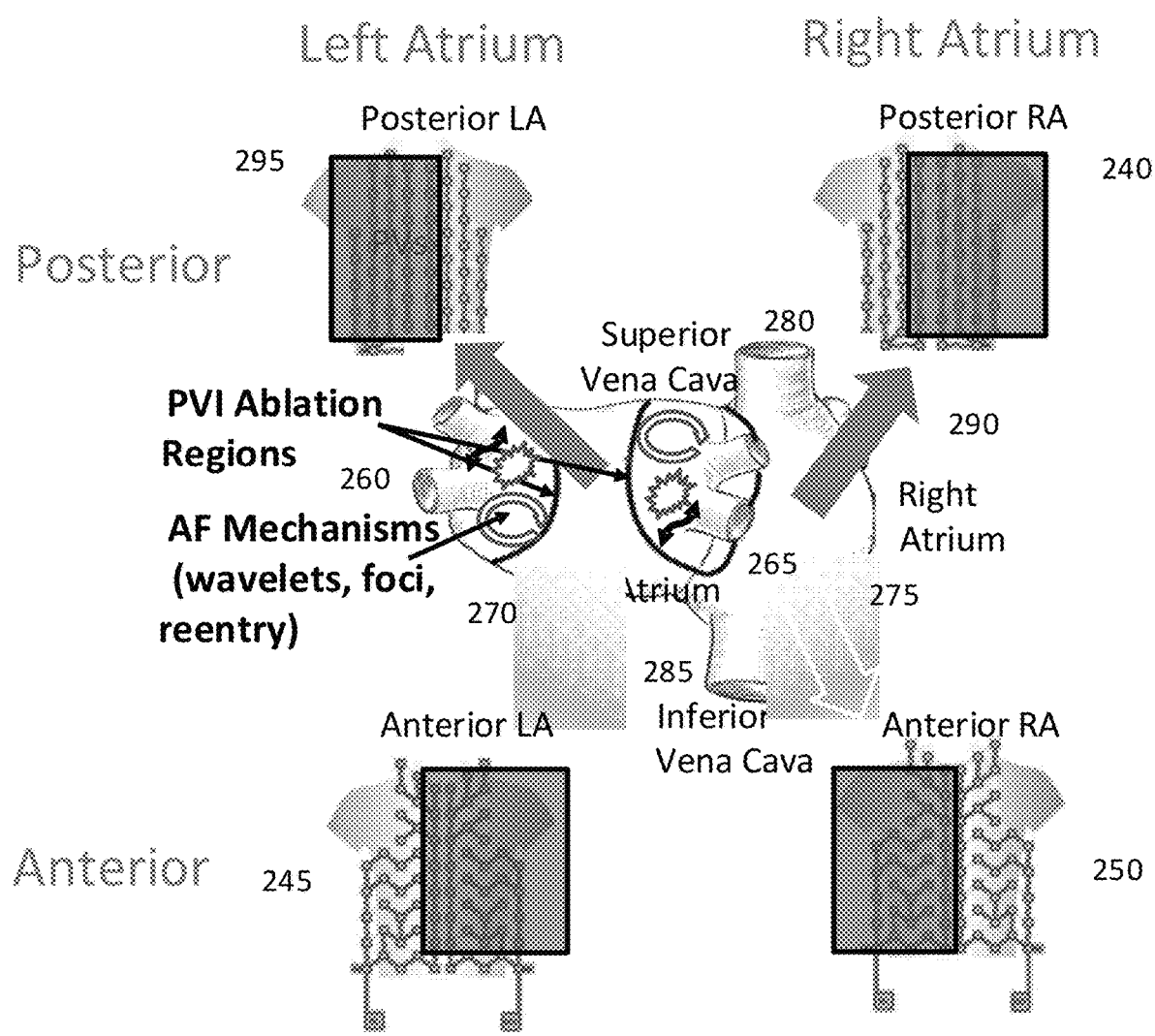

FIGS. 2A and 2B are conceptual diagrams illustrating a non-invasive body surface device 110 for detecting one or more locations of the heart that are associated with a heart rhythm disorder of a subject, in accordance with one or more embodiments. Those locations may be referred to as rhythm locations (e.g., a heart rhythm location), which may include locations of beats that initiate onset of a heart rhythm disorder and locations of sources for a heart rhythm disorder. While detecting heart rhythm conditions is discussed throughout this disclosure as an example remote rhythm evaluation process, similar principles may also be applied to other rhythm conditions in various embodiments. Sample non-invasive embodiment of a body surface device 110 on the chest is shown with projections from the right and left heart in FIG. 2A and pulmonary veins to different regions of the torso in FIG. 2B.

In some embodiments, the body surface device 110 includes a substrate comprising one or more regions. Each region configured to be in contact with one of the torso quadrants of the subject. The torso quadrants may be a right anterior, a left anterior, a left posterior, and a right posterior. In some embodiments, the substrate includes at least one region configured to be in contact with at least one of the torso quadrants. The body surface device 110 may also include one or more sets of electrodes. Each set of electrodes is carried in one of the regions of the substrate. The electrodes are configured to detect electrical signals generated by the heart of the subject. In some embodiments, a subset of the plurality of electrodes is configured to measure electromagnetic radiation including reflected light. The electrodes in each set, which are carried in the region configured to be in contact with the right anterior, the left anterior, the left posterior, or the right posterior, may be configured to detect the electrical signals for detecting a heart rhythm disorder respectively from the left atrium, the right atrium, the left ventricle, or the right ventricle. In some embodiments, the electrodes configured to cover one or more spatial projections of one or more areas of a heart projected on the body surface. In some embodiments, the electrodes configured to cover a spatial projection of at least a majority of a heart chamber projected on the body surface. In some embodiments, the body surface device 110 is configured to record from an area of less than half of the torso surface. In some embodiments, the body surface device 110 has an area of about or less than 100 $cm^2$. In some embodiments, the body surface device records from a surface area of less than 200 $cm^2$.

In FIG. 2A, the body surface device 110 analyzes electrical activity from the heart rhythm disorder 200 in form of reentrant 205 or focal electrical activity 210 or other patterns to identify the disorder's chamber of origin, which may involve analyzed metrics between body surface recordings in quadrants 220-235 or raw ECG recordings 215 for a plurality of beats. The patterns identified can be at the onset of a heart rhythm disorder, for instance to identify the location of trigger beats for atrial fibrillation (AF). The patterns can also be identified during heart rhythm disorder, such as to identify focal sources for focal atrial tachycardia, focal ventricular tachycardia or reentrant circuits for atrial flutter or for ventricular tachycardia. The analysis concludes with a rhythm location identified in right anterior 220, left anterior 225, left posterior 230 or right posterior 235, which may correspond to the arrhythmia origin in the left or right atrium, or left or right ventricle. In FIG. 2B, the body surface device 110 analyzes body surface regions selected to distinguish between left 260 and right 265 pulmonary veins, other parts of the left atrium 270, and areas of right atrium 275 such as superior cava vein 280, inferior cava vein 285 or right atrial appendage 290. The body surface device 110 analyzes the heart rhythm disorder from the ECG signals on the torso to indicate its region of origin, which may be on the left back 295, right back 240, front left 245 or front right 250 and may indicate the origin of the arrhythmia from specific regions of the atrial anatomy. In some embodiments, the body surface device 110 does not guide a catheter within millimeters of a specific site for ablation, but identifies spatial regions of interest where therapy may be effective. Ablation of this region should then be successful regardless if it is rotational, focal, repetitive of another configuration, low voltage or other.

In more details, the body surface device 110 is capable of identifying electrical activity patterns that includes centrifugal patterns, indicating single or repetitive focal activity (also termed a source), single or repetitive rotational patterns, which may indicate reentry or rotational activity or a 'rotor', other organized patterns which may be single or repetitive, such as partial rotations, or no apparent organization. In some embodiments, the body surface device 110 does not require the use of medical image data (CT or MRI scans) in order to perform this identification and analysis, although in some embodiments that data could be included in the analysis. For example, in some embodiments, a computing device, based on the signal data generated by the body surface device 110, may related a location of an electrical activity detected by the body surface device to a heart anatomy obtained from imaging by one or more of magnetic resonance imaging, computed tomography imaging or echocardiography. In other embodiments, anatomical information could be extracted from generic anatomic databases. These patterns are identified in form of sequences of local activation times, as sequences of instantaneous phase analysis, by Poincare or recurrence plots, by vectorial analysis or by other time-spatial analysis methods which may be familiar to one skilled in the art. This provides an analysis of the triggering or initiating region for a heart rhythm disorder, such as the first beats (focal beats with centrifugal emanation). If these sites lie repeatedly near the pulmonary veins and initiate AF, then this may be a good site for pulmonary vein isolation (PVI) therapy in that patient. Alternatively, if sites that trigger AF arise from sites that do not lie near the pulmonary veins, then PVI may not be the optimal therapy in this patient. In some embodiments, the analysis is observational in the subject and the body surface device 110 does not assume nor require specific biological mechanisms such as AF drivers, AF sources, AF rotors, multiple wavelet reentry, multiple focal sources mechanisms related to fibrosis and so on.

Figure 3A:
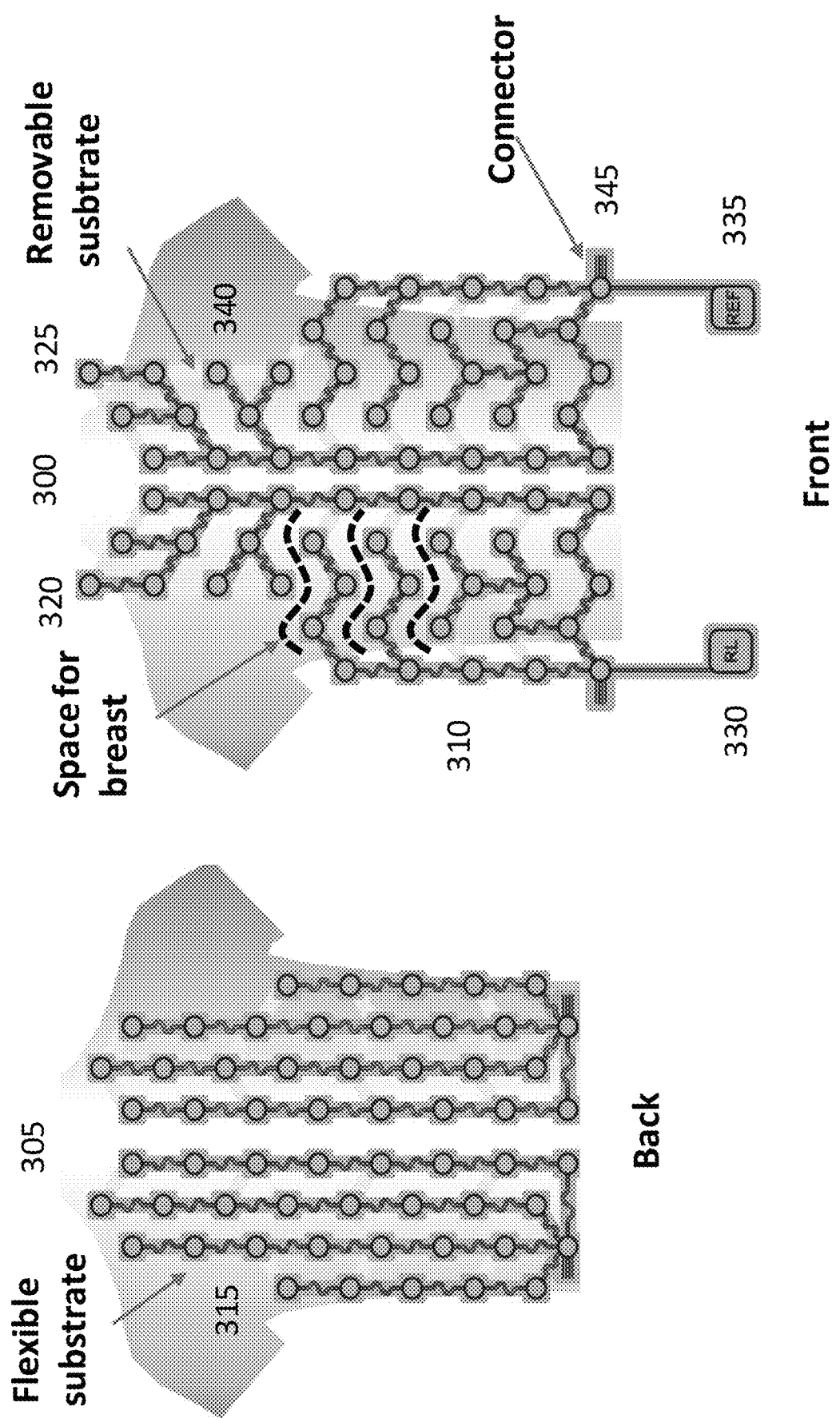
FIG. 3A illustrates an example embodiment of a full-torso body surface device, in accordance with one or more embodiments.

FIG. 3A illustrates an example embodiment of a body surface device 110. The designs in FIG. 3A are for full body torso recordings, but other embodiments in FIG. 3B include devices designed to capture signals from the left versus right portions of the heart, or the pulmonary veins versus other regions of the atria. In some embodiments, the body surface device 110 may be large enough to cover the body torso projection of a majority of a heart chamber, including left or right atria, or left or right pulmonary vein antra, or left or right ventricles, or right ventricular outflow tract, or pulmonary artery or left ventricular outflow tract or aorta. In some embodiments, the device will cover a lower torso or abdominal projection to assess activity near the renal arteries which can be targets for ablation. The configuration of electrodes can be in square grids, so that electrical propagation can be assessed in any orientation, or in a zig-zag pattern (FIG. 3A) or in a series of concentric circles or a spiral. Some of these patterns, such as the concentric circle, may be well suited to examine centrifugal activation from a focal sources, such as for focal atrial tachycardia or focal ventricular tachycardia. The number of electrodes will vary with the size of the body surface device and the biological application. The body surface device 110 in FIG. 3A includes tens of electrodes distributed on the front 300, back 305 and side 310 of the torso mounted on flexible material 315 with adhesive. An alternative design uses an etched flexible circuit. Electrodes are configured in one or more regions covering one or different parts of the torso. Patches contain ECG electrodes and may also contain reference electrodes for right arm 320, left arm 325, right leg 330 and left leg 335.

In some embodiments, the device or patch (if it is deigned to record from smaller regions than the entire torso) is constructed using flexible material to conform to torso shape and size, and could be also built with removable or breakable material to enable better shape adaptation 340. The thickness of the material may range from sub-millimeter to 5 mm depending on electrode construction and location, since some portions of the body may need more durable material. The connection between electrodes and recording device could be made through specific connector including several wires or printed circuits 345. Alternative, or additionally, a body surface device 110 may include a wireless transmitter (e.g., a WI-FI or BLUETOOTH transmitter) that transmits readings from the body surface device 110 directly to a computer.

Figure 3B:
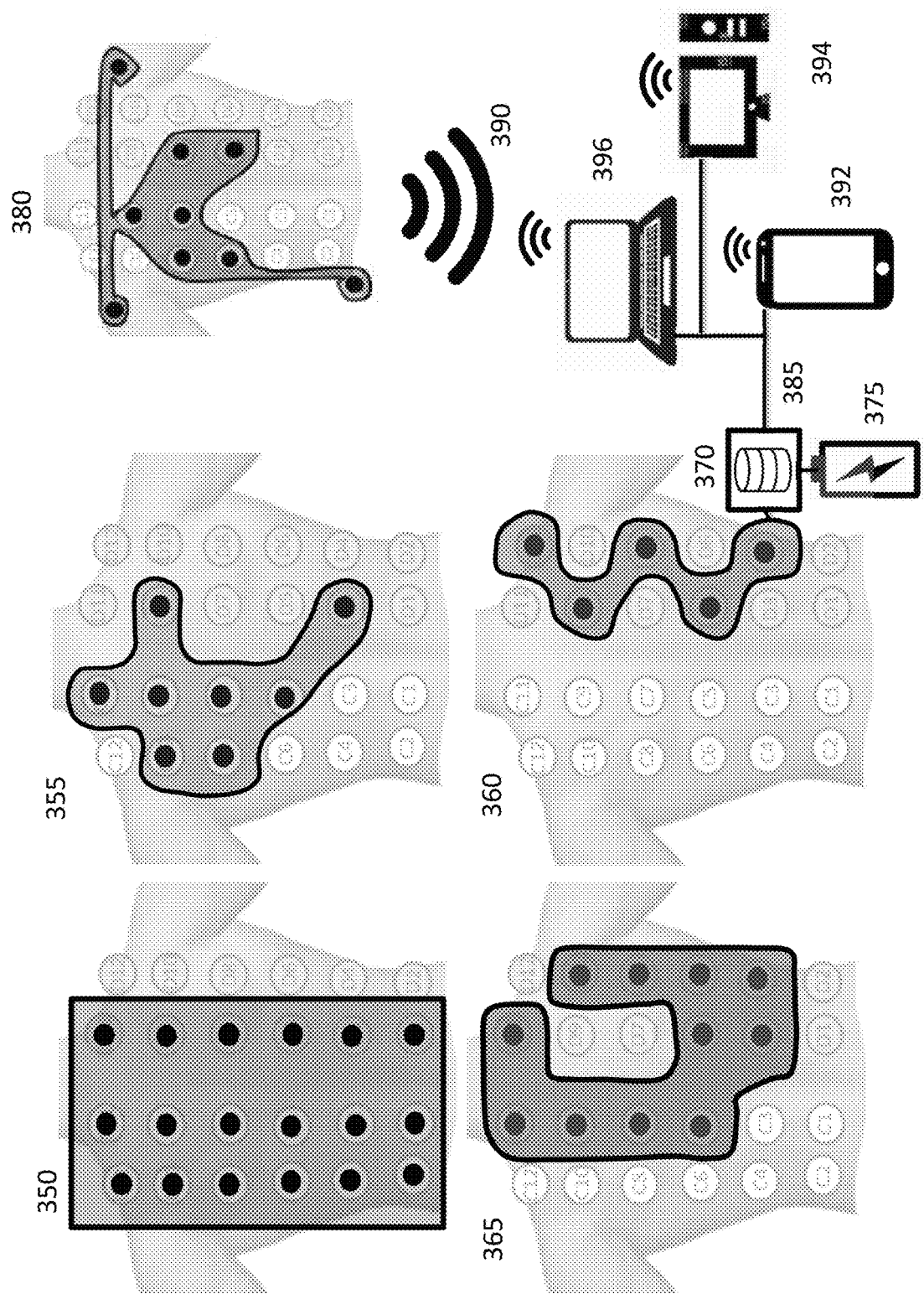
FIG. 3B illustrates an example embodiment of a targeted body surface device that is designed for focused regions of the torso, in accordance with one or more embodiments.

FIG. 3B illustrates an example embodiment of a body surface device 110 that is designed for focused regions of the torso. The body surface device 110 uses a limited number of electrodes in a configuration that will cover regions of interest for different specific applications. Electrodes can cover different regions of the torso, with a dense distribution 350 for high resolution of specific heart regions or sparse distribution 355 covering wider torso regions and reflecting activity from several heart chambers. Electrodes can cover single 360 or multiple 365 torso regions depending on the heart disorder suspected to be diagnosed. For AF, regions of interest could be right or left atrium, and pulmonary veins versus other atrial regions. For general arrhythmias, regions of interest will be right or left ventricle, or right or left atria. In some embodiment, the body surface device 110 may take the form of one or more patches. The patches can be connected to an external storing device 370 and battery 375 or it can contain the storing device 370 and battery 375. One or more device patches can be applied in non-contiguous body regions, linked by wire 385 or wirelessly 394 to a laptop 396, smartphone 392, computer 394 or another device. Patches contain ECG electrodes and may also contain reference electrodes for the right arm, left arm and left leg, as shown in patch 380. In some embodiments, the body surface device 110 is constructed using flexible material to conform to torso shape and size, and could be also built with removable or breakable material to enable better shape adaptation. The connection between electrodes and recording device could be made through specific connector including several wires or printed circuits.

The body surface device 110 may be used for diagnosing triggering sites and source sites for electrical rhythm disorders to guide therapy. The device is capable of sensing electrical signals and determining multiple sites that may be operative in that patient. The device may take the form of a patch. The patch is of sufficient size and appropriate shape to encompass the signals that represent the heart rhythm disorder. The size, shape and location may differ for men and women. The patch comprises an array of electrodes configured to detect a plurality of electrical signals generated by a heart and one or more other sensors. A controller is configured to determine the location of a trigger or source region based on detected electrical signals detected by the array of electrodes. The controller is configured to locate these regions within the heart. The controller is further configured to instruct the operator to guide therapy to the trigger, source or other target region to treat the heart rhythm disorder. The body surface device 110 is wearable during daily activities.

Alternatively, or additionally, the body surface device 110 includes non-electrical sensors. Example embodiments include electromagnetic sensors for visible light, to provide photoplethysmography assessment of periodic fluctuations in blood flow, oxygenation or other composition. Some embodiments can sense near-infrared or infrared signals to identify blood flow or other thermal signatures of heart physiology. These embodiments may be useful for applications in the head, such as to identify increased blood flow over a seizure focus or tumor area. Some embodiments use this device with acoustic sensors to identify heart sounds which could be normal, elevated or reduced during heart rhythm disorders, or elevated in heart failure. Some additional heart sounds such as a third heart sound could be sensed in heart failure. Some embodiments use this device to listen to and quantify lung sounds from breathing. The device could be used to identify absence of sounds from sleep apnea or obstruction. The device may also be useful for assessing lung sounds during recovery from or worsening asthma, bronchitis or pneumonia. Such lung diseases could be caused by pollution such as from fires or industrial or automobile sources, or from infections including COVID19. Specific patterns of lung sound abnormality can be identified in each, which will be apparent to those skilled in the art. In some embodiments, a device with acoustic sensors could be used on the abdomen to sense bowel activity in patients with paralytic bowel after surgery (ileus), or with hyperactive bowel activity such as during irritable bowel syndrome or acute obstruction.

Example Signal Processing Pipeline

Figure 4:
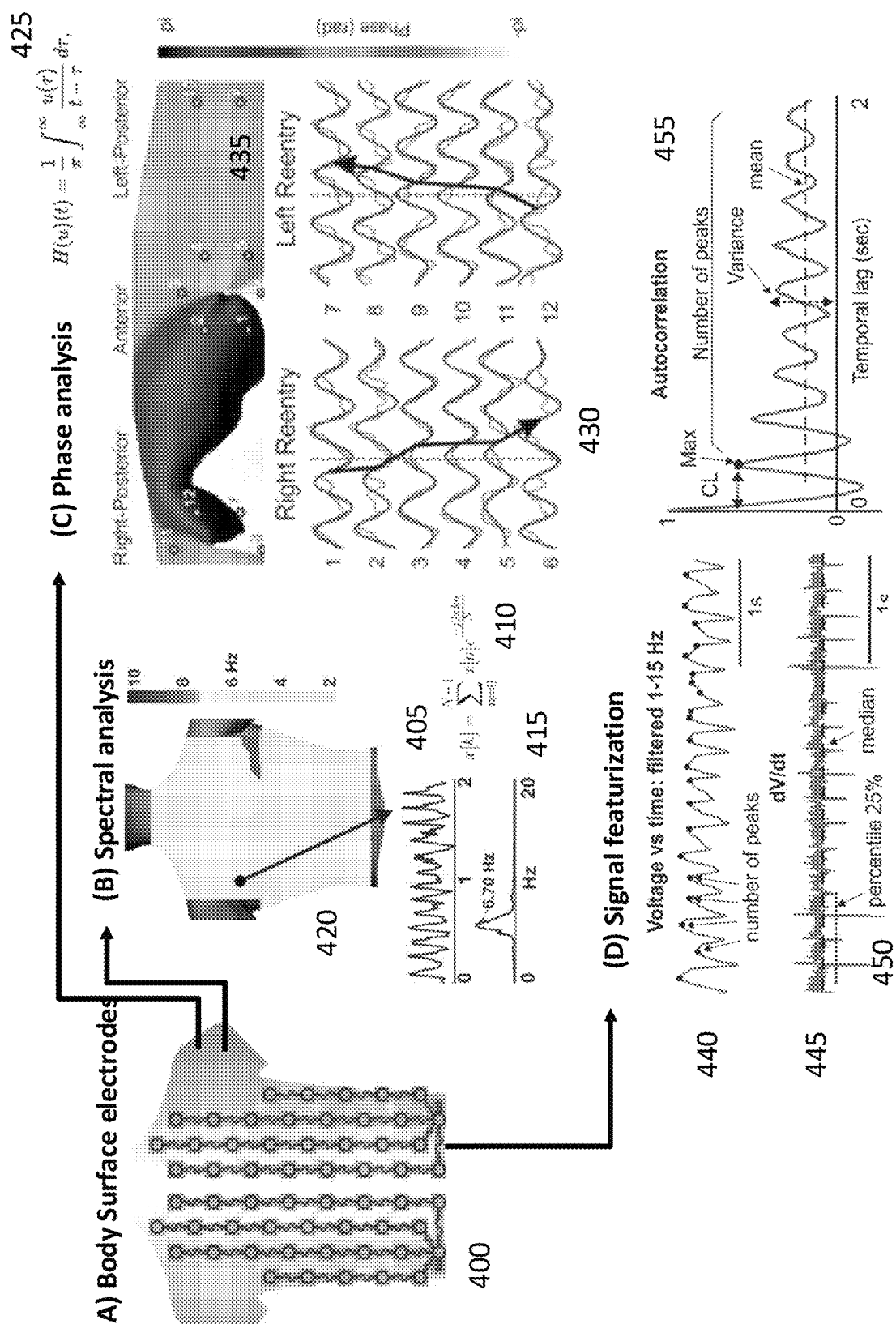
FIG. 4 is a conceptual diagram illustrating a body surface mapping method to enable several electrical pathways on the heart to be visualized on the body surface using signals from a body surface device, in accordance with one or more embodiments.

FIG. 4 is a conceptual diagram illustrating a mathematical body surface mapping method to enable electrical pathways on the heart to be visualized on the body surface using signals from a body surface device 110, in accordance with one or more embodiments. FIG. 4 is a graphical illustration of a data processing pipeline that may be performed by computing server 140 or any computing device for analyzing data collected from a body surface device 110. In some embodiments, the body surface device 110 does not require the use of medical image data (CT or MRI scans) in order to perform the cardiac electric characterization, although in some embodiments that data could be included in the analysis, extracted from the patient-specific MRI or CT scan or extracted from generic anatomic databases. The body surface device 110 provides sufficient precision to visualize whether target areas for ablation harbor critical areas for the arrhythmia. This may include detecting if these areas lie in versus right heart or, if in the atria, near the pulmonary veins or not. The body surface device 110 can provide this detection based only on the analysis of the surface electrocardiographic signals. FIG. 4 illustrates a full body torso embodiment, but this process may also be applied to a device examining smaller torso regions (e.g., a device shown in FIG. 3B). In some embodiments, the smaller region is large enough to cover the projection of the pulmonary veins onto the chest, such as for use in patients with atrial fibrillation in order to guide therapy by pulmonary vein isolation. In some embodiments, the smaller region is large enough to cover the projection of at least one heart chamber onto the body. That heart chamber is typically the chamber of origin of the heart rhythm disorder. One example of this is a focal atrial tachycardia from the right or left atrium, that may require specialized therapy that is quite different from therapy for AF or other complex arrhythmias Identifying that the source of the arrhythmia lies in the right atrium can eliminate the need for left atrial access via trans-septal cannulation or other procedures. Conversely, identification that the source lies in the left atrium can identify this need, so that the operator can plan for these components and a more lengthy procedure. Identifying the chamber of origin of an arrhythmia ahead of time is currently poor from the prior art. The electrocardiographic signals 400 from the patches electrodes of the body surface device 110 may be recorded and mathematically processed. One or more of these ECG signals may be processed individually or collectively. The number of electrocardiographic signals needed and their distribution on the torso surface may depend on the specific heart rhythm being studied or the chamber that can be mapped. In some embodiments, raw electrocardiographic signals with no filtering or the electrocardiographic signals after band-pass filtering or other types of filtering 405 may be used.

In some embodiments, filtering 405 may include high-pass filtering above 0.5 Hz to remove baseline oscillation or other artifacts, but others can be selected. In another embodiment, filtering 405 can include low-pass filtering to remove electrical noise or other artifacts. Filtering can include also narrow-band pass filtering at spectral band determined by features of the signal under analysis or other signals. For instance, some important features of AF in the frequency domain can be identified in bands of 0-20 Hz, such as the frequency of the main or secondary spectral contributions, their width and relative amplitude as well as the relative spectral content for certain frequency bands compared to the total spectral content. These features could be considered when selecting filters for signal acquisition. An embodiment could also use ventricular activity cancellation when the aim is to identify origin regions from the atrial chamber. In some embodiments, the ventricular cancellation algorithm is based on detection of the instant of ventricular depolarization using a combination of linear and non-linear filtering and identification of local maxima. The ventricular cancellation algorithm could be based on ventricular shape average and subtraction using one or more torso signals. The ventricular cancellation algorithm could be based on partial component analysis using different ventricular beats.

The computing server 140 may perform spectral analysis of the torso signals, using the Fast Fourier Transform 410, the Welch Periodogram, convolutional-based transform or the continuous wavelet transform. The spectral analysis could be also based on the combination of spectral transformations after different linear or non-linear filtering, such as band-pass filtering or Bottteron and Smith filtering. The spectral analysis could be used to detect the main spectral contribution 415 using the following formula:

$$DF = \vartheta(s_{ECG})|_{\vartheta(s_{ECG}) = max(\|\vartheta(s_{ECG})\|)}$$

In the above equation, DF is the main spectral contribution or Dominant Frequency, $s_{ECG}$ is the surface signal under analysis and $\vartheta(s_{ECG})$ represents the spectral transform by Fast Fourier Transform or Welch Periodogram. The computing server 140 may perform identification or other secondary spectral contribution using the local maxima of the spectral transform. The computing server 140 may perform the analysis of the spatial distribution of the DF values over the torso 420 in order to identify regions with the same or different values of DF. The computing server 140 may perform analysis of the phase of the surface signal 425, using the following or other formula:

$$phase(t) = arctan(imag(hilbert(s_{ECG}(t))), hilbert(s_{ECG}(t)))$$

In the above equation, phase(t) is the instantaneous phase transform of the signal under analysis $s_{ECG}$, and imag( ) and hilbert( ) represents the imaginary-part extraction and Hilbert transform functions respectively. The computing server 140 may perform the analysis of the phase from individual signals, by identifying the fiducial points such as local maxima or transitions from/to pi/−pi. The computing server 140 may perform the analysis of several instantaneous phase signals in spatial maps 430, using spatial interpolation of the phase signal in each instant and position to cover all the surface torso between electrodes 435. This spatial interpolation could be carried out using linear interpolation, cubic splines or other interpolation methods, and could be carried out without the use of torso anatomies and shapes extracted from medical image (MRI, CT) techniques. The computing server 140 may perform the analysis of the instantaneous phase maps through the identification of the phase transitions, that is, the lines in which the phase map transits from pi to −pi. The computing server 140 may perform the analysis of spatial phase singularities using the following formula:

$$\text{singularity}(t) = \oint_{0,D}^{2\pi} \text{phase}\left(s_{ECG}(t)_{x,y}\right)$$

In the above equation, the operator $\oint_{0,D}^{2\pi}$ represents the spatial integral over a circle with radius D and $s_{ECG}(t)_{x,y}$ is the electrocardiographic signal at interpolated coordinates X and Y. The computing server 140 may perform identification of instants and points in which the singularity(t) provides values different to 0 and summarize and cluster them to measure the spatial and temporal complexity of heart arrhythmia. The computing server 140 may perform the analysis of the temporal features of the electrocardiographic surface signal as the number of local maximal after band-pass filtering 440. The computing server 140 may perform the analysis of the first and second derivatives of the torso surface signal 445 in order to identify their percentiles and quartiles 450. The computing server 140 may perform autocorrelation analysis of the electrocardiographic surface signals 455.

In some embodiments, the computing server 140 may identify focal beats, such as from rapidly firing regions near a pulmonary vein. Focal beats could be identified in body surface potentials and/or their derivatives, characterizing atrial or ventricular complexes with specific traces that represent a focal beat origin. When analyzing a series of signals, a sequence of activation emanating outwards from a point would support a focal source. Other characteristics can be analyzed based on the relative temporal or spatial position of tracings, such as the frequency of focal activation, the size and shape of the region activated though the focal beat and the relative tridimensional (x,y,z) position and orientation of the focal site with respect to surface electrodes—in other words, does activation emanate from, to or parallel to the surface electrodes. Focal beats could also be identified using the phase transform applied to multiple electrocardiographic surface signals. Focal sources could be identified as regions and instants with expanding circles of constant phase values or with phase values different than the surrounding phase map points. Focal beats could be also identified using spatial and temporal derivatives of the electrocardiographic signals, such as the divergence, in order to identify regions with positive divergence values or sites in which the spatial and temporal derivatives indicates emanating potential sources.

In some embodiments, the computing server 140 may also identify repetitive activations which do not exhibit a focal or reentrant pattern, which has been proposed to drive some arrhythmias including AF. Identifying repetitive activations may be performed using spatio-temporal analysis such as Granger causality between electrocardiographic signals, in which strong causal relations between pairs of signals can be characterized and summarized in maps. Such maps can be then interpreted to identify emanating (outward) patterns, that is, regions from which the causal relations emerge, or as regions in which causal relations are reentrant, using divergence or rotational vectorial metrics or other techniques to analyze vectorial maps. Repetitive activations could be also identified in phase maps constructed from different electrocardiographic signals as singularity points, that is, regions and instants in which the phase map reflects increasing and circular distribution on phase values. Repetitive activations can also be identified in single or multiple electrocardiographic signals by the analysis of the potential series signals and/or their derivatives, characterizing specific atrial or ventricular complexes that present specific and repetitive signal traces. Finally, repetitive activation can be identified using correlation analysis of specific combinations of ECG signals at different locations over time. Analysis of repetitive activations could be carried out without the use of the torso anatomy and shape extracted from medical image techniques (MR, CT).

In some embodiments, the computing server 140 may calculate a cardiac output and determine whether the cardiac output is reduced. In response, the computing server 140 may send an alert that the cardiac output is reduced.

Example Process for the Personalized Classification of Rhythm Location

Figure 5A:
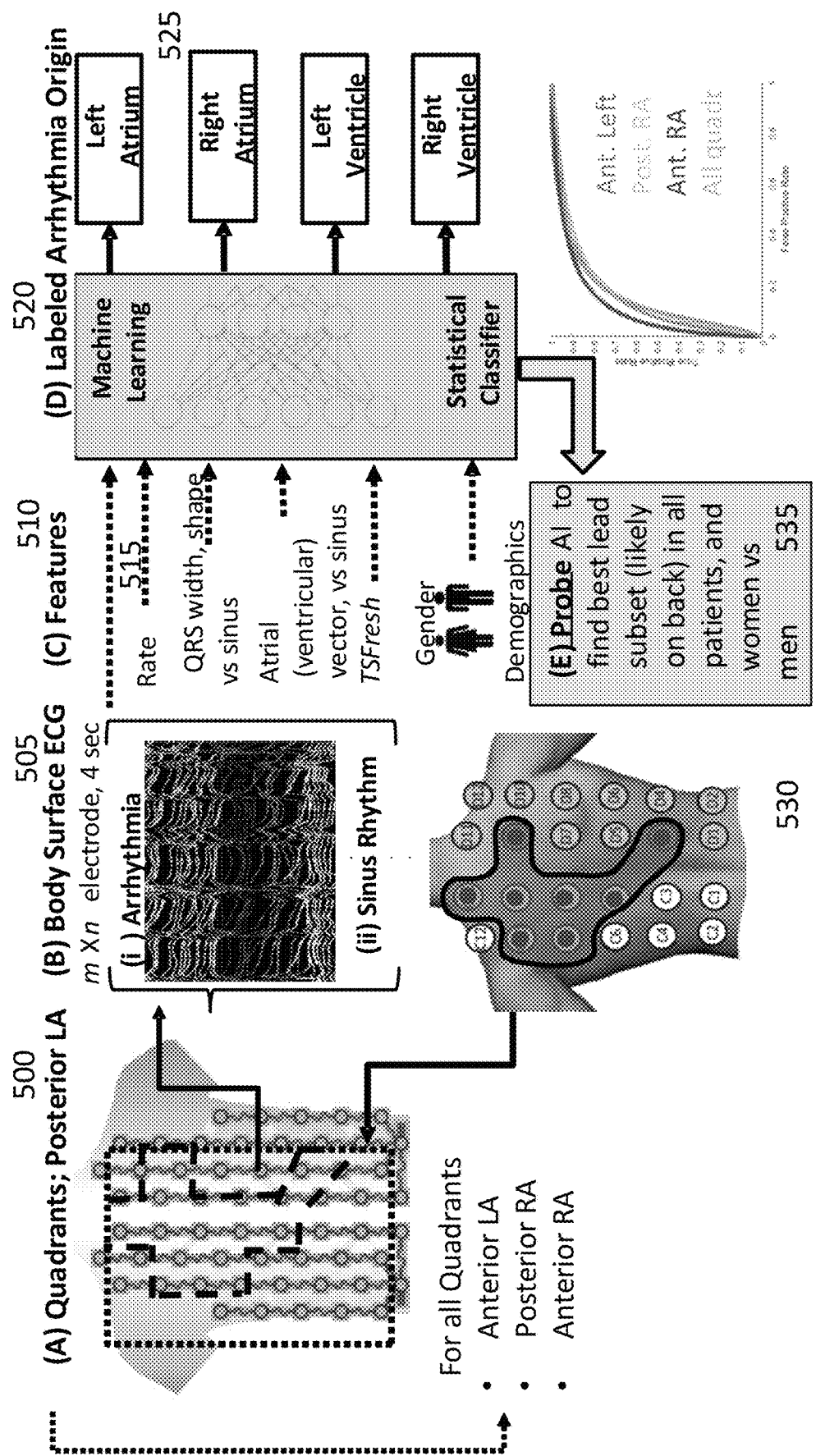
FIG. 5A is a diagram illustrating an algorithm process to classify locations of abnormal rhythm to be located inside the heart using the body surface recording alone and/or intracardiac signals from a device, in accordance with one or more embodiments.

FIG. 5A is a conceptual diagram illustrating an algorithm process to classify rhythm locations from the body surface recording signals generated by a body surface device 110, in accordance with one or more embodiments. FIG. 5A is a graphical illustration of an inference algorithm that may be performed by computing server 140. The embodiment shows the development of signatures of a rhythm disorder which can be used to classify the rhythm, or identify special regions and/or special times within the rhythm disorder. The signal data used in FIG. 5A may be a version of signals generated by the body surface device, such as the raw signals or signals that are processed by the pipeline illustrated in FIG. 4. The process in FIG. 5A may be used to identify the location of rhythm to classify right or left atrial or right or left ventricular origin. This can be structured to separate pulmonary vein or non-pulmonary vein regions for atrial fibrillation one embodiment. Similar algorithmic processes may be for other types of rhythm disorders that are not related to hearts, such as for seizure disorder in the brain, activity in the gastrointestinal tract, or nerve firing in a portion of the body in neurological illness.

Classification can either be based on a combination of raw voltage-time series data 505 and features of the raw voltage-time series 510. Featurization of data can be used to separate supraventricular and ventricular arrhythmias, and their chamber of origin. This featurization could include spectral and phase analysis in individual and collective surface signals, as well as other features extracted from the temporal signal domain as the number of local maxima, cycle length, percentiles, amplitudes, variance, autocorrelation measures or entropy, among others. With respect to rate 515, in some embodiments, basic rules are used to separate tachycardias (rate >100/min), isolated premature beats (atrial or ventricular; isolated rate >100/min) or bradycardia (rate <60/min). These categories may be used to automatically separate beat categories for analysis. This automatic separation may be carried out using features extracted from the surface signals such as autocorrelation, dominant frequency, cycle length or other methods. Atrial versus ventricular activity are separated by established rules, to separate supraventricular from ventricular tachycardias. Secondary analyses are performed for the ventricular and the atrial electrical activity.

Directional information from activity maps and others signal and features are collected within or between quadrants of the torso. This feature separates left-to-right versus right-to-left vectors, and also anterior-to-posterior versus posterior-to-anterior vectors. Directionality is derived mathematically from apparent conduction velocity at each body surface electrode as path length (inter-electrode distance) divided by activation time, identified in the instantaneous phase or as local maxima or minima. The activation time field represents the projection of the wavefront velocity vector on the torso and allows to identify the propagation direction as the maximal gradient direction on the activation field with the following formula:

$$\text{direction}_{x,y}(t) = \left( \frac{\partial \text{act}(t, x, y)}{\partial x}, \frac{\partial \text{act}(t, x, y)}{\partial y} \right)$$

where act(t,x,y) represents the activation field function in space (x,y) and time (t) and direction$_{x,y}$(t) is the gradient of the vector field at positions X and Y for the instant t. The path of slowest conduction is in the direction of the outward unit normal of the advancing wavefront, and points outwards the initiating region.

As shown in FIG. 5A, the computing server 140 may use machine learning or statistical models 520 to analyze data from the voltage-time series, any of the extracted features, as well as clinical and demographic and other information from the patient 105 under study. The models are designed to provide an estimate of the origin of the arrhythmia which can be left or right side of the heart or ventricles/atrium 525. This classifier can be also be used to identify the best subsets of electrodes able to identify the origin of the arrhythmia with a number of electrodes 530 based on an analysis of the Receiver Operating Curves, accuracy or other coincidence metrics of different electrode configurations 535.

One or more supervised machine learning and statistical methods can be used to predict the arrhythmia origin including but not limited to neural networks, convolutional neural networks, recurrent neural networks, support vector machines, decision trees, discriminant analysis, naive bayes, and others. The input to the machine learning algorithms can be the voltage time-series data or features derived from the raw voltage time-series such as the aforementioned features. The output of the machine learning algorithms can be two-class (binary), multi-class, univariate, multivariate, or a combination of different output types. Unsupervised learning algorithms can also be used to featurize and cluster similar data together in case labels are missing. Unsupervised algorithms include k-means, principal component analysis, singular value decomposition, autoencoders, or other methods. Semi-supervised machine learning algorithms, which combine concepts from both supervised and unsupervised learning, can also be used when some data is missing labels. In semi-supervised algorithms, labeled data are used to pseudo-label unlabeled data and to improve the machine learning performance. Once a machine learning model is trained, the model is probed 535 to better understand what types of data inputs are most important for each classification or prediction.

In some embodiments, the computing server 140 or local device (e.g. Physician device 132 or other computing device) may use one or more explainability (or interpretability) techniques. Local Interpretable Model-agnostic Explanations (LIME) can be used to explain predictions by altering the input and observing how the output changes. LIME can be used for 1-dimensional data such as the ECG or electrical signals from within the heart (electrograms), numeric features or images. SHAP (Shapely Additive exPlanations) uses concepts from Cooperative Game Theory and local explanations, where an input or a feature is replaced by a random value from the data and the difference in predicted output is measured. Another approach is Gradient-weighted Class Activation Mapping (Grad-CAM), which identifies the most critical nodes as the largest output weights multiplied by output's backpropagated gradients with respect to the final convolutional layer.

In one embodiment, the system uses explainability tools to identify the optimal leads 535. One of the methods above, such as LIME or Shapley value can be used to indicate which portions of the input data set (input vector) are most important to the classification of heart location, and hence which electrodes are the most important and should be part of the recording patch on a portion of the body torso. This can be personalized for men versus women, for persons with different body torso shapes such as extreme obesity or very tall individuals, and even for a specific individual.

This latter individualization of torso lead positioning can be used to track an arrhythmia over repeated recordings, and identify if instances represent the same or a different rhythm. This is particularly useful for conditions such as atrial fibrillation, atypical atrial flutter, focal atrial tachycardia, focal ventricular tachycardia or reentrant ventricular tachycardia. In these conditions, it is often unclear if clinical episodes represent the same arrhythmia or other arrhythmias potentially from different locations. This has great impact over the approach to therapy.

In another embodiment, analyses specify features that should or should not be part of the model including spatial domains in images (e.g., size of an atrial driver region, or ventricular conduction velocity, or spatial extent of fibrosis in the human heart) enabling tailored interpretation to domain electrophysiological "concepts" to ensure that models do not converge on irrelevant concepts. An example of this is the Testing with Concept Activation Vectors (TCAV) approach. This can examine specific features that should or should not be part of the model (e.g., size of AF driver regions), enabling the computing server 140 to test explainability analyses to accepted "concepts" and thus ensure that the solution is realistic and plausible. As another example, the prediction of an AF outcome (e.g., success or failure of ablation) can be tested by an interpretable model, e.g., presence of fibrosis near the right atrium. This approach attempts to ensure that numerical models are relevant to predictions, and models do not converge on irrelevant concepts. Explainable features predicting outcome will thus be identified quantitatively. The clinical rationale can subsequently be added via domain knowledge, e.g., the determination that obesity predicts negative outcomes from ablation or drug therapy, while hair color predicting positive outcomes may not. Data on populations in whom class IC anti-arrhythmic drug (AAD) may be used can also be included.

In some embodiments, machine learning models 520 receive data from the body surface device 110, which may take the form of non-invasive ECG patches. The data may be raw or featured. The machine learning model 520 maps the data to the anatomical location in the heart as well as predicting a ranked list of therapies showing which is most likely to benefit the patient 105. This prediction can be performed without the use of patient-specific anatomies extracted from medical image techniques (MRI, CT). The model can also utilize other data streams that were recorded from other sensors or databases. The input data streams can be used in their raw type, preprocessed, or featurized to improve model predictions.

In various embodiments, a wide variety of machine learning techniques may be used. Examples include different forms of supervised learning, unsupervised learning, and semi-supervised learning such as decision trees, support vector machines (SVMs), linear regression, logistic regression, Bayesian networks, and genetic algorithms Deep learning techniques such as neural networks, including convolutional neural networks (CNN), recurrent neural networks (RNN), long short-term memory networks (LSTM), and auto-encoders may also be used. For example, the machine learning model 520 shown in FIG. 5A may apply one or more machine learning and deep learning techniques.

In various embodiments, the training techniques for a machine learning model may be supervised, semi-supervised, or unsupervised. In supervised learning, the machine learning models may be trained with a set of training samples that are labeled. For example, for a machine learning model trained to the known rhythm location based on sensor signals. The labels for each training sample may be binary or multi-class. In training a machine learning model for identifying rhythm location, the training samples may be signals of patients diagnosed with known rhythm disorders at known locations. The label may be the rhythm locations of those patients. In another embodiment, the label may be the type of rhythm condition, to differentiate atypical atrial flutter from atrial fibrillation, for instance. In some cases, an unsupervised learning technique may be used to identify samples which are similar to each other and hence those that are different. The samples used are not labeled. For example, patient data without determination of the actual rhythm locations may be used in unsupervised learning. Various unsupervised learning techniques such as clustering (k-means and other clustering techniques) may be used. In some cases, the training may be semi-supervised with the training set having a mix of labeled samples and unlabeled samples.

A machine learning model may be associated with an objective function, which generates a metric value that describes the objective goal of the training process. For example, the training may intend to reduce the error rate of the model in predicting the rhythm locations. In such a case, the objective function may monitor the error rate of the machine learning model. Such an objective function may be called a loss function. Other forms of objective functions may also be used, particularly for unsupervised learning models whose error rates are not easily determined due to the lack of labels. In the prediction of rhythm locations, the objective function may correspond to the difference between the model's predicted rhythm locations and the manually diagnosed rhythm locations in the training sets. In various embodiments, the error rate may be measured as binary or categorical cross-entropy loss, L1 loss (e.g., the sum of absolute differences between the predicted values and the actual value), L2 loss (e.g., the sum of squared distances), or others. A combination of loss functions may be used in one machine learning model. L1 and L2 may also be used as regularization techniques as well to prevent overfitting.

Figure 5B:
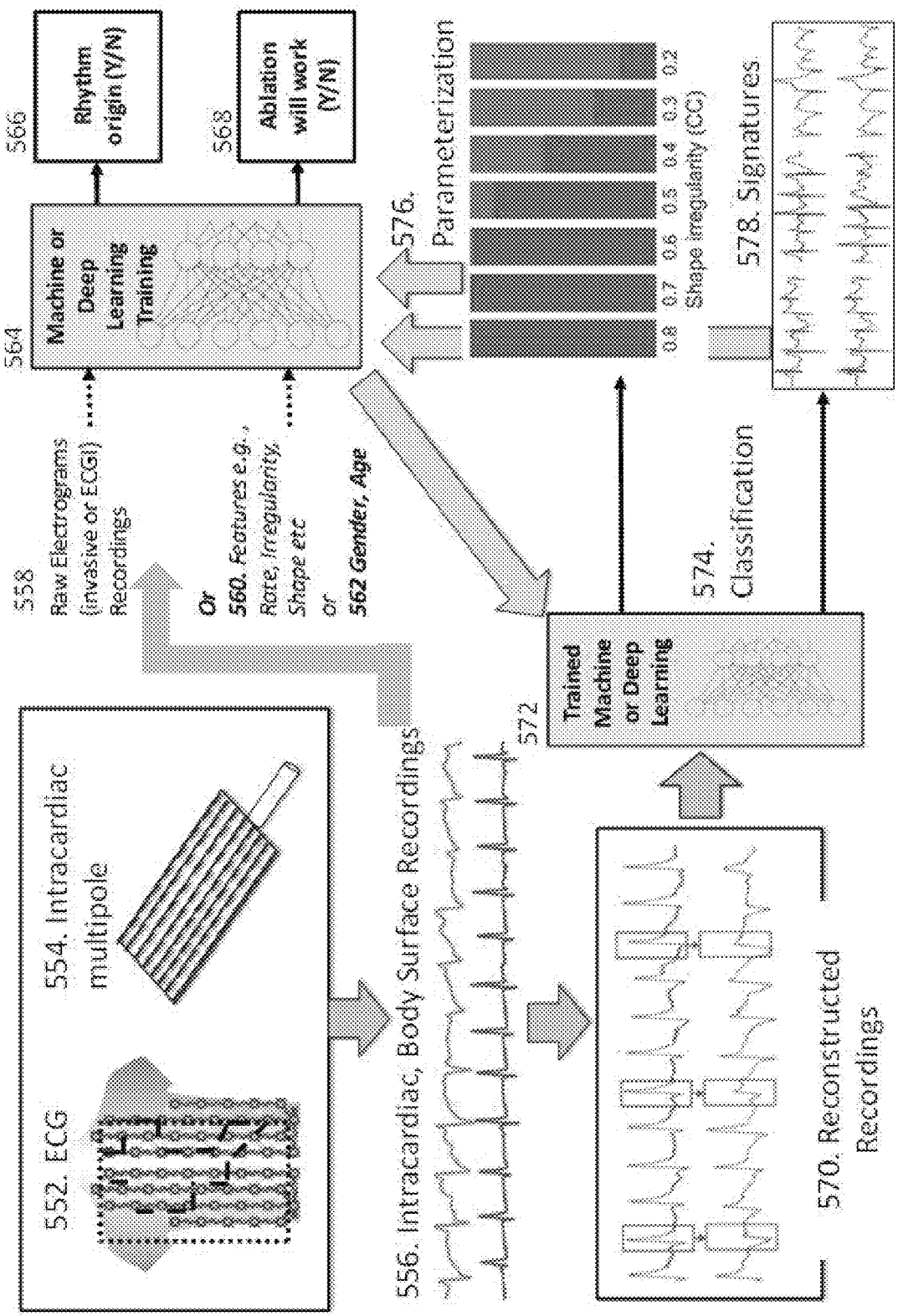
FIG. 5B is a diagram illustrating an algorithm process to extract specific rhythm signatures in the body surface alone and/or intracardiac signals using reconstructed signals, and an algorithm able to use these specific signatures to refine the rhythm identification, in accordance with one or more embodiments.

FIG. 5B is a diagram illustrating an algorithm process to extract specific rhythm signatures in the body surface and/or intracardiac signals. The embodiment shows the development of signatures of a rhythm disorder which can be used to classify the rhythm, or identify special regions and/or special times within the rhythm disorder. These special times and/or regions can be treatment targets. FIG. 5B illustrates feature identification and classification that may be performed by computing server 140. The signal data used in FIG. 5B may be a version of signals generated by the body surface device, such as the raw signals or signals that are processed by the pipeline illustrated in FIG. 4, or may be signals recorded by intracardiac catheters.

FIG. 5B also shows reconstructed signals and an algorithm that is applied to these specific signals to create fingerprints or footprints or signatures of the rhythm. The signature may classify the heart rhythm disorder, such as atrial fibrillation or atrial tachycardia or atrial flutter or ventricular tachycardia and so on. The process in FIG. 5B may be used to refine the identification of the location of rhythm to classify right or left atrial or right or left ventricular origin. This can be structured to identify pulmonary vein from non-pulmonary vein regions for different embodiments. This can be useful to separate conditions such as atrial flutter from fibrillation, which guides therapy. This can also be useful to separate different forms of atrial fibrillation, such as those which can be treated by pulmonary vein isolation compared to forms that require therapy at additional areas outside the pulmonary veins. Similar algorithmic processes may be for other types of rhythm disorders that are not related to hearts, such as for seizure disorder in the brain, activity in the gastrointestinal tract, or nerve firing in a portion of the body in neurological illness.

The signature may also identify a signal type that is a treatment target for the heart rhythm disorder, such as a region of slow conduction, of a viable channel of tissue within scar, or fractionated signals, of high rates, of source or driver activity and so on. The signal signature may or may not be clear from analyses of the time-domain characteristics of the signal, such as amplitude, rate or shape. The signal signature may or may not be clear from analyses of the frequency domain characteristics of the signal, such as frequency, harmonics or phase. The signature may extend to signals from neighboring electrodes to form a preferred spatial region or cluster.

Data acquired from surface electrodes 552 provide raw signals or signals that are processed by the pipeline illustrated in FIG. 4, as well as intracardiac electrical recordings from multipolar catheters 554, could be used individually or in conjunction giving signals 556 to train classifiers able to identify the rhythm origin 566 or to predict the ablation success in a specific patient 568. These classifiers could use a variety of input data to perform the classification of the raw or processed signals 558, or features extracted from these signals 560 as explained in FIG. 5A, or patient demographics 562 such as sex or age.

For a catheter within the heart 554, contact can be enhanced using a variety of compliant materials, depending on the intended location within the organ of interest. One type of catheter uses a conformable chamber filled with cryo-solvent for mapping and ultimately cryoablation, in which the therapy device adheres to tissue during energy delivery for rapid, accurate and safe ablation. This can be effective to ablate sources of AF and atrial tachycardias in the heart, and seizure foci in the brain. One embodiment uses a nitinol frame upon which electrodes are mounted. The device thickness should be sufficient to support the array of electrodes against the contours of the tissue, while being flexible enough to be collapsed and folded into a sheath. An exemplary thickness range would be on the order of 0.10-4.0 mm but may vary depending on the components and features incorporated into the device. In some embodiments, a range of 0.75-1.0 mm will be flexible enough to conform to the heart chamber while providing enough support for the electrode material. In another embodiment, a range of 2-3 mm will provide greater structural stability for use outside the heart, such as for cardiac surgical applications, or for the ventricle which has a greater range of contractile motion.

In order to refine the classifier 564 performance, reconstructed recordings 570 from the body surface or intracardiac catheters could be used. These reconstructed recordings could be body surface or intracardiac signals in which a specific characteristic is changed and varied. For instance, reconstructed recordings could be obtained by reconstructing body surface or intracardiac signals with varying shape or rate. Reconstructed recordings could be processed in the computer server 140. These reconstructed signals would compose a database in which one or more of these parameters is changed at a time, keeping all the rest as in the departing body surface or intracardiac signals. Reconstructed signals 570 could be then classified using the trained classifier 572 described in FIG. 5B in order to obtain the classification labels 574 for each of these reconstructed signals. These classification metrics 574 on reconstructed signals 570 could be then used to identify the response of the trained classifier 572 to each parameter used in the reconstruction 576 and the relationship between the parameter under study in the reconstructed signal and the rhythm classification or other classification under study. This parametric information 576 could be then used to refine the classifier 564 or to identify new features 560 used in the classifier. Classification metrics 574 on reconstructed signals 570 could be used to identify specific signal traces or signatures 578 that are specific for certain rhythms or diseases or other classification problems under study. These signal signatures 578 identified in body surface or intracardiac data can be used to refine the classification performance 564 by the identification of these signatures in signals under study using convolution, correlation or other metrics. Signatures 578 can be used to identify novel features 560 used by the classifier 564.

Figure 5C:
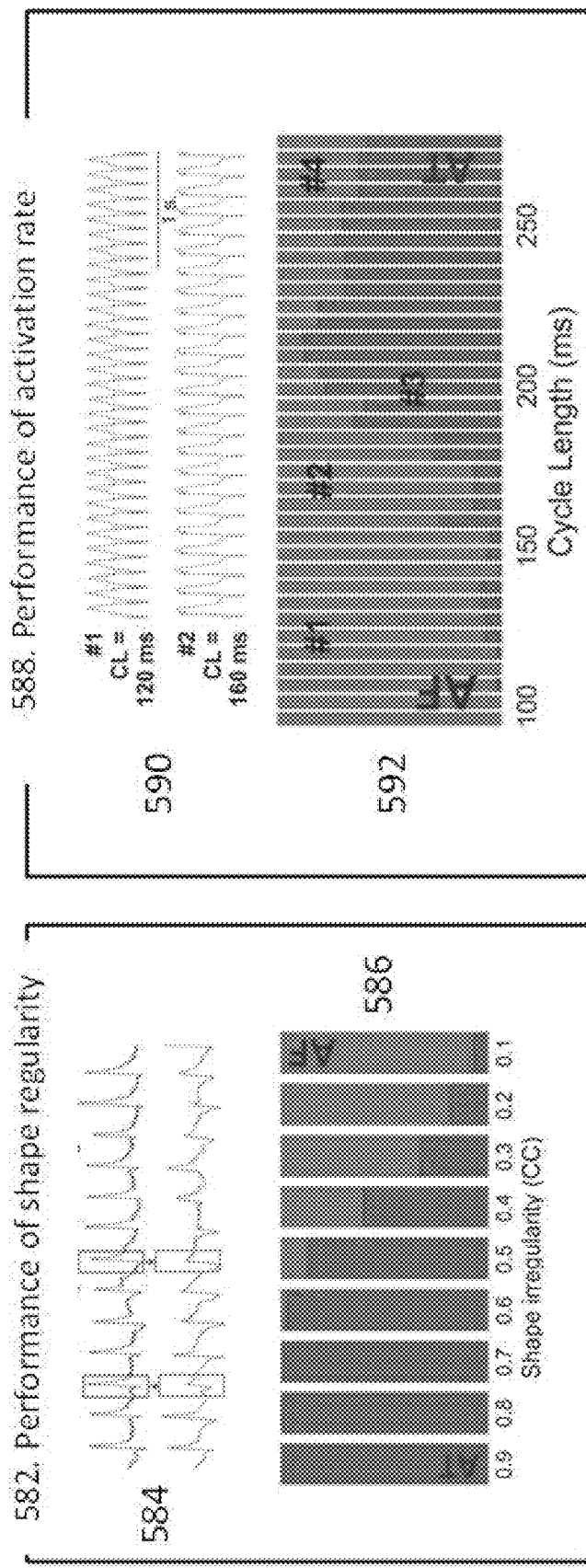
FIG. 5C includes diagrams illustrating the performance of rhythm signatures identified from the body surface and/or intracardiac signals to identify the condition of atrial fibrillation, in accordance with one or more embodiments.
Figure 5C:
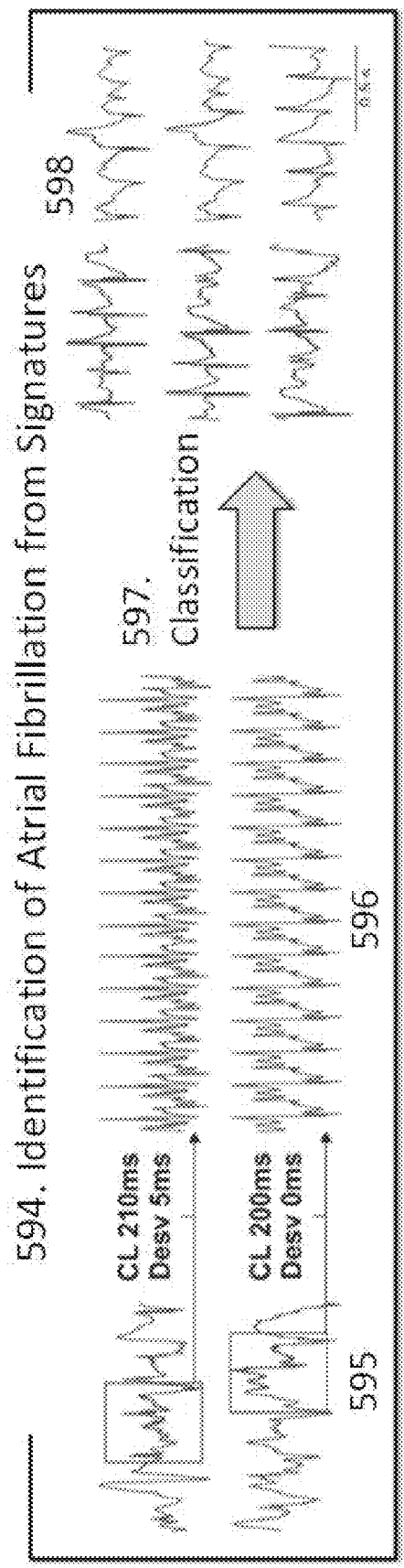

FIG. 5C are graphical illustrations of examples of rhythm parameters and signatures identified in body surface or intracardiac signals. FIG. 5C is a graphical illustration of parameters and signatures identification that may be performed by computing server 140 or a local device. The signal data used in FIG. 5C may be a version of signals reconstructed using body surface device, such as the raw signals, signals that are processed by the pipeline illustrated in FIG. 4, or signals recorded by intracardiac catheters. The examples in FIG. 5C may be used to refine the classifier of the location of rhythm to classify right or left atrial or right or left ventricular origin. This can be structured to identify pulmonary vein from non-pulmonary vein regions for different embodiments. Similar algorithmic processes may be for other types of rhythm disorders that are not related to hearts, such as for seizure disorder in the brain, activity in the gastrointestinal tract, or nerve firing in a portion of the body in neurological illness.

Parametric studies can be carried out using reconstructed signals 570. This can evaluate the performance of shape regularity 582 on classification, evaluated through reconstructed signals in which shape regularity is varied by replacing individual beats 584 in different proportions of each reconstructed signal. The predicted label for each reconstructed signal 586 classifies them into regular (such as Atrial Flutter) or irregular (such as Atrial Fibrillation) rhythms. This can identify the range of shape regularity which the trained classifier uses to perform classification. A different parametric study could be carried out to assess the performance of rate 588 on classification. Here, reconstructed signals have varying rate 590 for each reconstructed signal. The predicted label for each reconstructed signal 592 classifies them into regular (Atrial Flutter) or irregular (Atrial Fibrillation) rhythms, to identify the range of rate that the trained classifier uses to perform classification.

Specific signal signatures for each rhythms or other diseases 594 can be identified using reconstructed signals in which a single beat shape 595 is used repeatedly to reconstruct signals with regular shape but different rates and timing regularity 596. In some embodiments, classification 597 of the dataset of reconstructed signals with unique beat shape is used to identify those beat shapes 595 whose reconstructed signals had a predominant classification into one of the possible labels of the classifier. These individual beats 595 whose reconstructed signal present a predominant classification could be used as body surface or intracardiac electrogram signatures to refine the classification performance as described in FIG. 5B. In other embodiments, classification 597 of the dataset of reconstructed signals with unique beat shapes is used to identify specific regions and times for therapy. This may include targeting ablation to the site of that electrogram signature from beat shapes 595 or other parameters.

Figure 6:
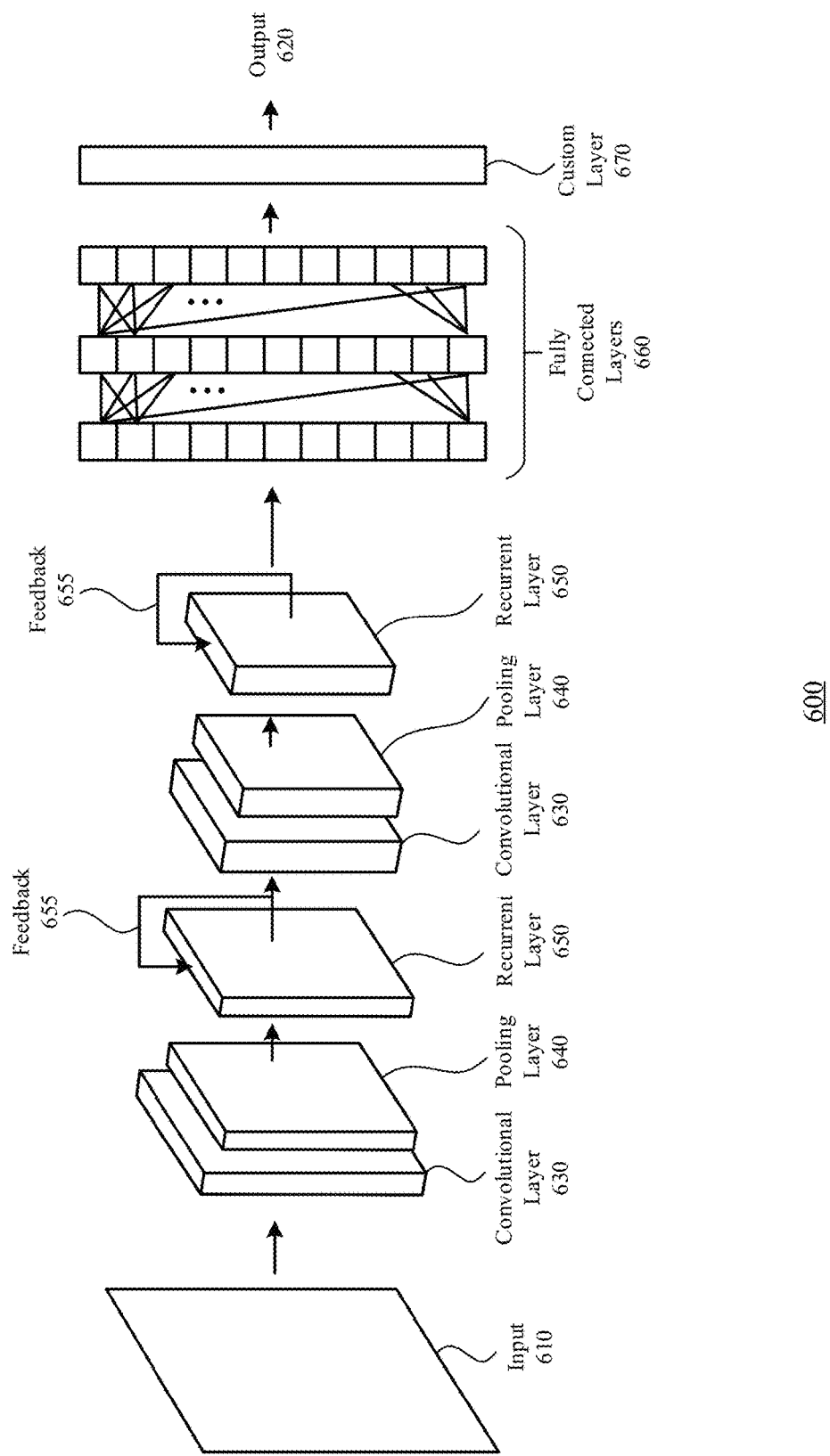
FIG. 6 illustrates a structure of an example neural network is illustrated, in accordance with one or more embodiments.

Referring to FIG. 6, a structure of an example neural network is illustrated, in accordance with one or more embodiments. The neural network 600 may receive inputs 610 and generate an output 620. While inputs 610 is graphically illustrated as having two dimensions in FIG. 6, the inputs 610 may be in any dimension. For example, the neural network 600 may be a one-dimensional convolutional network.

The neural network 600 may include different kinds of layers, such as convolutional layers 630, pooling layers 640, recurrent layers 650, full connected layers 660, and custom layers 670. A convolutional layer 630 convolves the input of the layer (e.g., a matrix of any dimension) with one or more weight kernels to generate different types of sequences that are filtered by the kernels to generate feature spaces. Each convolution result may be associated with an activation function. A convolutional layer 630 may be followed by a pooling layer 640 that selects the maximum value (max pooling) or average value (average pooling) from the portion of the input covered by the kernel size. The pooling layer 640 reduces the spatial size of the extracted features. In some embodiments, a pair of convolutional layer 630 and pooling layer 640 may be followed by a recurrent layer 650 that includes one or more feedback loops 655. The feedback 655 may be used to emphasize or account for spatial relationships of the features in an image or temporal relationships in sequences. The layers 630, 640, and 650 may be followed in multiple fully connected layers 660 that have nodes (represented by squares in FIG. 6) connected to each other. The fully connected layers 660 may be used for classification and object detection. In some embodiments, one or more custom layers 670 may also be presented for the generation of a specific format of output 620. For example, a custom layer may be used for image segmentation for labeling pixels of an image input with different segment labels.

The order of layers and the number of layers of the neural network 600 in FIG. 6 is for example only. In various embodiments, a neural network 600 includes one or more convolutional layer 630 but may or may not include any pooling layer 640 or recurrent layer 650. If a pooling layer 640 is present, not all convolutional layers 630 are always followed by a pooling layer 640. A recurrent layer may also be positioned differently at other locations of the neural network. For each convolutional layer 630, the sizes of kernels (e.g., 1×1, 1×2, 3×3, 5×5, 7×7, N×M, where N or M=1,2,3, . . . , etc.) and the numbers of kernels allowed to be learned may be different from other convolutional layers 630.

A machine learning model may include certain layers, nodes, kernels and/or coefficients. Training of the neural network 600 may include forward propagation and backpropagation. Each layer in a neural network may include one or more nodes, which may be fully or partially connected to other nodes in adjacent layers. In forward propagation, the neural network performs the computation in the forward direction based on outputs of a preceding layer. The operation of a node may be defined by one or more functions. The functions that define the operation of a node may include various computation operations such as convolution of data with one or more kernels, pooling, recurrent loop in RNN, various gates in LSTM, etc. The functions may also include an activation function that adjusts the weight of the output of the node. Nodes in different layers may be associated with different functions.

Each of the functions in the neural network may be associated with different coefficients (e.g. weights and kernel coefficients) that are adjustable during training. In addition, some of the nodes in a neural network may also be associated with an activation function that decides the weight of the output of the node in forward propagation. Common activation functions may include step functions, linear functions, sigmoid functions, hyperbolic tangent functions (tan h), and rectified linear unit functions (ReLU). After input is provided into the neural network and passes through a neural network in the forward direction, the results may be compared to the training labels or other values in the training set to determine the neural network's performance. The process of prediction may be repeated for other inputs in the training sets to compute the value of the objective function in a particular training round. In turn, the neural network performs backpropagation by using gradient descent such as stochastic gradient descent (SGD) or other optimization techniques to adjust the coefficients in various functions to improve the value of the objective function.

Figure 7:
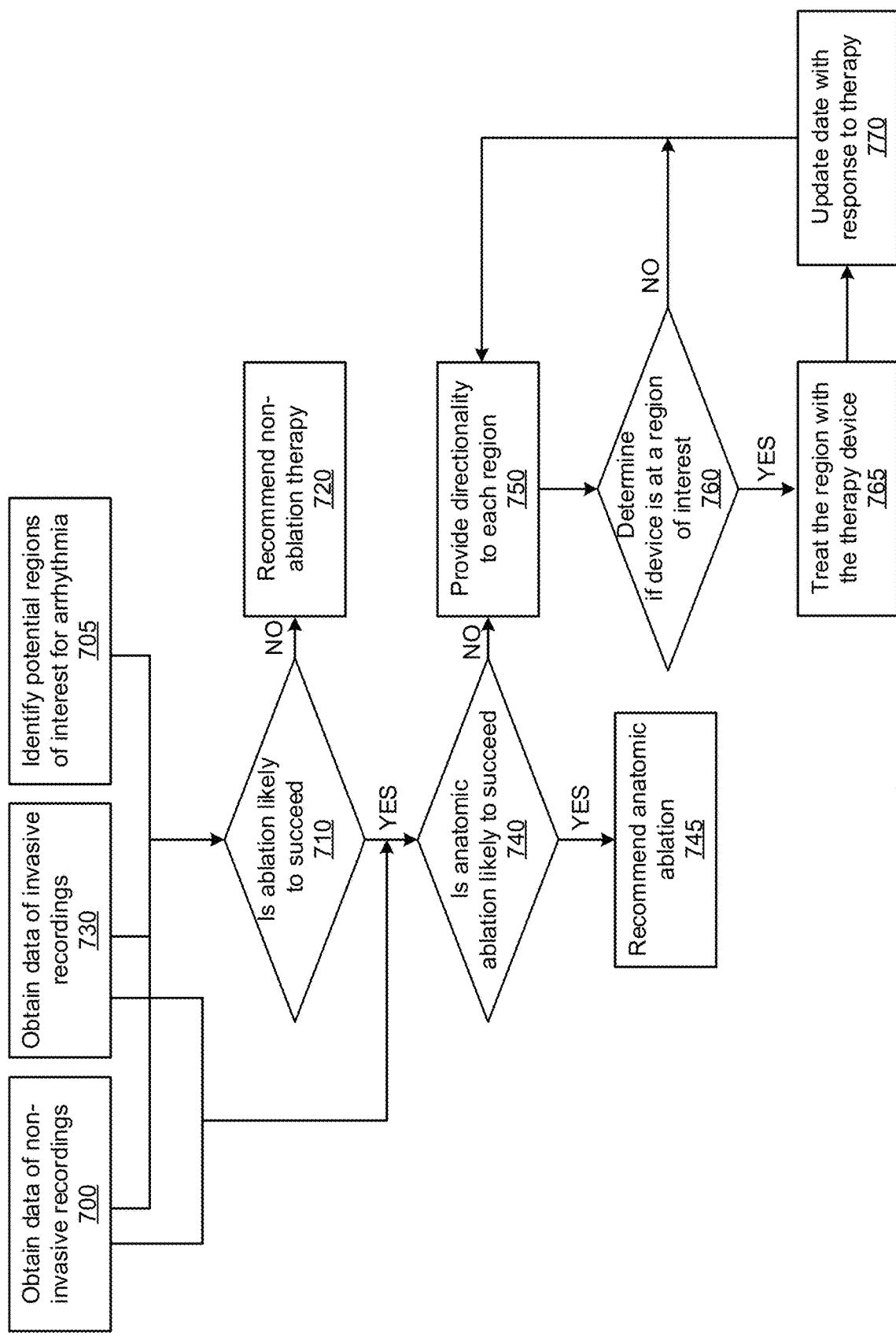
FIG. 7 is a flowchart depicting an example process that is executable by software algorithms for a computing system (e.g., computing server) to provide one or more arrhythmia management recommendations based on data collected by a body surface device, in accordance with one or more embodiments.

Multiple rounds of forward propagation and backpropagation may be performed to iteratively train a machine learning model. Training may be completed when the objective function has become sufficiently stable (e.g., the machine learning model has converged) or after a predetermined number of rounds for a particular set of training samples. The trained machine learning model can be used for performing various machine learning tasks as discussed in this disclosure. While the structure of a neural network is illustrated in FIG. 6, various other types of machine learning models, such as support vector machines, gradient boosted trees, random forests, may also be used in different prediction and analysis pipelines in this disclosure. The training techniques discussed in FIG. 6 may also be applied to those algorithms Example Therapy Recommendation Process FIG. 7 is a flowchart depicting an example process that is executable by software algorithms for a computing system (e.g., computing server 140) to provide one or more arrhythmia management recommendations based on data collected by a body surface device 110, an invasive catheter device 115, or both, in accordance with one or more embodiments. The software algorithm may be stored as computer instructions that are executable by one or more general processors (e.g., CPUs, GPUs). While computing server 140 is used to describe the process, the process may be performed by any computing device. The instructions, when executed by the processors, cause the processors to perform various steps described in the process. FIG. 7 illustrates one example to use patient data to manage and treat ablation procedures for atrial fibrillation. The patient data may include data on the activity patterns of the patient, which can be obtained from non-invasive tool 700 such as the body surface device 110 and/or invasive tools 730. In some embodiments, the computing server 140 receives only data from the non-invasive tool, such as the body surface device 110. Steps 700-740 are the first triage step, which identifies for a patient if empirical ablation will work. Steps 750-770 personalize AF mapping, map interpretation and ablation. In some embodiments, the computing server 140 may compute a predicted success score for a planned therapy for eliminating one or more regions that initiate an onset of the heart rhythm disorder or regions that maintain the heart rhythm disorder. For example, the planned therapy may be ablation as discussed in step 710 or non-ablation therapy as discussed in step 720.

In step 700, the computing server 140 receives non-invasive signals for AF. In some embodiments, the signals may include body surface potential maps (or potentially ECG imaging, ECGI) which may use up to hundreds of body surface leads (e.g., 252 leads). The signals may be raw signals or signals processed by the pipeline described in FIG. 4. In some embodiments, the body surface device 110 uses fewer ECG leads, as few as <20. The non-invasive inputs can also include the standard 12-lead ECG, a subset of the 12-lead ECG, magnetocardiography (MCG), non-invasive structural imaging and other features that can be obtained prior to the invasive study.

The process illustrated in FIG. 7 provides an option for disease prediction, in which the inventive technique identifies patient types (phenotypes) who do not manifest AF but who may be at risk for AF. This may be due to specific patterns of structural abnormality marked by low voltage or potentially abnormal on delayed enhanced magnetic resonance imaging. In this case, the computing server 140 provides for AF prediction. The server 140 may also provide for prediction of risk for ventricular tachycardia if activity is slowed in one region of the ventricle or if erratic patterns consistent with conduction through scar or "late potentials" can be identified even in sinus rhythm. This may be particularly useful in patients with prior structural heart disease including prior heart attack (myocardial infarction). This embodiment could also be used in patients with different forms of structural disease including congenital heart disease, or heart valve abnormalities. In another embodiment, the system can identify if activation between left and right sides of the heart are synchronized. This can assess the effectiveness of cardiac resynchronization therapy, in which dys-synchronous regions of the heart are 'resynchronized' by strategically tailored pacing leads. This embodiment would enable synchronization therapy to be modified and titrated to optimize left and right synchronization. Although typically applied for the ventricle, left and right synchrony could also be assessed for the atria, to ensure optimum flow of blood through the heart. Finally, the system in another embodiment can assess if the left atrial appendage is electrically active, since patients with inactive or reduced activity in the left atrial appendage may be at risk for stroke. This may be related to clot formation in this structure, and may occur after prior surgery or therapy to the heart or after a device has been placed. Input data in this case may include granular imaging data showing MRI abnormalities, or granular data on regions of low voltage to enable non-invasive detection of structural risk profiles by the network to provide a prognosis, or potentially targets for therapy. Treatment may include ablation to connect these regions of scar or fibrosis.

The computing server 140 may personalize the guidance of ablation. In step 705, the computing server 140 identifies the expected or desired ablation targets. Many of the targets are already defined, although often these targets provide modest success in the prior art. For instance, AF ablation is often performed using pulmonary vein isolation (PVI). This is done for patients with early stage AF as well as later AF, but it is not known if this procedure will work in any one patient and the overall success is 40-60%. One embodiment would input PVI in this step to determine if this approach will or will not work for a given patient, e.g., to determine if that patient is in the 40-60% success group. This may be based on patients in whom this device shows initiating trigger beats for AF near the pulmonary veins (PV). It may also be effective for patients in whom this device has shown important activity during AF (sources) including high rates or focal or reentrant activity at the PVs. In other embodiments, regions of interest may be the right atrial cavotricuspid isthmus, a common site of arrhythmias, or the left atrial mitral annulus. For atrioventricular nodal reentry, common sites for ablation are the slow pathway position in the right atrial septum. In the ventricle, common sites for ablation are the right or left ventricular outflow tracts. Other targets will be familiar to one skilled in the art.

In step 710, the computing server 140 determines whether ablation is likely to work in this patient. This is done in some embodiments by comparing non-invasive and invasive data (whichever is available) in the patient data to a digital classification of how patients with similar patterns responded to ablation. If the classification concludes that similar patients did not respond to ablation, that is the conclusion in step 720.

The computing server 140 provides outputs 720 that are determined quantitatively in an individual by the non-invasive or invasive data (whichever is available), the disease-specific personal digital record (here, for arrhythmia) and the digital classification. For the specific embodiment of AF therapy, outputs comprise ablation or non-ablation therapy that may include drug therapy and lifestyle changes. The computing server 140 may assign scores to each of these outputs using steps outlined in FIG. 5A, including demographic inputs 510 and reversible factors such as high body mass index, poorly treated diabetes, sedentary lifestyle and excessive alcohol consumption, etc. Pharmacological (drug) therapy may be assigned a higher score in a patient of older age, without heart failure and with prior failed AF ablations. These analyses include several other features which will be known to those skilled in the art, to tailor recommendations by the patient data and digital classification for AF. Conversely, if the device shows critical AF regions near the pulmonary veins or other regions amenable to ablation, then ablation is assigned a higher score. If the device indicates no critical regions near PVs or in other regions amenable to ablation, then ablation is assigned a lower score.

If step 710 identifies that ablation is likely to be successful in this patient, then steps 740 onwards are engaged. The computing server 140 determines if the regions of interest for the arrhythmia in this patient lie near proposed regions of ablation in step 705. In some embodiments for AF, if the personal digital record includes AF regions near the PV, step 745 will report that PVI anatomic ablation is likely to work. Step 745 may also indicate likely successful anatomical regions of interest such as right atrial cavotricuspid isthmus ablation for typical atrial flutter, left atrial roof line ablation for left atrial roof-dependent atrial flutter, the posterior left atrial wall or left atrial mitral line.

If other regions of interest away from traditional anatomical targets are indicated, then steps 750-770 guide and enable therapy at those sites.

Step 750 considers arrhythmia critical regions of interest in turn. The analysis of electrical signals may identify areas of repetitive activity, regions of high rate or dominant frequency, drivers with rotational or focal activity, regions of low voltage suggesting scar, signal signatures (FIGS. 5B, 5C) or other regions of interest. The size of these regions is also identified from intracardiac data or from non-invasive data to tailor the size of the mapping tool and therapy tool appropriately. In some cases, individual operators may have a preferred definition of critical region. The device can accommodate a plurality of these critical regions, and thus be used by multiple operators in different patient types. Different critical region definitions may on occasion coincide in any given patient. For instance, in AF, sites of scar may be adjacent to sites of potential drivers. Several other potential coincident sites may occur and can be provided to the physician operator for him/her to make a decision on which to target.

In some embodiments, regions are identified from a small mapping catheter 115 inside the heart that provides high resolution recordings. The signals from the sensing catheter are analyzed to determine a direction in which to move towards a region of interest (e.g., towards a source or other target region). In a related embodiment, this directionality is augmented by recording data 552 from non-invasive devices 110. In each case, the device provides a path in which to move the catheter to get closer to the target. If the non-invasive recordings suggest sites in the left atrial roof, then an invasive catheter could be moved in that direction.

Step 760 determines if the AF mapping catheter is overlying a critical region of interest. The catheter size is important to assess this and is selected using the personal digital record to tailored to the expected size(s) for the patient. If the mapping catheter does not overlie the critical region, the computing server 140 continues to guide navigation. This again can be guided by invasive 115 or non-invasive 110 identification of sites of interest.

In step 765, if the mapping device 115, 554 or another tool overlays a critical region, this region is now targeted for therapy. In some embodiments, a catheter inside the heart that performs mapping may also provide ablation energy to do this in a single (one) shot. In other embodiments, a separate energy delivery (ablation) tool is deployed.

Step 770 assesses the response to therapy, particularly if the region of interest has been eliminated. If not, therapy is repeated.

The process then repeats steps from 750, navigating to and ablating regions of interest until they are all eliminated. The total number of regions treated is determined in real-time by the electrical signals available (steps 700, 730) and the expected numbers from the classification for patients with a similar profile (personal digital record).

In another embodiment, all regions of interest are identified simultaneously using a global mapping from another catheter inside the heart such as a large multipole spherical catheter (basket), or non-invasive methods as discussed. In another embodiment, navigation is applied only to the treatment tool rather than to the wide-area mapping catheter.

Figure 8:
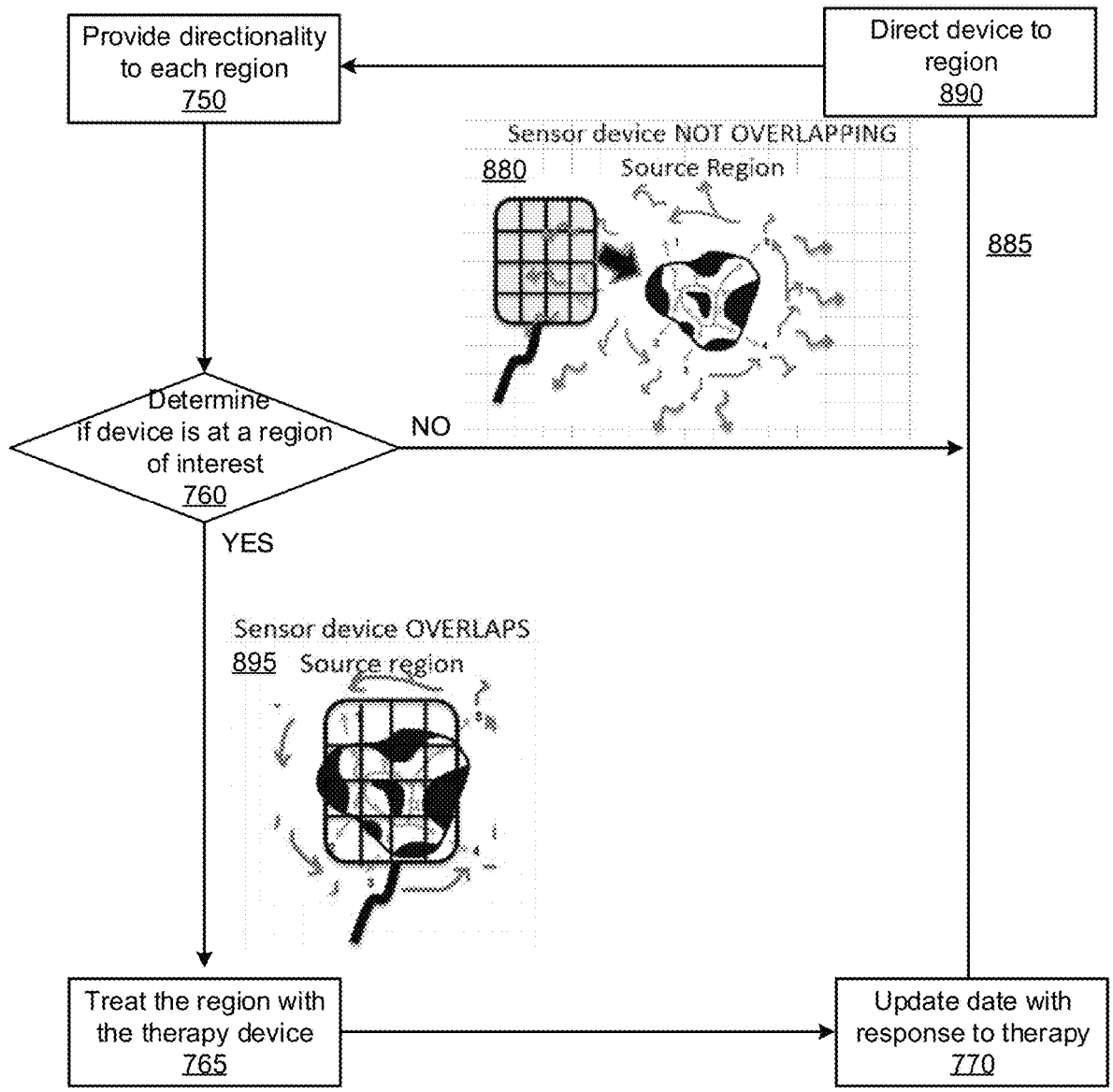
FIG. 8 is a conceptual diagram illustrating personalized guidance of ablation therapy, in accordance with one or more embodiments.

FIG. 8 is a conceptual diagram illustrating personalized guidance of ablation therapy, according to some embodiments. Step 880 illustrates a sensing tool (e.g., a mapping catheter) some distance from a region of interest. The system analyzes electrical waves to determine if the mapping catheter device overlays a region of interest, for example, signals representing the region of interest overlay as many electrodes of the mapping tool as possible. In some embodiments, the area of the sensor that covers the region of interest is maximized There are many potential regions of interest, such as those in paragraph 165 above. If the operator is examining repetitive activity as a critical region, repetitive activity in the center of the mapping field indicates that the device is centrally placed over this region. If the repetitive activity is at one edge of the mapping device, then energy may be delivered, but the device should then be moved in the direction of that edge to attempt to maximize the number of sensing elements of the device that overlay the repetitive activity. If the operator is targeting high rate or dominant frequency, the same logic is applied. Similarly, if the operator is targeting regions of low voltage indicative of scar, or regions exhibiting signatures identified by the device. If the operator is targeting a focal source for an atrial tachycardia or ventricular tachycardia, vectorial analysis is used to indicate the direction of the source. If the operator is targeting drivers for a complex rhythm disorder such as atrial fibrillation, which may be focal or rotational, then modified vectorial analysis will indicate the direction of source. The modification for atrial or ventricular fibrillation is that activity exiting an AF source varies from beat to beat (cycle to cycle), and so the vectorial analysis has to take an average over multiple cycles to identify the predominant vectorial direction for analysis.

Step 880 illustrates an example that the mapping catheter does not overlay the region of interest. The system then provides navigation information to direct the catheter towards the closest region of interest. This is displayed on a portable display such as a dedicated portable device or a smartphone app, or on a dedicated medical display unit. Each of these units has appropriate data security and privacy safeguards in place. This navigation step is iterated 885. In step 895 the mapping tool has been determined to overlay the region of interest. This is termed the treatment position. The display tool may indicate "Optimal position, ablate." Ablation can now be performed in some embodiments with the same mapping/ablation probe. For example, the probe is capable of delivering energy to modify tissue regions related to the heart rhythm disorder. In another embodiment, a separate ablation catheter can be inserted. The process now repeats again in steps 880 onwards until the operator determines that sufficient regions of interest have been treated. This may be all regions or a number determined by the personal digital record for patients of this type relative to the location and size of regions.

Example Algorithm for Direction Guidance

Figure 9A:
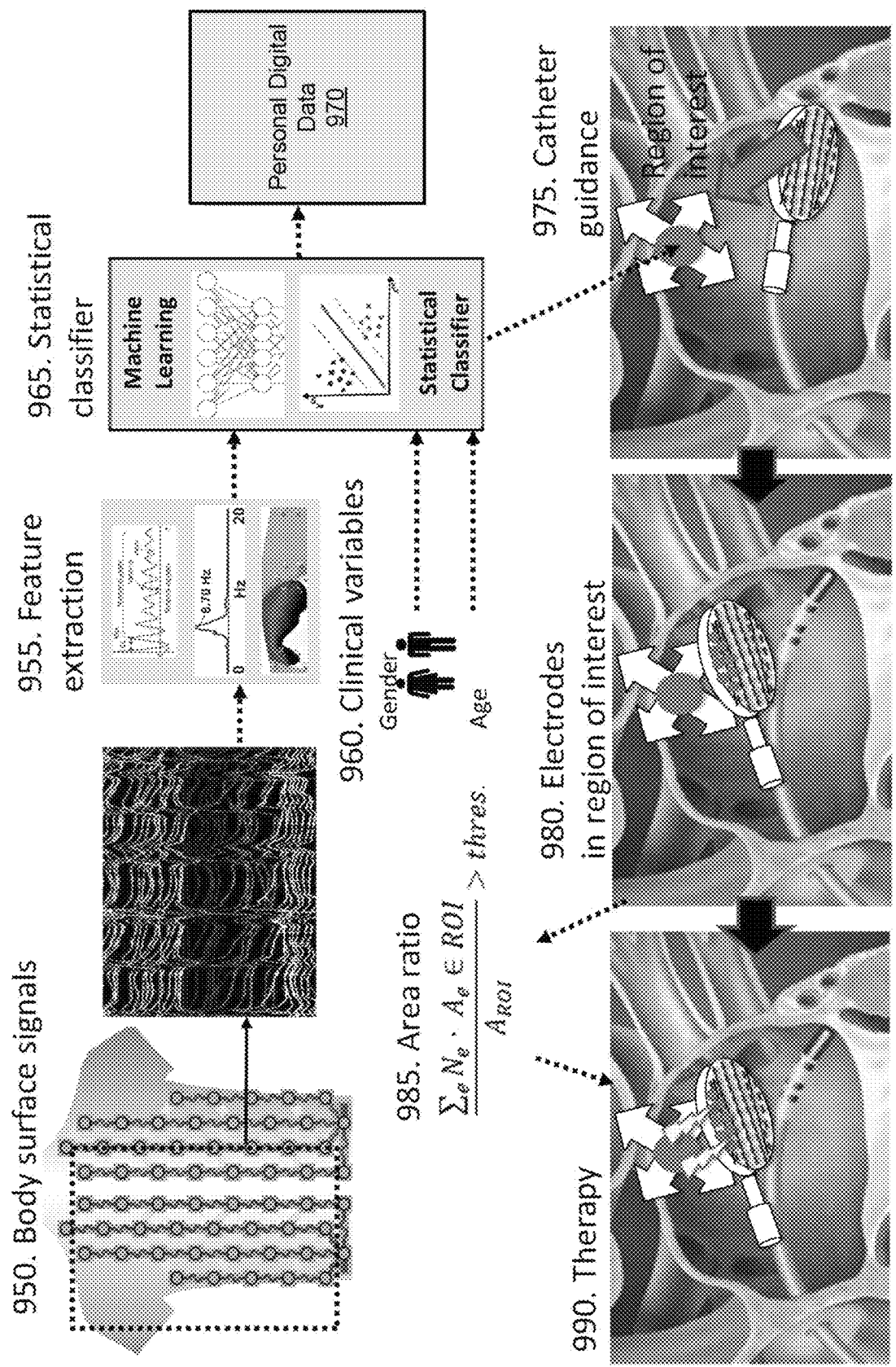
FIG. 9A is a graphical illustration of a flowchart depicting an example process that is executable by software algorithm for a computing system to perform a directional guidance for arrhythmias, in accordance with one or more embodiments.

FIG. 9A is a graphical illustration of a flowchart depicting an example process that is executable by software algorithm for a computing system (e.g., computing server 140) to perform a directional guidance for arrhythmias, in accordance with one or more embodiments. The software algorithm may be stored as computer instructions that are executable by one or more general processors (e.g., CPUs, GPUs). The instructions, when executed by the processors, cause the processors to perform various steps described in the process. Body signals 950 may be sensed by a body surface device 110. The signals may be raw or processed by one or more data processing pipeline discussed in FIG. 4. The features 952 of the body signals 950 are extracted 955 using methods such as spectral or instantaneous phase analysis in single or combinations of electrodes. Other features may include features based in the temporal domain of the signal and their first and second derivative, such as percentiles, number of local maxima or minima, and features extracted from the autocorrelation. Other features could be extracted from the parametric or signature analysis referred in FIG. 5B. The feature extraction 955 could be carried out without the use of the patient's anatomy extracted from medical image (CT, MRI) techniques. Features are integrated with clinical variables 960 such as age, gender into a statistical classifier 965. Multiple statistical and machine learning approaches 965 may be used to integrate these features, including correlation coefficients from multivariate regression or supervised machine learning using convolutional neural networks or support vector machines trained to a specific output label of AF termination, long-term outcome, success rate of specific drug or ablative therapies or other labels, during algorithmic development. Step 970 shows that these integrated features are input into a personal digital record-based arrhythmia predictions, which can identify the specific phenotype of the patient disease such as a likely PV based AF, or AF from sites that arise away from the PVs, or VT that arises from sites common in patients with that phenotype.

In step 975, the computing server 140 may determine directionality using a non-invasive device as guidance to guide a probe (e.g., a catheter) towards one of the locations of the heart that are associated with the heart rhythm disorder. Directionality analysis allows to identify the cardiac region from which the electric disturbance is arising and therefore the target for ablation. The computing server 140 may identify these cardiac regions with no basic assumption of their sustaining or initiating mechanism (re-entrant activity, focal activity, repetitive activity, tachy-pacing, multiple waves), and identify those sites from which the electric activity propagates to the rest of the heart and initiates or maintains the arrhythmia. In one embodiment, the directionality analysis can distinguish activity propagation from left versus right atria, and provide the direction to these anatomical chambers. In other embodiment, the directionality analysis can identify the specific anatomical region maintaining the arrhythmia, such as the pulmonary veins, left or right appendages or other anatomical sites, and provide the direction to these specific sites.

Step 975 shows that directionality analysis may be used to guide an ablation catheter inside the heart, or an external ablation source (such as proton beam irradiation) to the critical region of interest, e.g., a source or target region of the arrhythmia. The location algorithm may identify the position of the ablation catheter relative to the region of interest in the heart, and guide the ablation catheter to the region of interest. The ablation catheter is then analyzed to obtain a ratio of the number of electrodes of the mapping device (e.g., a mapping catheter) that cover the region of interest at step 980. This is done by determining the area of the sensor that covers the predicted region of interest, as a ratio of the entire sensed area. Item 985 determines whether the area ratio exceeds a desired ratio threshold. In some embodiments, if this ratio exceeds a threshold, such as 0.75, (three quarters of the mapping device overlaps the region of interest), then therapy is applied at this site in step 990. In other embodiments, it may be permissible to apply therapy if this ratio exceeds 0.5 or some other threshold values. If the ratio is low, in other words the device has only a small overlap with a region of interest, then in some embodiments the system provides directionality guidance to move a treatment device to increase overlap with the region of interest before applying therapy (steps 957-990).

For directionality analysis from a device inside the heart, signals at the sensor site are processed and used to calculate the direction in which to move the electrode array to reach or navigate to the source. This is analogous to global positioning systems which use the current position to navigate to a desired location, without examining the entire map of the globe or remote sites. This approach enables higher resolution mapping than currently available in wide-area global or panoramic mapping systems within the heart.

Figure 9B:
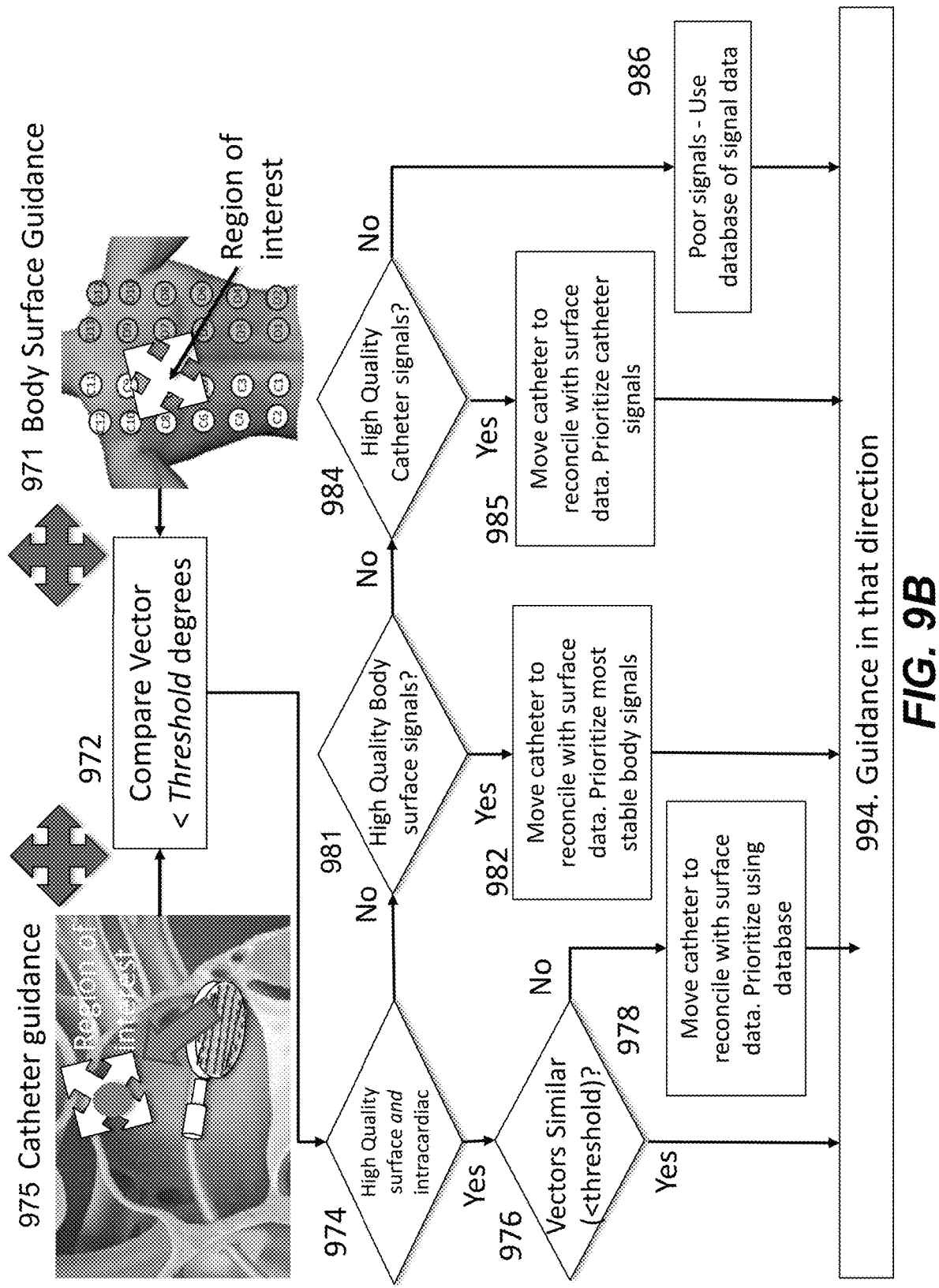
FIG. 9B is a graphical illustration of a flowchart depicting an example process that is executable by software algorithms for a computing system to integrate use of body surface or internal catheter systems for directional guidance for arrhythmias, in accordance with one or more embodiments

In some embodiments, directionality analysis can be performed using combination of body surface signals and signals at the probe. For example, the probe contains sensors for recording and may be referred to as a catheter sensor. FIG. 9B is a graphical illustration of a guidance system that integrates data from sensing devices on the body surface (such as FIGS. 3A, 3B) and sensing devices inside the heart (such as step 554 in FIG. 5B) to direct therapy, executable by software algorithms for a computing system (e.g., computing server 140) in accordance with one or more embodiments. The software algorithm may be stored as computer instructions that are executable by one or more general processors (e.g., CPUs, GPUs). The instructions, when executed by the processors, cause the processors to perform various steps described in the process. Signals from these devices may be raw or processed by one or more data processing pipeline discussed in FIG. 4. Features of body signals and intracardiac signals can be extracted using methods described above such as spectral or phase analysis, or time domain features of signals from single or combinations of electrodes.

Step 975 takes guidance direction from an internal catheter input (also FIG. 9A) and step 971 takes guidance direction from the body surface input. Steps 972 to 994 combine these two input data sets to guide a device or catheter towards a region of interest for a heart rhythm disorder in relation to the body surface device. The embodiment focuses on providing directional information in the form of left/right/up/down guidance towards a functional region of interest, agnostic to location within the heart (or other organs). This is quite distinct from the more general prior art applications of ascertaining catheter position within the heart (i.e. three dimensional catheter navigation), that is not focused on a specific function (e.g., heart rhythm disorder). The embodiment compares functional information in vectors, spatial activation or timing between the body surface and catheter inputs for a specific heart rhythm disorder in a specific patient. The embodiment thus uses the body surface patch to provide global information on direction towards a functional region of interest, avoiding the need for a system that creates an anatomical 3D reconstruction.

Step 972 compares the two body surface and catheter inputs. In some embodiments, inputs are compared by vectors in a vectorial analysis. In one approach, the embodiment determines similarity of vectors towards a source or region of interest for both inputs within a threshold. For instance, a threshold of 45 degrees would indicate a confidence interval of plus/minus 22.5 degrees about a core vector. Other thresholds can be applied, depending on the quality of signals, the rhythm under consideration and location within the heart. Vectors can be compared using multiple mathematical approaches including correlation coefficients from multivariate regression, or supervised machine learning using convolutional neural networks or support vector machines. Machine learning can be trained to specific output labels of vectorial direction to regions where therapy was acutely successful (one outcome label), produced good long-term freedom from arrhythmia after therapy (a second outcome label) or produced good quality of life after therapy based on clinical determination (a third outcome label). Training techniques of machine learning models are further discussed in FIG. 6.

In other embodiments, steps 972 to 994 compare other (non-vectorial) data between inputs to calculate directions in which to move a catheter. Some embodiments compare spatial differences in patterns of electrical activation over time. For instance, if the body surface indicates a focal beat with activation that emanates radially outward, the catheter can be directed until its pattern of activation matches this focal beat pattern. If the body surface input indicates a rotational activation pattern with a certain time periodicity, the catheter can be moved until it mimics this rotational pattern. Other spatial patterns between inputs will be evident to those familiar with the art. Of note, there is smoothing of activation and other differences between the body surface and catheter in the heart, and confidence intervals must be included into comparisons between these inputs. Some activation patterns in complex rhythms such as atrial fibrillation are more difficult to quantify as intuitive spatial patterns, but can be compared in terms of similar frequency rate, similar organizational index (width of spectral dominant frequency), similar disorganization (from metrics such as Shannon entropy), and other parameters that will be familiar to a practitioner familiar with the art.

In yet other embodiments, steps 972 to 994 compare temporal (timing) data in electrical information between inputs to calculate directions in which to move a catheter. For instance, in the complex arrhythmia of atrial fibrillation, if activation times in a localized region of the body surface input span the cycle length (typically 150-220 ms), then the catheter will be moved until its recordings also span this cycle length. In an atypical atrial flutter or ventricular tachycardia, conduction may be slow with a prolonged activation time sequence through a reentrant isthmus or near a scar borderzone. The steps 972 to 994 will guide the catheter until its activation time sequence matches that on the body surface. Other less intuitive timing metrics include spectral timing, spectral organization and phase, each of which can be compared between inputs to provide guidance information to the catheter.

In some embodiments, the spatial, vectorial, and timing comparisons can be combined or blended to provide catheter guidance, depending on the specific case, specific heart rhythm disorder, patient characteristics, database of stored patterns and operator preference. Specific steps to enable each of these functions are now outlined. All steps described are illustrative and not designed to be an exhaustive list of permutations of these inventive elements.

In step 974, signal quality of both the catheter and body surface signals are analyzed to create a confidence level in each. Quality of the catheter and body surface signals and/or directions can be identified using signal-to-noise ratio algorithms, extraction of noise-related features as described in 952, by using specific machine learning algorithms trained with noisy directions and signals, and other techniques that will be evident to a practitioner with ordinary skill in the art. In step 974, if both body surface and catheter directional signals have high quality, compared with a specific quality threshold, then their relative vectors are determined. In step 976, if these vectors are similar, within a threshold as discussed, then that directional vector is used to provide guidance to the user.

If vectors are not similar, one of the vectors may be prioritized 978 based on past records and data from a database of procedures (e.g., predetermined rules). The prioritized vector serves as the controlling vector for directionality. For example, the prioritization of one vector over another may be based on various factors such as the location in the organ (e.g., heart), the rhythm under consideration and patient specific factors such as age, gender, heart size, and prior surgery or instrumentation in the heart. In some embodiments for treating atrial fibrillation, if the catheter currently lies near the inter-atrial septum, the vector from the catheter is prioritized higher because body surface signals poorly represent the intra-atrial septum. Conversely, in a patient in whom multiple prior ablations have been performed, body surface signals may be prioritized since internal signals may have lower quality and lower confidence. In general, body surface signals enjoy spatial and temporal filtering due to conduction through body tissues, and thus may show greater temporo-spatial stability of vectors. Accordingly, body surface vectors may be prioritized, when available, for providing a global directional vector.

In another embodiment, steps 976 and 978 move the catheter to reconcile high quality data from the body surface input with high quality data from the catheter input. As described above, this may involve non-vectorial information such as spatial or timing information.

Step 981 determines, when signal types are not both of high quality, whether the body surface signal is of high quality (confidence). If so, this signal type is used to determine directional vector. Oftentimes body surface signals enjoy spatial and temporal filtering due to conduction through body tissues, and thus may show greater temporo-spatial stability of vectors. Accordingly, for providing a global directional vector, body surface signals are prioritized in step 982.

In another embodiment, step 982 moves the catheter to reconcile high quality data from the body surface input with data from the catheter input. As described above, this may involve non-vectorial information such as spatial or timing information. The step 982 will prioritize high quality body surface signals.

If body surface signals are not of high quality, step 984 assesses whether the internal catheter device signals are of high quality. If so, these signals are used to provide a navigation direction.

In another embodiment, steps 984 to 985 will provide guidance information to move the catheter to reconcile data from the body surface input with high quality data from the catheter input. As described above, this may involve non-vectorial information such as spatial or timing information. The step 982 will prioritize high quality catheter signals.

In step 986, if neither the body surface nor catheter signals are of sufficient quality, past records and data from a database of procedures (e.g., predetermined rules) may be used to provide a probabilistic directionality. Several clinical and mapping features may be used. In some embodiments, such as for atrial fibrillation, clinical guidance may suggest directions towards the right atrium in patients with multiple prior ablations in the left atrium. Conversely, in a patient with no prior ablation who is relatively young and with few other medical problems, guidance may direct the treatment device towards the pulmonary veins. Step 986 may integrate these features to create a personal digital record-based arrhythmia prediction. This also represents phenotypes such as patients with atrial fibrillation near the pulmonary veins, or atrial fibrillation from other sites (particularly in patients with prior diseases or in whom pulmonary vein ablation has not worked), or ventricular tachycardia that arises from common sites such as near ventricular scar, near the ventricular outflow tracts or other sites more common in patients with different features. The database for providing directionality guidance is constructed based on detailed mapping in patients of many different types, and includes response to ablation of regions of interest.

In another embodiment, step 986 will provide guidance information to move the catheter to reconcile data from the body surface input with data from the catheter input. As described above, this may involve non-vectorial information such as spatial or timing information. If both data inputs are of lower quality, step 986 will use a database relating stored patterns or timing of successful and unsuccessful sites which can be matched to the characteristics of the current patient.

Directional guidance in some embodiments can be implemented by deep learning classifiers trained with previous and stored clinical data. Deep learning models may comprise neural networks, traditional machine learning model, or statistical models. In one example embodiment, the machine learning model is trained to identify the direction (vector) from the catheter to region of interest, the electrode or subset of electrodes of the catheter closer to region of interest, or other. The output of this machine learning model can be used to guide the catheter 962 to the region of interest. Training techniques of machine learning models are further discussed in FIG. 6.

Figure 9C:
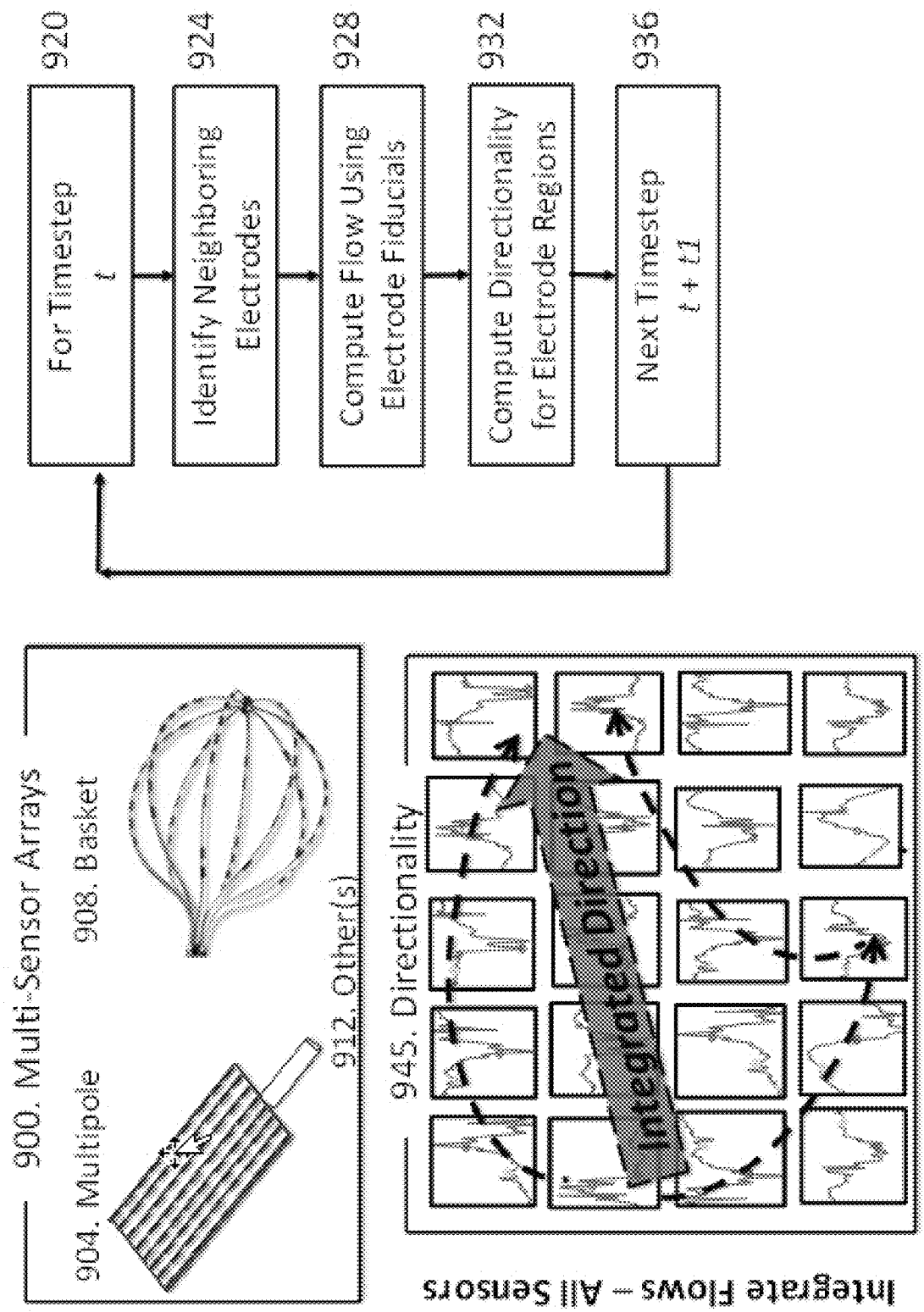
FIG. 9C is a graphical illustration of a flowchart depicting an example process that is executable by software algorithm for a computing system use guidance from a catheter inside the heart to guide an ablation catheter inside the heart.

FIG. 9C is a graphical illustration of a flowchart depicting an example process that is executable by software algorithm for a computing system (e.g., computing server 140) to use directional guidance from a catheter inside the heart to guide an ablation catheter inside the heart. Item 900 shows sensing devices of many forms. The multipole device 904 shows a high resolution multipolar spade catheter, basket device 908 shows a multipolar basket catheter, and multiple other types exist 912.

The flowchart starts at timesteps 920 starting at t. Neighboring electrodes are identified at step 924 as physically adjacent, with known electrode spacings. Step 928 computes direction of electrical propagation using electrode signals integrated over the timestep t, shown previously in FIG. 8. First, the system spatially interpolates the wavefront √ by electrodes at known spacing on the array. For each point i along this interpolated wavefront √ at time t, the system searches within a circle for the point j at the next time step with the most similar gradient. The system infers that the activation wavefront has traveled from point i to point j in this time, and marks this flow with an instantaneous flow vector (propagation over time). Step 932 repeats the computation of flow (directionality) across regions of the electrode array. Step 936 repeats this process for subsequent timesteps.

Step 945 illustrates multiple electrograms over windows of 150 ms, with dotted lines indicating flow computed from electrograms as indicated. Directionality is now integrated over the entire available number of electrodes on the array to determine the average direction of electrical flow. Directionality could be extracted from feature analysis as explained in FIG. 5A or using specific signatures identified as in FIG. 5B. The average direction of electrical flow is capable of describing complex spatiotemporally changing fibrillation 945. Guiding the sensor in the reverse direction will thus move closer to the nearest source or other target region. This approach improves upon the accuracy provided by a single electrode which has historically not been able to find critical regions of interest for many heart rhythm disorders such as fibrillation.

For AF, candidate ablation targets include mathematical combinations of electrogram features plus comorbidities (e.g., body mass index, diabetes, hypertension), demographics (e.g., age, gender, prior ablation or not) and, if available, genetic, metabolic and biomarker information. Novel electrogram targets can extend 'traditional' targets to targets such as repetitive patterns, or transient rotations or focal patterns, or interrupted rotational or focal patterns, may be critical to maintaining arrhythmia in some individuals, as previously discussed. This embodiment defines these electrogram features, by determining in individual patients which may be related to favorable outcomes. This then becomes a numerical classification within the digital classification (i.e. classification) as data from more individuals is labeled and accumulated.

Depending on the patient, therapy targets may be rotational or focal sources/drivers, or other electrical features—regardless of structure. Intermediate phenotypes may be present in phenotypes in specific individuals (electrical and structural, which may dynamically change with e.g., changes in health status). Again, multiple forms of the electrical pattern may colocalize with such structural elements. The computing server 140 may store electrical signals associated with these sites to update the personal and population databases. Therapy may include the destruction of tissue by surgical or minimally invasive ablation, to modulate via electrical pacing or mechanical pacing, or using gene, stem cell, or drug therapy. Medications may include class I agents to decrease atrial conduction velocity, or class III agents to prolong refractoriness. AF ablation may not just eliminate tissue, but target areas bordering fibrosis or areas of electrical vulnerability. Therapy can also be directed to related tissue to these regions, their nerve supply, or other modulating biological systems.

Figure 10A:
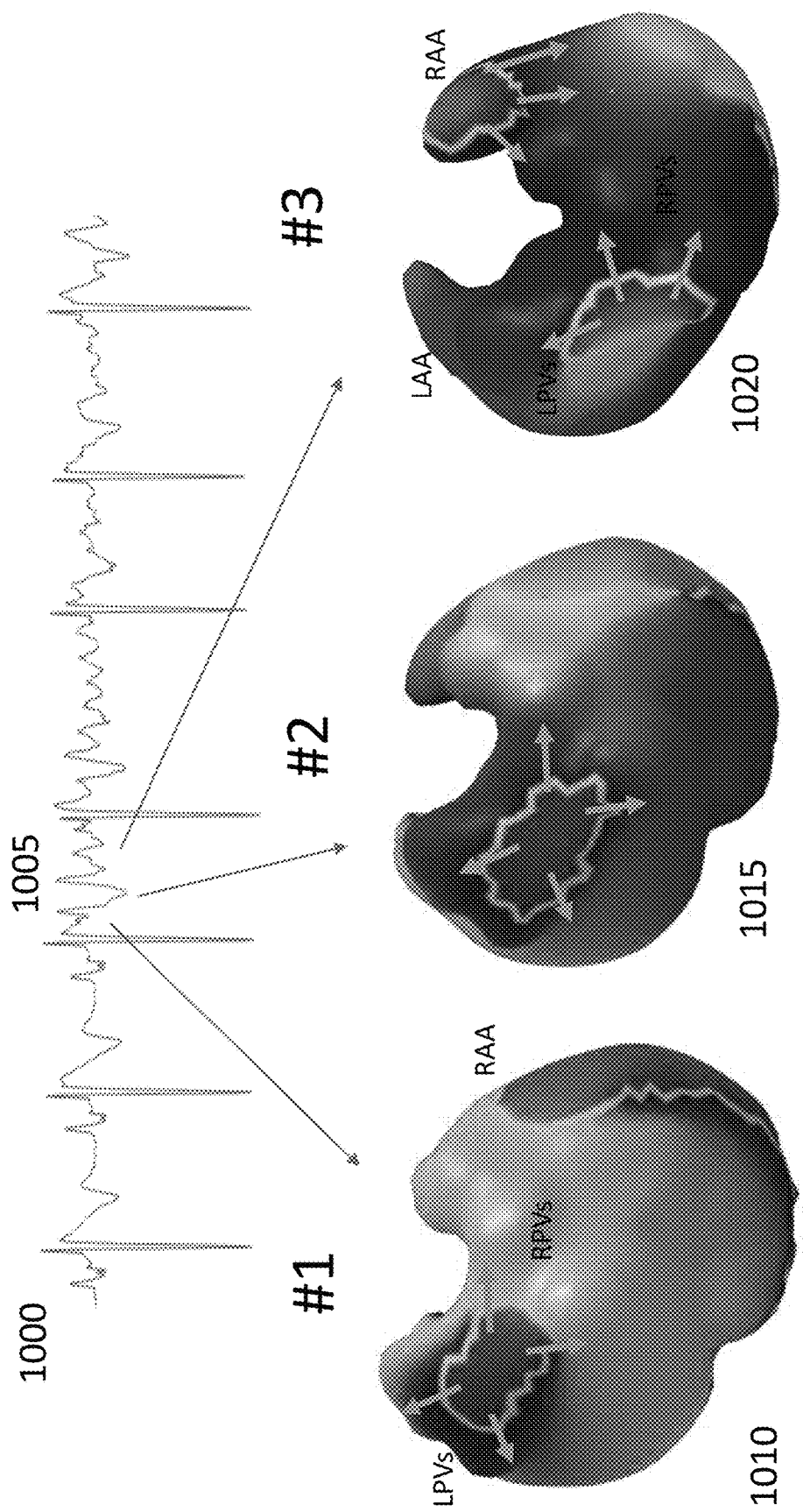
FIGS. 10A, 10B, 10C, 10D, and 10E are various graphical illustrations of examples of patients with heart conditions, in accordance with some embodiments.

FIG. 10A is a graphical illustration of an example of a patient with initiating beats for AF near PVs. Signals from a single surface electrocardiographic lead showing the segment under analysis 1000, whose directionality maps were obtained at 3 temporal points from the AF initiating interval 1005. Directional analysis of time instants 1010 and 1015 on the right and left atria showed centrifugal activation from the posterior left atrial wall, whereas instant 1020 showed a centrifugal activation from the right pulmonary veins and a secondary centrifugal activation from the right atrial appendage. In this case, subsequent ablation near the pulmonary veins (pulmonary vein isolation) was effective at eliminating the AF in the long term.

Figure 10B:
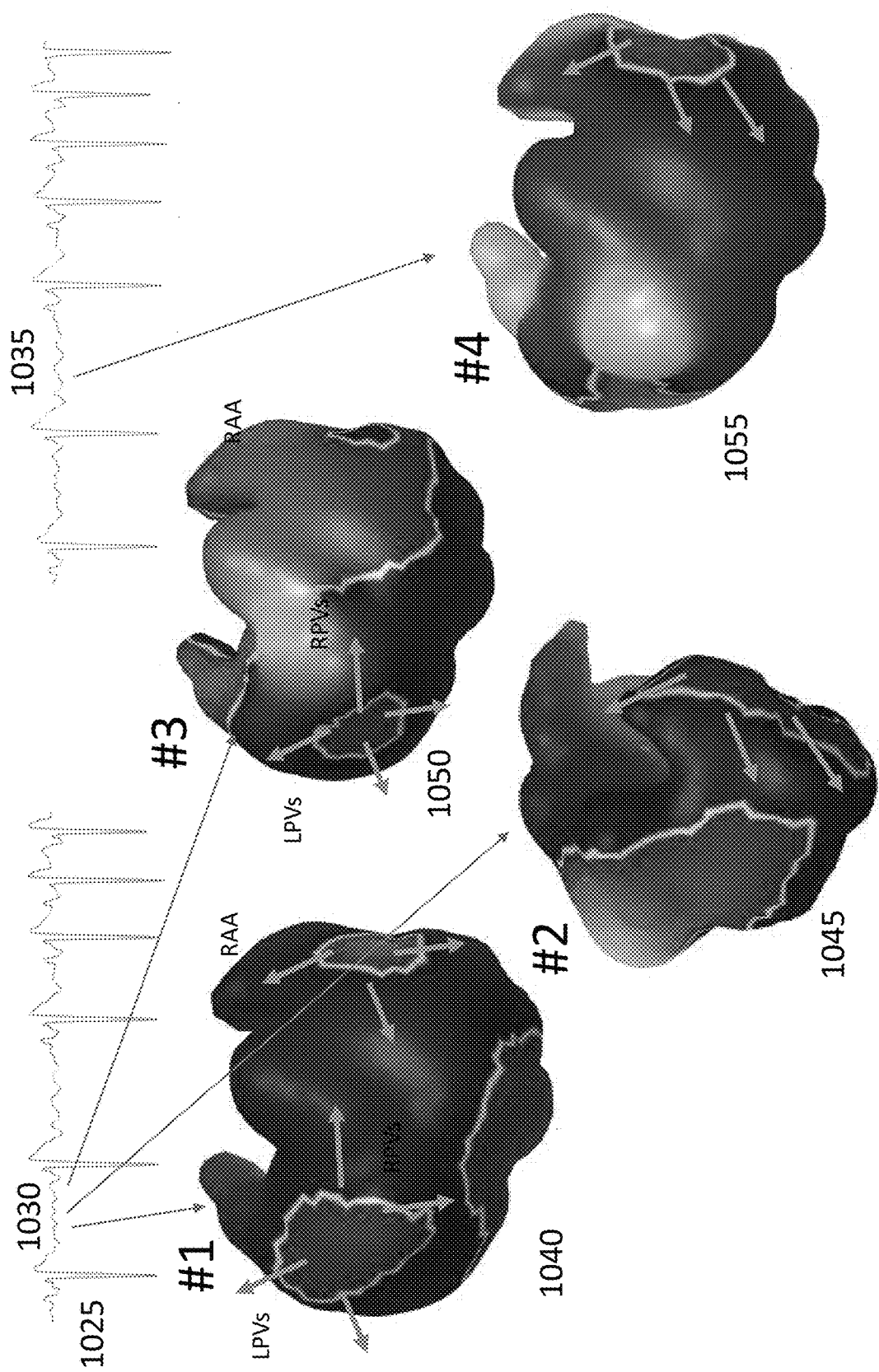

FIG. 10B is a graphical illustration of an example of a patient with initiating beats for AF from PV and non-PV sites. Surface electrocardiographic signal showing the segment under analysis 1025, whose directionality maps were obtained at 4 temporal points from the AF initiating intervals 1030 and 1035. Directional analysis of time instant 1040 on the right and left atria showed a centrifugal activation from the left pulmonary veins and from the right atrial appendage. Directional analysis of time instant 1045 showed a centrifugal activation from the right atrial appendage. Directional analysis of time instant 1050 showed a centrifugal activation from the posterior left atrial wall, and directional analysis of instant 1055 showed again a centrifugal activation from the right atrial appendage. In this case, subsequent ablation near the pulmonary veins (pulmonary vein isolation) reduced AF on follow-up but did not eliminate it.

Figure 10C:
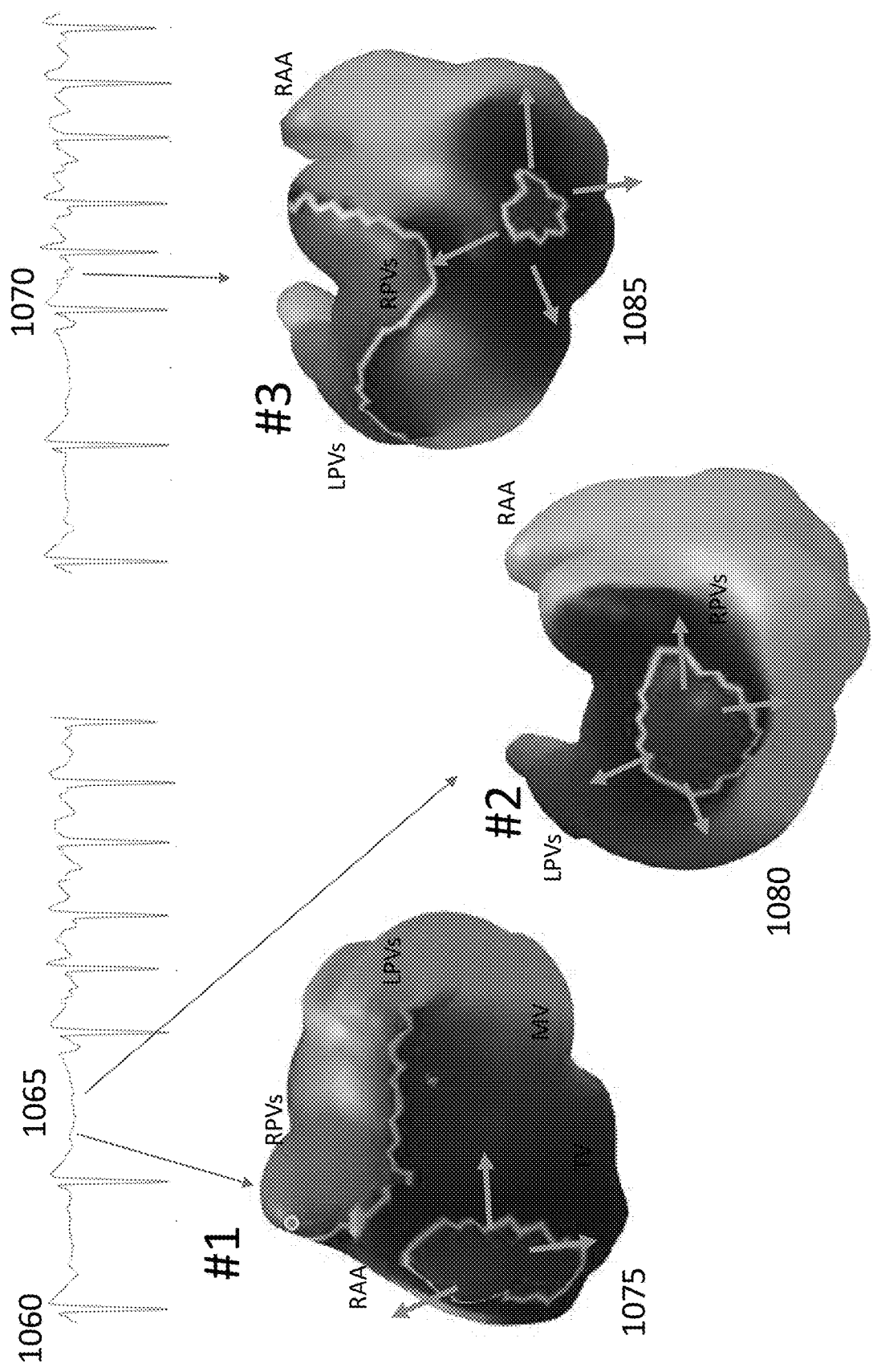

FIG. 10C is a graphical illustration of an example of a patient with initiating beats for AF remote from PVs. Surface electrocardiographic signal showing the segment under analysis 1060, whose directionality maps were obtained at 3 temporal points from the AF initiating intervals 1065 and 1070. Directional analysis of time instant 1075 on the right and left atria showed a centrifugal activation from the right atrial appendage. Directional analysis of time instant 1080 showed a centrifugal activation from the right pulmonary veins, and directional analysis of time instant 1085 showed a centrifugal activation from the inferior cava vein. In this case, subsequent ablation near the pulmonary veins (pulmonary vein isolation) did not eliminate AF in the long term and a repeat ablation procedure was required.

Figure 10D:
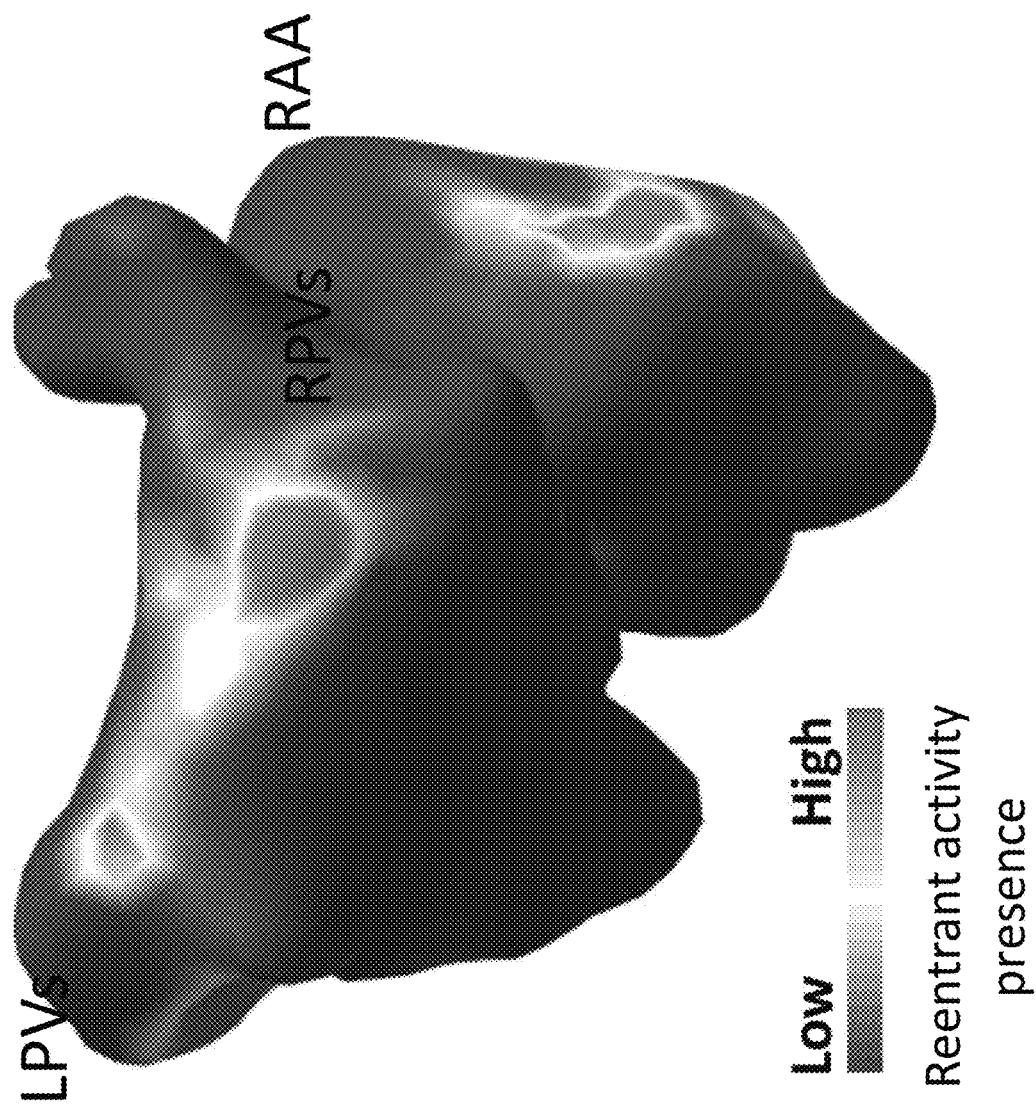

FIG. 10D is a graphical illustration of activation in the atrial in a patient with sustaining regions for AF near PVs. Non-invasive reconstruction of the reentrant activity during atrial fibrillation showed primary reentrant sources near the left and right pulmonary veins and absence of reentrant activity elsewhere. In this patient, AF acutely terminated after pulmonary vein isolation by radiofrequency ablation. This indicates that driving regions for AF can be identified from the device non-invasively, and used in this case to predict that PVI ablation will be effective in this patient.

Figure 10E:
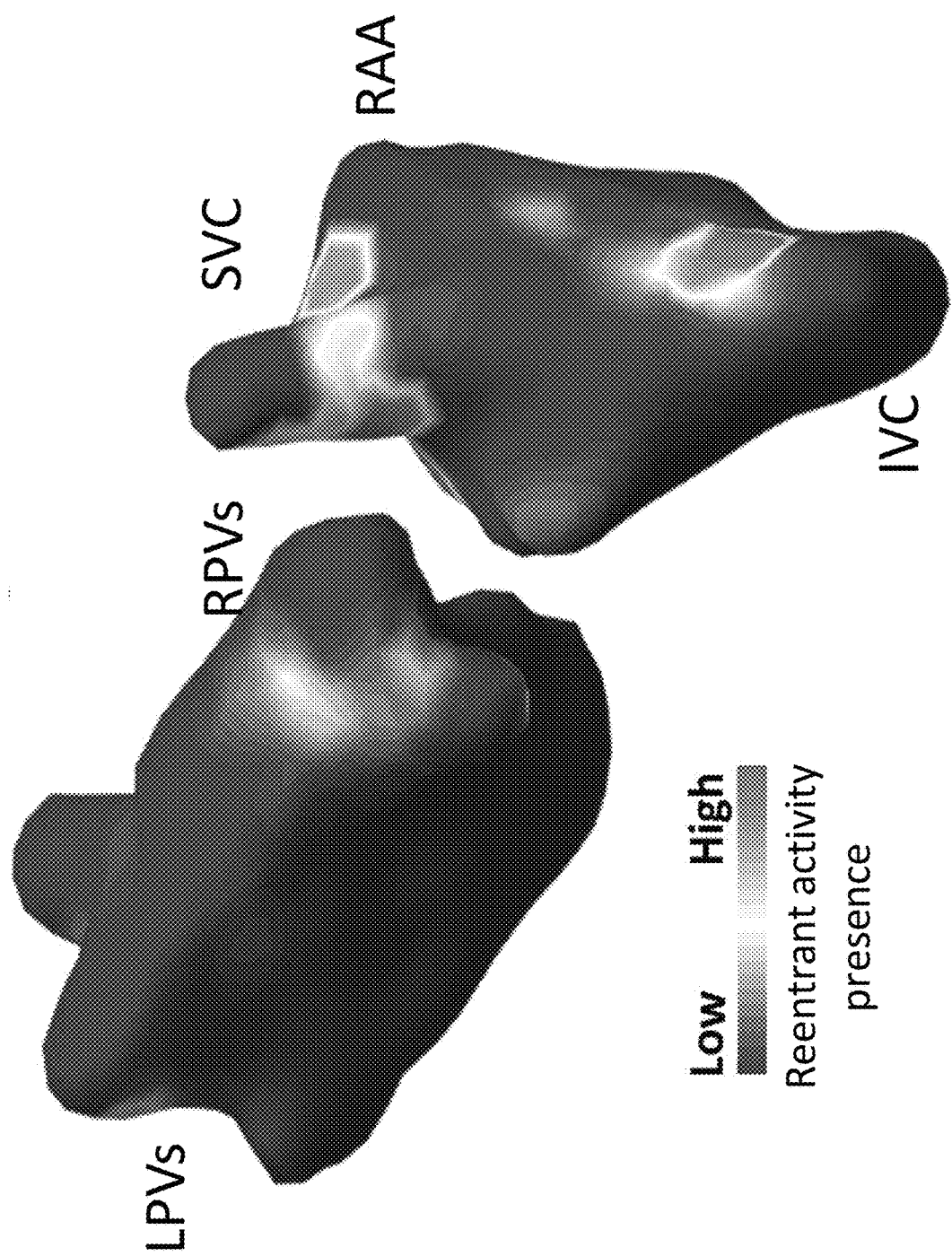

FIG. 10E is a graphical illustration of an example of a patient with sustaining regions for AF in the right atrium, remote from PVs. Non-invasive reconstruction of the reentrant activity during atrial fibrillation showed primary reentrant sources in the right atrium and absence of reentrant sources near the pulmonary veins. This patient did not acutely terminate AF after pulmonary vein isolation. This indicates that driving regions for AF outside the PV regions can be identified from the device non-invasively, and used in this case to predict that PVI ablation is less likely to be effective alone at preventing long-term recurrence in this patient.

FIGS. 10A-E indicate regions of triggers or sources which are illustrated as a heat map on the representation of the heart that may be displayed in a graphical user interface. If multiple triggers or sources are identified across multiple beats or initiations of the rhythm, each of these triggers can be aggregated or integrated into this said heat map. The heat map can be a simple accumulation of the information for each of the regions of interest. It may also be an arithmetic mean or a geometric mean designed to emphasize the region of interest over background activity.

A heat map for a heart rhythm disorder in a subject may be generated based on one or more directionality maps such as by aggregating the directionality maps. A directionality map may be generated for the heart rhythm disorder based on electrical signals measured by a body surface device 110. The directionality map may describe pathways that indicate beats that initiate an onset of the heart rhythm disorder. The directionality map may be generated by applying a trained machine learning model to the electrical signals, wherein the machine learning model is trained on training examples comprising electrical signals of human hearts and known source regions of the heart rhythm disorder. Source regions for the heart rhythm disorder may be determined. In turn, a heat map may be generated based on the determined information and directionality maps.

Computing Machine Architecture

Figure 11:
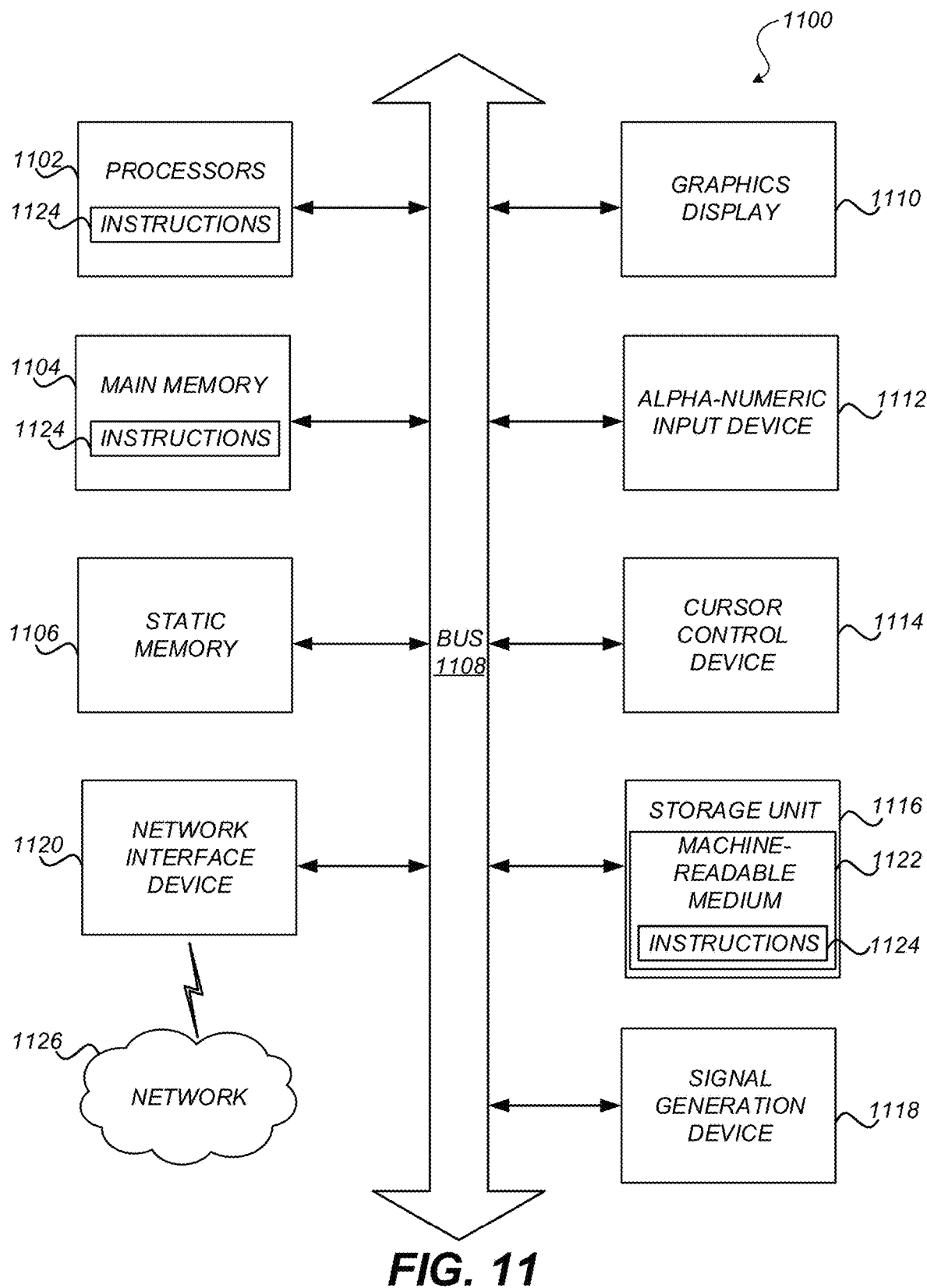
FIG. 11 is a block diagram of an exemplary embodiment of a general computer system.

FIG. 11 is a block diagram illustrating components of an example computing machine that is capable of reading instructions from a computer-readable medium and execute them in a processor (or controller). A computer described herein may include a single computing machine shown in FIG. 11, a virtual machine, a distributed computing system that includes multiples nodes of computing machines shown in FIG. 11, or any other suitable arrangement of computing devices.

By way of example, FIG. 11 shows a diagrammatic representation of a computing machine in the example form of a computer system 1100 within which instructions 1124 (e.g., software, source code, program code, expanded code, object code, assembly code, or machine code), which may be stored in a computer-readable medium for causing the machine to perform any one or more of the processes discussed herein may be executed. In some embodiments, the computing machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The structure of a computing machine described in FIG. 11 may correspond to any software, hardware, or combined components shown in FIG. 1A, including but not limited to, the client device 120, the physician device 132, the computing server 140, and various engines, interfaces, terminals, and machines in this disclosure. While FIG. 11 shows various hardware and software elements, each of the components described in FIG. 1A may include additional or fewer elements.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 1124 that specify actions to be taken by that machine. Further, while only a single machine is illustrated, the term "machine" and "computer" may also be taken to include any collection of machines that individually or jointly execute instructions 1124 to perform any one or more of the methodologies discussed herein.

The example computer system 1100 includes one or more processors 1102 such as a CPU (central processing unit), a GPU (graphics processing unit), a TPU (tensor processing unit), a DSP (digital signal processor), a system on a chip (SOC), a controller, a state equipment, an application-specific integrated circuit (ASIC), a field-programmable gate array (FPGA), or any combination of these. Parts of the computing system 1100 may also include a memory 1104 that store computer code including instructions 1124 that may cause the processors 1102 to perform certain actions when the instructions are executed, directly or indirectly by the processors 1102. Instructions can be any directions, commands, or orders that may be stored in different forms, such as equipment-readable instructions, programming instructions including source code, and other communication signals and orders. Instructions may be used in a general sense and are not limited to machine-readable codes. One or more steps in various processes described may be performed by passing through instructions to one or more multiply-accumulate (MAC) units of the processors.

One and more methods described herein improve the operation speed of the processors 1102 and reduces the space required for the memory 1104. For example, the signal processing techniques and machine learning methods described herein reduce the complexity of the computation of the processors 1102 by applying one or more novel techniques that simplify the steps in training, reaching convergence, and generating results of the processors 1102. The algorithms described herein also reduces the size of the models and datasets to reduce the storage space requirement for memory 1104.

The performance of certain of the operations may be distributed among the more than processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations. Even though in the specification or the claims may refer some processes to be performed by a processor, this should be construed to include a joint operation of multiple distributed processors.

The computer system 1100 may include a main memory 1104, and a static memory 1106, which are configured to communicate with each other via a bus 1108. The computer system 1100 may further include a graphics display unit 1110 (e.g., a plasma display panel (personal digital record), a liquid crystal display (LCD), a projector, or a cathode ray tube (CRT)). The graphics display unit 1110, controlled by the processors 1102, displays a graphical user interface (GUI) to display one or more results and data generated by the processes described herein. The computer system 1100 may also include alphanumeric input device 1112 (e.g., a keyboard), a cursor control device 1114 (e.g., a mouse, a trackball, a joystick, a motion sensor, or other pointing instrument), a storage unit 1116 (a hard drive, a solid state drive, a hybrid drive, a memory disk, etc.), a signal generation device 1118 (e.g., a speaker), and a network interface device 1120, which also are configured to communicate via the bus 1108.

The storage unit 1116 includes a computer-readable medium 1122 on which is stored instructions 1124 embodying any one or more of the methodologies or functions described herein. The instructions 1124 may also reside, completely or at least partially, within the main memory 1104 or within the processor 1102 (e.g., within a processor's cache memory) during execution thereof by the computer system 1100, the main memory 1104 and the processor 1102 also constituting computer-readable media. The instructions 1124 may be transmitted or received over a network 1126 via the network interface device 1120.

While computer-readable medium 1122 is shown in an example embodiment to be a single medium, the term "computer-readable medium" should be taken to include a single medium or multiple media (e.g., a centralized or distributed database, or associated caches and servers) able to store instructions (e.g., instructions 1124). The computer-readable medium may include any medium that is capable of storing instructions (e.g., instructions 1124) for execution by the processors (e.g., processors 1102) and that cause the processors to perform any one or more of the methodologies disclosed herein. The computer-readable medium may include, but not be limited to, data repositories in the form of solid-state memories, optical media, and magnetic media. The computer-readable medium does not include a transitory medium such as a propagating signal or a carrier wave.

Example Embodiments

All features of various embodiments described in this section can be combined with another embodiment described in this section or any embodiments described in other figures.

In some embodiments, the techniques described herein relate to a system including: a body surface device carrying a plurality of electrodes configured to be in contact with a body surface of a subject, the electrodes configured to cover one or more spatial projections of one or more areas of a heart projected on the body surface, wherein the electrodes are configured to detect a plurality of electrical signals generated by the heart of the subject, wherein the body surface device is configured to record from an area of less than one half of torso surface of the subject; and a computing device configured to receive signal data generated from the body surface device, the computing device including a processor and memory, the memory, when executed by the processor, causes the processor to perform operations including: determining one or more locations of the heart that are associated with a heart rhythm disorder based on the signal data.

In some embodiments, the techniques described herein relate to a system, wherein the operations performed by the processor further include: computing a predicted success score for a planned therapy for eliminating one or more regions that initiate an onset of the heart rhythm disorder or regions that maintain the heart rhythm disorder.

In some embodiments, the techniques described herein relate to a system, wherein the planned therapy targets pulmonary veins.

In some embodiments, the techniques described herein relate to a system, wherein the planned therapy targets regions are in the left side or right side of the heart.

In some embodiments, the techniques described herein relate to a system, wherein the heart rhythm disorder is atrial fibrillation.

In some embodiments, the techniques described herein relate to a system, wherein the operations performed by the processor further include: guiding a probe towards one of the locations of the heart that are associated with the heart rhythm disorder.

In some embodiments, the techniques described herein relate to a system, wherein the probe contains sensors for recording.

In some embodiments, the techniques described herein relate to a system, wherein the probe is capable of delivering energy to modify tissue regions related to the heart rhythm disorder.

In some embodiments, the techniques described herein relate to a system, wherein the computing device is a computing server that is geographically remote from the body surface device.

In some embodiments, the techniques described herein relate to a system, wherein the body surface device further includes a substrate that includes one or more regions, each region configured to be in contact with one of torso quadrants of the subject, the torso quadrants being a right anterior, a left anterior, a left posterior, and a right posterior, wherein the substrate includes at least one region configured to be in contact with at least one of the torso quadrants.

In some embodiments, the techniques described herein relate to a system, wherein determining the one or more locations of the heart that are associated with the heart rhythm disorder includes a phase analysis, an analysis of spatial patterns of electrical activation over time, a vectorial analysis, a spectral analysis, and/or signal featurization.

In some embodiments, the techniques described herein relate to a system, wherein determining the one or more locations of the heart that are associated with the heart rhythm disorder includes determining whether one of the locations is the left atrium, the right atrium, the left ventricle, or the right ventricle of the heart of the subject.

In some embodiments, the techniques described herein relate to a system, wherein determining one or more locations of the heart that are associated with the heart rhythm disorder includes inputting a version of the signal data to one or more machine learning models to determine one of the locations, at least one of the machine learning models are iteratively trained based on training samples of data associated with known heart rhythm disorders.

In some embodiments, the techniques described herein relate to a system, wherein the operations performed by the processor further include: calculating a cardiac output; determining if the cardiac output is reduced; and sending an alert that the cardiac output is reduced.

In some embodiments, the techniques described herein relate to a system, wherein the electrodes are configured to cover a spatial projection of at least a majority of a heart chamber projected on the body surface.

In some embodiments, the techniques described herein relate to a system, wherein the one or more locations of the heart that are associated with the heart rhythm disorder include: a location of beat that initiates onset of a heart rhythm disorder, and/or a location of a source region of the heart rhythm disorder.

In some embodiments, the techniques described herein relate to a system, wherein the body surface device is wearable during daily activities of the subject.

In some embodiments, the techniques described herein relate to a body surface device wearable by a subject, the body surface device including: a plurality of electrodes configured to be in contact with a body surface of the subject, the electrodes configured to cover one or more spatial projections of one or more areas of a heart projected on the body surface, wherein the electrodes are configured to detect a plurality of electrical signals generated by the heart of the subject, wherein the body surface device is configured to record from an area of less than one half of torso surface of the subject; and a transmitter configured to transmit a version of signal data for the plurality of electrical signals for a computing device that is configured to determine one or more locations of the heart that are associated with a heart rhythm disorder based on the signal data.

In some embodiments, the techniques described herein relate to a body surface device, wherein the plurality of electrodes are configured to detect the electrical signals respectively from the left atrium, the right atrium, the left ventricle, or the right ventricle of the heart.

In some embodiments, the techniques described herein relate to a body surface device, wherein determining one or more locations of the heart that are associated with the heart rhythm disorder includes determining whether one of the locations is the left atrium, the right atrium, the left ventricle, or the right ventricle of the heart of the subject.

In some embodiments, the techniques described herein relate to a body surface device, wherein the one or more locations of the heart that are associated with the heart rhythm disorder include: a location of beat that initiates onset of a heart rhythm disorder, and/or a location of a source region of the heart rhythm disorder.

In some embodiments, the techniques described herein relate to a body surface device, wherein the computing device is further configured to computer a predicted success score for a planned therapy for eliminating one or more regions that initiate an onset of the heart rhythm disorder or regions that maintain the heart rhythm disorder.

In some embodiments, the techniques described herein relate to a body surface device, wherein the computing device is a computing server that is geographically remote from the body surface device.

In some embodiments, the techniques described herein relate to a body surface device, wherein the computing device is an electronic device used by the subject.

In some embodiments, the techniques described herein relate to a body surface device, wherein the electrodes are configured to cover a spatial projection of at least a majority of a heart chamber projected on the body surface.

In some embodiments, the techniques described herein relate to a body surface device, further including: a substrate including one or more regions, each region configured to be in contact with one of torso quadrants of the subject, the torso quadrants being a right anterior, a left anterior, a left posterior, and a right posterior, wherein the substrate includes at least one region configured to be in contact with at least one of the torso quadrants.

In some embodiments, the techniques described herein relate to a method including: receiving signal data generated from a body surface device, a body surface device carrying a plurality of electrodes configured to be in contact with a body surface of a subject, the electrodes configured to cover one or more spatial projections of one or more areas of a heart projected on the body surface, wherein the electrodes are configured to detect a plurality of electrical signals generated by the heart of the subject, wherein the body surface device records from an area of less than one half of torso surface of the subject; and determining one or more locations of the heart that are associated with a heart rhythm disorder based on the signal data.

In some embodiments, the techniques described herein relate to a method, wherein the one or more locations of the heart that are associated with the heart rhythm disorder include: a location of beat that initiates onset of a heart rhythm disorder, and/or a location of a source region of the heart rhythm disorder.

In some embodiments, the techniques described herein relate to a method, wherein determining one or more locations of the heart that are associated with the heart rhythm disorder includes a phase analysis, an analysis of spatial patterns of electrical activation over time, a vectorial analysis, a spectral analysis, and/or signal featurization.

In some embodiments, the techniques described herein relate to a method, further including: computing a predicted success score for a planned therapy for eliminating one or more regions that initiate an onset of the heart rhythm disorder or regions that maintain the heart rhythm disorder.

In some embodiments, the techniques described herein relate to a method, further including: guiding a probe towards one of the locations of the heart that are associated with the heart rhythm disorder.

In some embodiments, the techniques described herein relate to a method, wherein determining one or more locations of the heart is based on analysis of the electrical signals that identifies one or more of the following: areas of repetitive activity, regions of high rate or dominant frequency, drivers with rotational or focal activity, regions of low voltage suggesting scar, and/or signal signatures.

In some embodiments, the techniques described herein relate to a method, further including: generating a directionality map for the heart rhythm disorder based on the electrical signals, the directionality map describing pathways that indicate beats that initiate an onset of the heart rhythm disorder; determining source regions for the heart rhythm disorder, and generating a heat map for the heart rhythm disorder in the subject based on the directionality map.

In some embodiments, the techniques described herein relate to a method, wherein generating the directionality map includes applying a trained machine learning model to the electrical signals, wherein the machine learning model is trained on training examples including electrical signals of human hearts and known source regions of the heart rhythm disorder.

In some embodiments, the techniques described herein relate to a method for treating a heart rhythm disorder, the method including: receiving signal data for electrical signals of a heart detected by a plurality of sensing electrodes carried on a body surface device worn by a subject, the electrodes covering one or more spatial projections of one or more areas of a heart projected on a body surface of the subject; generating a directionality map for a probe based on the electrical signals to identify tissue for one of: a location of beat that initiates onset of a heart rhythm disorder in the directionality map, or a location of a source region of the heart rhythm disorder in the directionality map; and providing directional information from the directionality map to guide the probe towards a region of interest to treat the heart rhythm disorder.

In some embodiments, the techniques described herein relate to a method, further including determining one or more locations of the heart that are associated with the heart rhythm disorder based on a phase analysis, an analysis of spatial patterns of electrical activation over time, a vectorial analysis, a spectral analysis, and/or signal featurization.

In some embodiments, the techniques described herein relate to a method, wherein generating the directionality map includes applying a trained machine learning model to the electrical signals, wherein the machine learning model is trained on training examples including electrical signals of human hearts and known source regions of the heart rhythm disorder.

In some embodiments, the techniques described herein relate to a method, further including: computing a predicted success score for a planned therapy for eliminating one or more regions that initiate an onset of the heart rhythm disorder or regions that maintain the heart rhythm disorder.

In some embodiments, the techniques described herein relate to a method, further including: identifying the region of interest by the signal data detected by the body surface device; determining a number of a second set of electrodes carried by the probe that overlap with the region of interest to determine an area overlap; and causing, responsive to the area overlap being higher than a threshold, the probe to modify a tissue region at the region of interest.

In some embodiments, the techniques described herein relate to a method, wherein the directional information is generated further based on past records of the subject and data from a database of procedures.

In some embodiments, the techniques described herein relate to a method, wherein identifying the tissue is based on analysis of the electrical signals that identifies one or more of the following: areas of repetitive activity, regions of high rate or dominant frequency, drivers with rotational or focal activity, regions of low voltage suggesting scar, and/or signal signatures.

In some embodiments, the techniques described herein relate to a method, wherein the probe contains sensors for generating a second set of signal data for electrical signals of the heart detected by the sensors.

In some embodiments, the techniques described herein relate to a method, further including: generating a first directional vector from the signal data detected by the body surface device; generating a second directional vector from the second set of signal data detected by sensors of the probe; and generating a final directional vector that guides the probe based on the first directional vector and the second directional vector.

In some embodiments, the techniques described herein relate to a method, wherein the body surface device records from an area of less than one half of torso surface of the subject.

In some embodiments, the techniques described herein relate to a non-transitory computer-readable medium for storing computer code including instructions, the instructions, when executed by one or more processors, cause the one or more processors to perform operations for treating a heart rhythm disorder, the operations including: receiving signal data for electrical signals of a heart detected by a plurality of sensing electrodes carried on a body surface device worn by a subject, the electrodes covering one or more spatial projections of one or more areas of a heart projected on a body surface of the subject; generating a directionality map for a probe based on the electrical signals to identify tissue for one of: a location of beat that initiates onset of a heart rhythm disorder in the directionality map, or a location of a source region of the heart rhythm disorder in the directionality map; and providing directional information from the directionality map to guide the probe towards the identified tissue to treat the heart rhythm disorder.

In some embodiments, the techniques described herein relate to a non-transitory computer-readable medium, wherein the operations further include: generating a directionality map describing pathways of heart rhythms based on the electrical signals.

In some embodiments, the techniques described herein relate to a non-transitory computer-readable medium, wherein generating the directionality map includes applying a trained machine learning model to the electrical signals, wherein the machine learning model is trained on training examples including electrical signals of human hearts and known source regions of the heart rhythm disorder.

In some embodiments, the techniques described herein relate to a non-transitory computer-readable medium, wherein the operations further include: generating a directionality map for the heart rhythm disorder based on the electrical signals, the directionality map describing pathways that indicate beats that initiate an onset of the heart rhythm disorder; determining source regions for the heart rhythm disorder, and generating a heat map for the heart rhythm disorder in the subject based on the directionality map.

In some embodiments, the techniques described herein relate to a non-transitory computer-readable medium, wherein the operations further include: identifying the region of interest by the signal data detected by the body surface device; determining a number of a second set of electrodes carried by the probe that overlap with the region of interest to determine an area overlap; and causing, responsive to the area overlap being higher than a threshold, the probe to modify a tissue region at the region of interest.

In some embodiments, the techniques described herein relate to a non-transitory computer-readable medium, wherein the direction information is generated further based on past records of the subject and data from a database of procedures.

In some embodiments, the techniques described herein relate to a non-transitory computer-readable medium, wherein identifying the tissue is based on analysis of the electrical signals that identifies one or more of the following: areas of repetitive activity, regions of high rate or dominant frequency, drivers with rotational or focal activity, regions of low voltage suggesting scar, and/or signal signatures.

In some embodiments, the techniques described herein relate to a non-transitory computer-readable medium, wherein the probe contains sensors for generating a second set of signal data for electrical signals of the heart detected by the sensors.

In some embodiments, the techniques described herein relate to a non-transitory computer-readable medium, wherein the operations further include: generating a first directional vector from the signal data detected by the body surface device; generating a second directional vector from the second set of signal data detected by sensors of the probe; and generating a final directional vector that guides the probe based on the first directional vector and the second directional vector.

In some embodiments, the techniques described herein relate to a non-transitory computer-readable medium, wherein the body surface device records from an area of less than one half of torso surface of the subject.

In some embodiments, the techniques described herein relate to a body surface device wearable by a subject, the body surface device including: a substrate including one or more regions, each region configured to be in contact with one of torso quadrants of the subject, the torso quadrants being a right anterior, a left anterior, a left posterior, and a right posterior, wherein the substrate includes at least one region configured to be in contact with at least one of the torso quadrants; one or more sets of electrodes, each set of electrodes carried in one of the regions of the substrate, the one or more sets of electrodes configured to detect a plurality of electrical signals generated by a heart of the subject, wherein the set of electrodes, which are carried in the region configured to be in contact with the right anterior, the left anterior, the left posterior, or the right posterior, are configured to detect the electrical signals for detecting a heart rhythm disorder respectively from the left atrium, the right atrium, the left ventricle, or the right ventricle; and a transmitter configured to transmit a version of signal data for the plurality of electrical signals for a computing device that is configured to determine one or more locations of the heart that are associated with a heart rhythm disorder based on the signal data.

In some embodiments, the techniques described herein relate to a body surface device, wherein the computing device is a computing server that is geographically remote from the body surface device.

In some embodiments, the techniques described herein relate to a body surface device, wherein the computing device is an electronic device used by the subject.

In some embodiments, the techniques described herein relate to a body surface device, wherein the electrodes are configured to cover a spatial projection of at least a majority of a heart chamber projected on the body surface.

In some embodiments, the techniques described herein relate to a body surface device, wherein the computing device is further configured to computer a predicted success score for a planned therapy for eliminating one or more regions that initiate an onset of the heart rhythm disorder or regions that maintain the heart rhythm disorder.

In some embodiments, the techniques described herein relate to a method for determining one or more locations associated with a heart rhythm disorder, the method including: receiving signal data for electrical signals of a heart detected by a plurality of sensing electrodes carried on a body surface device worn by a subject, the electrodes covering one or more spatial projections of one or more areas of a heart projected on a body surface of the subject; inputting a version of the signal data to one or more machine learning models to determine one or more locations of the heart that are associated with a heart rhythm disorder, at least one of the machine learning models are iteratively trained based on training samples of data associated with known heart rhythm disorders; and determining, using the one or more machine learning models, whether one of the locations of the heart that are associated with the heart rhythm disorder is the left atrium, the right atrium, the left ventricle, or the right ventricle of the heart of the subject.

In some embodiments, the techniques described herein relate to a method, wherein determining one or more locations of the heart that are associated with the heart rhythm disorder includes a phase analysis, an analysis of spatial patterns of electrical activation over time, a vectorial analysis, a spectral analysis, and/or signal featurization.

In some embodiments, the techniques described herein relate to a method, further including: computing a predicted success score for a planned therapy for eliminating one or more regions that initiate an onset of the heart rhythm disorder or regions that maintain the heart rhythm disorder.

In some embodiments, the techniques described herein relate to a method, further including: guiding a probe towards one of the locations of the heart that are associated with the heart rhythm disorder.

In some embodiments, the techniques described herein relate to a method, further including: identifying the region of interest by the signal data detected by the body surface device; determining a number of a second set of electrodes carried by the probe that overlap with the region of interest to determine an area overlap; and causing, responsive to the area overlap being higher than a threshold, the probe to modify a tissue region at the region of interest.

In some embodiments, the techniques described herein relate to a method, further including generating a directionality map, generating the directionality map including applying a trained machine learning model to the electrical signals, wherein the machine learning model is trained on training examples including electrical signals of human hearts and known source regions of the heart rhythm disorder.

In some embodiments, the techniques described herein relate to a method for guiding an internal catheter using a body surface device, the method including: receiving a first set of signal data for electrical signals of a heart detected by a plurality of sensing electrodes carried on a body surface device worn by a subject, the electrodes covering one or more spatial projections of one or more areas of a heart projected on a body surface of the subject; receiving a second set of signal data for electrical signals of the heart detected by an internal catheter positioned within the heart or in contact with the heart; conducting a directionality analysis using the first set and the second set of signal data; and guiding a movement of the internal catheter towards a target tissue to treat a heart rhythm disorder based on the directionality analysis.

In some embodiments, the techniques described herein relate to a method, wherein conducting the directionality analysis includes inputting a version of the first set of signal data and a version of the second set of signal data to one or more machine learning models to generate a directional vector.

In some embodiments, the techniques described herein relate to a method, wherein the one or more machine learning models are trained based on training samples with output labels that monitor one or more of the following: whether a treatment was acutely successful, whether a treatment produced freedom from arrhythmia for at least a threshold period of time, and/or whether a treatment produced a good quality of life based on clinical determination.

In some embodiments, the techniques described herein relate to a method, wherein conducting the directionality analysis includes: generating a first directional vector from the first set of signal data detected by the body surface device; generating a second directional vector from the second set of signal data detected by the internal catheter; and generating a final directional vector that guides the movement of the internal catheter based on the first directional vector and the second directional vector.

In some embodiments, the techniques described herein relate to a method, wherein conducting the directionality analysis includes: comparing spatial activation patterns between data from the body surface device and data from the internal catheter.

In some embodiments, the techniques described herein relate to a method, wherein conducting the directionality analysis includes: comparing timing information between data from the body surface device and data from the internal catheter.

In some embodiments, the techniques described herein relate to a method, wherein conducting the directionality analysis includes: generating a first directional vector from the first set of signal data detected by the body surface device; generating a second directional vector from the second set of signal data detected by the internal catheter; determining that the first directional vector and the second directional vector are dissimilar; and generating a guidance on the movement of the internal catheter using past records of the subject and data from a database of procedures.

In some embodiments, the techniques described herein relate to a method, wherein the body surface device records from a surface area that is less than 200 $cm^2$.

In some embodiments, the techniques described herein relate to a method, wherein the directionality analysis is conducted without an anatomical three dimensional reconstruction.

In some embodiments, the techniques described herein relate to a method, wherein conducting the directionality analysis includes: identifying a region of interest by the first set of signal data detected by the body surface device; determining a number of a second set of electrodes carried by the internal catheter that overlap with the region of interest to determine an area overlap; and causing, responsive to the area overlap being higher than a threshold, the internal catheter to modify a tissue region at the region of interest.

In some embodiments, the techniques described herein relate to a treatment system for providing therapy to treat a heart rhythm disorder, the treatment system including: a body surface device configured to be worn by a subject, the body surface device including a plurality of sensing electrodes configured to detect electrical signals of a heart of the subject to generate a first set of signal data, the electrodes covering one or more spatial projections of one or more areas of a heart projected on a body surface of the subject; an internal catheter configured to be positioned within the heart or in contact with the heart, the internal catheter configured to detect electrical signals of the heart to generate a second set of signal data; and a computing device configured to: conduct a directionality analysis using the first set and the second set of signal data; and guide a movement of the internal catheter towards a target tissue to treat a heart rhythm disorder based on the directionality analysis.

In some embodiments, the techniques described herein relate to a system, wherein conducting the directionality analysis includes inputting a version of the first set of signal data and a version of the second set of signal data to one or more machine learning models to generate a directional vector.

In some embodiments, the techniques described herein relate to a system, wherein the one or more machine learning models are trained based on training samples with output labels that monitor one or more of the following: whether a treatment was acutely successful, whether a treatment produced freedom from arrhythmia for at least a threshold period of time, and/or whether a treatment produced a good quality of life based on clinical determination.

In some embodiments, the techniques described herein relate to a system, wherein conducting the directionality analysis includes: generating a first directional vector from the first set of signal data detected by the body surface device; generating a second directional vector from the second set of signal data detected by the internal catheter; and generating a final directional vector that guides the movement of the internal catheter based on the first directional vector and the second directional vector.

In some embodiments, the techniques described herein relate to a system, wherein conducting the directionality analysis includes: comparing spatial activation patterns between data from the body surface device and data from the internal catheter.

In some embodiments, the techniques described herein relate to a system, wherein conducting the directionality analysis includes: comparing patterns of spatial activation between the body surface device and the internal catheter.

In some embodiments, the techniques described herein relate to a system, wherein conducting the directionality analysis includes: generating a first directional vector from the first set of signal data detected by the body surface device; generating a second directional vector from the second set of signal data detected by the internal catheter; determining that the first directional vector and the second directional vector are dissimilar; and generating a guidance on the movement of the internal catheter using past records of the subject and data from a database of procedures.

In some embodiments, the techniques described herein relate to a system, wherein the body surface device records from a surface area that is less than 200 $cm^2$.

In some embodiments, the techniques described herein relate to a system, wherein the directionality analysis is conducted without an anatomical three dimensional reconstruction.

In some embodiments, the techniques described herein relate to a system, wherein conducting the directionality analysis includes: identifying a region of interest by the first set of signal data detected by the body surface device; determining a number of a second set of electrodes carried by the internal catheter that overlap with the region of interest to determine an area overlap; and causing, responsive to the area overlap being higher than a threshold, the internal catheter to modify a tissue region at the region of interest.

In some embodiments, the techniques described herein relate to a computing device for controlling treatment of a heart rhythm disorder by a treatment probe, the computing device including: a processor; and memory, the memory, when executed by the processor, causes the processor to perform operations including: receiving a first set of signal data for electrical signals of a heart detected by a plurality of sensing electrodes carried on a body surface device worn by a subject, the electrodes covering one or more spatial projections of one or more areas of a heart projected on a body surface of the subject; receiving a second set of signal data for electrical signals of the heart detected by an internal catheter positioned within the heart or in contact with the heart; conducting a directionality analysis using the first set and the second set of signal data; and guiding a movement of the internal catheter towards a target tissue to treat a heart rhythm disorder based on the directionality analysis.

In some embodiments, the techniques described herein relate to a computing device, wherein conducting the directionality analysis includes inputting a version of the first set of signal data and a version of the second set of signal data to one or more machine learning models to generate a directional vector.

In some embodiments, the techniques described herein relate to a computing device, wherein the one or more machine learning models are trained based on training samples with output labels that monitor one or more of the following: whether a treatment was acutely successful, whether a treatment produced freedom from arrhythmia for at least a threshold period of time, and/or whether a treatment produced a good quality of life based on clinical determination.

In some embodiments, the techniques described herein relate to a computing device, wherein conducting the directionality analysis includes: generating a first directional vector from the first set of signal data detected by the body surface device; generating a second directional vector from the second set of signal data detected by the internal catheter; and generating a final directional vector that guides the movement of the internal catheter based on the first directional vector and the second directional vector.

In some embodiments, the techniques described herein relate to a computing device, wherein conducting the directionality analysis includes: comparing spatial activation patterns between data from the body surface device and data from the internal catheter.

In some embodiments, the techniques described herein relate to a computing device, wherein conducting the directionality analysis includes: comparing timing information between data from the body surface device and data from the internal catheter.

In some embodiments, the techniques described herein relate to a computing device, wherein conducting the directionality analysis includes: generating a first directional vector from the first set of signal data detected by the body surface device; generating a second directional vector from the second set of signal data detected by the internal catheter; determining that the first directional vector and the second directional vector are dissimilar; and generating a guidance on the movement of the internal catheter using past records of the subject and predetermined clinical rules.

In some embodiments, the techniques described herein relate to a computing device, wherein the body surface device records from a surface area that is less than 200 $cm^2$.

In some embodiments, the techniques described herein relate to a computing device, wherein the directionality analysis is conducted without an anatomical three dimensional reconstruction.

In some embodiments, the techniques described herein relate to a computing device, wherein conducting the directionality analysis includes: identifying a region of interest by the first set of signal data detected by the body surface device; determining a number of a second set of electrodes carried by the internal catheter that overlap with the region of interest to determine an area overlap; and causing, responsive to the area overlap being higher than a threshold, the internal catheter to modify a tissue region at the region of interest.

ADDITIONAL CONSIDERATIONS

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Any feature mentioned in one claim category, e.g. method, can be claimed in another claim category, e.g. computer program product, system, storage medium, as well. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject-matter may include not only the combinations of features as set out in the disclosed embodiments but also any other combination of features from different embodiments. Various features mentioned in the different embodiments can be combined with explicit mentioning of such combination or arrangement in an example embodiment or without any explicit mentioning. Furthermore, any of the embodiments and features described or depicted herein may be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In some embodiments, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed by the specific order claimed or described in the disclosure. Some steps may be performed before others even though the other steps are claimed or described first in this disclosure. Likewise, any use of (i), (ii), (iii), etc., or (a), (b), (c), etc. in the specification or in the claims, unless specified, is used to better enumerate items or steps and also does not mandate a particular order.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A. In claims, the use of a singular form of a noun may imply at least one element even though a plural form is not used.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

The invention claimed is:

1. A system for providing therapy to treat a heart rhythm disorder, the system comprising:
   a body surface device configured to be worn by a subject, the body surface device comprising a plurality of sensing electrodes configured to detect electrical signals of a heart of the subject to generate signal data for the electrical signals; and
   a computing device comprising memory and a processor, the memory storing code comprising instructions, wherein the instructions, when executed by the processor, cause the processor to perform steps comprising:
      receiving the signal data from the body surface device;
      generating, based on the signal data detected by the plurality of sensing electrodes, a vectorial direction to guide a probe to approach towards a location of interest, the vectorial direction being a vector that separates at least left, right, anterior and posterior, the vectorial direction guiding the probe towards an anatomical region of the heart that carries the location of interest, the location of interest being one of:
         a location of beat that initiates onset of the heart rhythm disorder, or
         a location of a source region of the heart rhythm disorder; and
      updating, based on the signal data detected by the plurality of sensing electrodes, the vectorial direction as the probe moves inside the heart to guide the probe towards the location of interest to treat the heart rhythm disorder.

2. The system of claim 1, wherein the steps further comprise:
   determining one or more locations of the heart that are associated with the heart rhythm disorder based on a phase analysis, an analysis of spatial patterns of electrical activation over time, a vectorial analysis, a spectral analysis, and/or signal featurization.

3. The system of claim 1, wherein the vectorial direction that guides the probe to approach towards the location of interest is generated without creating an anatomical 3D reconstruction.

4. The system of claim 1, wherein the left, right, anterior and posterior correspond to torso quadrants of a right anterior, a left anterior, a left posterior, and a right posterior.

5. The system of claim 1, wherein the steps further comprise:
   computing a predicted success score for a planned therapy for eliminating one or more regions that initiate an onset of the heart rhythm disorder or regions that maintain the heart rhythm disorder.

6. The system of claim 1, wherein the steps further comprise:
    identifying the location of interest by the signal data detected by the body surface device;
    determining a number of a second set of electrodes carried by the probe that overlap with the location of interest to determine an area overlap; and
    causing, responsive to the area overlap being higher than a threshold, the probe to modify a tissue region at the location of interest.

7. The system of claim 1, wherein the vector is a first directional vector, and the steps further comprise:
    generating a second directional vector from a second set of signal data detected by sensors of the probe; and
    generating a final directional vector that guides the probe based on the first directional vector and the second directional vector.

8. The system of claim 7, wherein generating the final directional vector comprises: comparing the first directional vector with the second directional vector;
    determining that a degree of similarity between the first directional vector and the second directional vector is below a threshold; and
    generating the final directional vector further based on past records of the subject.

9. The system of claim 1, wherein generating the vectorial direction based on the signal data detected by the plurality of sensing electrodes comprises:
    determining an inter-electrode distance between two of the sensing electrodes carried on a body surface device;
    determining an activation time; and
    determining a conduction velocity at one of the sensing electrodes based on the inter-electrode distance and the activation time.

10. The system of claim 1, wherein the heart rhythm disorder is an atrial fibrillation that is focal or rotational, and wherein generating the vectorial direction based on the signal data detected by the plurality of sensing electrodes comprises:
    taking an average over multiple cycles to identify a predominant vectorial direction.

* * * * *